US012358901B2

(12) United States Patent
Alvaro et al.

(10) Patent No.: US 12,358,901 B2
(45) Date of Patent: Jul. 15, 2025

(54) KV3 MODULATORS

(71) Applicant: Autifony Therapeutics Limited, Stevenage (GB)

(72) Inventors: Giuseppe Alvaro, Stevenage (GB); Agostino Marasco, Stevenage (GB)

(73) Assignee: Autifony Therapeutics Limited, Stevenage (GB)

( * ) Notice: Subject to any disclaimer, the term of this patent is extended or adjusted under 35 U.S.C. 154(b) by 1053 days.

(21) Appl. No.: 17/232,049

(22) Filed: Apr. 15, 2021

(65) Prior Publication Data

US 2021/0276985 A1    Sep. 9, 2021

Related U.S. Application Data

(63) Continuation of application No. PCT/GB2020/050268, filed on Feb. 6, 2020, and a continuation-in-part of application No. PCT/GB2019/052937, filed on Oct. 16, 2019.

(30) Foreign Application Priority Data

Oct. 16, 2018   (EP) .................................. 18200626

(51) Int. Cl.
*C07D 405/14*   (2006.01)
(52) U.S. Cl.
CPC .................................. *C07D 405/14* (2013.01)
(58) Field of Classification Search
CPC .................................................... C07D 405/14
See application file for complete search history.

(56) References Cited

U.S. PATENT DOCUMENTS

| 9,133,175 | B2 * | 9/2015 | Alvaro | A61K 31/506 |
| 9,669,030 | B2 * | 6/2017 | Large | C07D 405/14 |
| 9,833,452 | B2 * | 12/2017 | Alvaro | C07D 307/94 |
| 10,835,534 | B2 * | 11/2020 | Alvaro | A61P 27/16 |
| 11,147,813 | B2 * | 10/2021 | Large | A61K 31/4196 |
| 11,944,623 | B2 * | 4/2024 | Large | C07D 307/94 |
| 2014/0148462 | A1 * | 5/2014 | Eckhardt | A61K 31/443 |
| | | | | 514/395 |
| 2020/0131156 | A1 | 4/2020 | Sams et al. | |

FOREIGN PATENT DOCUMENTS

| TW | 22035394 A | 10/2020 |
| WO | WO 2008/046135 A1 | 4/2008 |
| WO | WO 2011/069951 A1 | 6/2011 |
| WO | 2012-076877 A | 6/2012 |
| WO | WO 2012/151640 A1 | 11/2012 |
| WO | WO 2012/168710 A1 | 12/2012 |
| WO | 2013-083994 A1 | 6/2013 |
| WO | WO 2013/175211 A1 | 11/2013 |
| WO | WO 2013/175215 A1 | 11/2013 |
| WO | 2013-182851 A1 | 12/2013 |
| WO | 2017-103604 A1 | 6/2017 |
| WO | WO 2017/098254 A1 | 6/2017 |
| WO | WO 2018/020263 A1 | 2/2018 |
| WO | 2018-109484 A1 | 6/2018 |
| WO | WO 2019/222816 A1 | 11/2019 |
| WO | WO 2020/000065 A2 | 1/2020 |
| WO | 2020-079422 A1 | 6/2020 |
| WO | WO 2021/056048 A1 | 4/2021 |
| WO | WO 2021/214090 A1 | 10/2021 |
| WO | WO 2023/017263 A1 | 2/2023 |

OTHER PUBLICATIONS

MayoClinic. Selective serotonin reuptake inhibitors. Retrieved from the WayBack Machine on Jan. 25, 2024. Published Sep. 27, 2018. (Year: 2018).*
C.G. Wermuth, P. Ciapetti, B. Giethlen, P. Bazzini, 2.16—Bioisosterism, Editor(s): John B. Taylor, David J. Triggle, Comprehensive Medicinal Chemistry II, (Year: 2007).*
Paola Ciapetti, Bruno Giethlen, Chapter 8—Molecular Variations Based on Isosteric Replacements, Editor(s): Camille Georges Wermuth, David Aldous, Pierre Raboisson, Didier Rognan, The Practice of Medicinal Chemistry (Fourth Edition), Academic Press, 2008. (Year: 2008).*
EP Certified European Patent Application No. 18200626.2 to Autifony Therapeutics Limited; 83 pgs.
EPO—International Search Report for related International Application No. PCT/GB2019/052937 mailed on Apr. 23, 2020; 5 pgs.
EPO—Written Opinion for related International Application No. PCT/GB2019/052937 mailed on Apr. 23, 2020; 5 pgs.
(Continued)

*Primary Examiner* — James H Alstrum-Acevedo
*Assistant Examiner* — Lauren Wells
(74) *Attorney, Agent, or Firm* — McDermott Will & Emery LLP; Brennen P. Baylor; Judy M. Mohr

(57) ABSTRACT

Disclosed is a compound of formula (I)

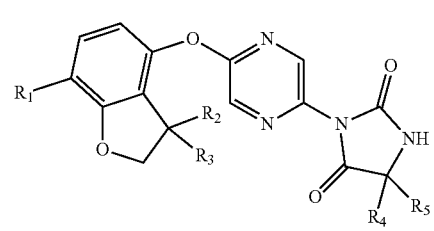

(I)

Wherein $R_1$ is H or methyl, $R_2$ and $R_3$ are both methyl, or $R_2$ and $R_3$, together with the carbon atom to which they are attached, are a spirocyclopropyl ring, $R_4$ is methyl or ethyl, $R_5$ is H or methyl, or $R_4$ and $R_5$, together with the carbon atom to which they are attached, form a $C_3$-$C_4$ spiro carbocyclyl. Also disclosed are methods for treating and/or preventing one or more diseases or disorders comprising administering to a subject an effective amount of a compound of formula (I) or a pharmaceutically acceptable salt, solvate and/or derivative thereof. Additionally, methods of using a compound of formula (I) to manufacture medicaments are provided.

3 Claims, No Drawings

(56) References Cited

OTHER PUBLICATIONS

Bastin et al., "Salt Selection and Optimisation Procedures for Pharmaceutical New Chemical Entities", Organic Process Research & Development, vol. 4, No. 5, pp. 427-435 (2000).
Kummerer, "Pharmaceuticals in the Environment", Annu. Rev. Environ. Resour., vol. 35, pp. 57-75 (2010).
Wang et al., "Revisiting the SAR of the Antischistosomal Aryl Hydantoin (Ro 13-3978)", J. Med. Chem., vol. 59, pp. 10705-10718 (2016).
Belikov et al., "Pharmaceutical Chemistry", Chapter 2.6 "The relationship between the Y chemical structure, properties of substances and their effect on the body", Farmatsevticheskaya khimiya, Moscow, Publishing house "MEDpress-inform", pp. 27-29 (2007) *Russian Language with Partial English Translation.*
Li, "Drug Structure-Activity Relationship", China Medical Science and Technology Press, ISBN: 7506727730, pp. 182-185 (Jan. 2004) *Chinese Language Only.*

\* cited by examiner

KV3 MODULATORS

CROSS-REFERENCE TO RELATED APPLICATIONS

This application is a continuation of International Patent Application No. PCT/GB2020/050268, filed on Feb. 6, 2020, and a continuation-in-part of International Patent Application No. PCT/GB2019/052937, filed on Oct. 16, 2019, which claims priority to European Patent Application No. 18200626.2, filed on Oct. 16, 2018, the contents of each of which are incorporated by reference herein in their entireties.

BACKGROUND OF THE INVENTION

Technical Field

This invention relates to novel compounds, pharmaceutical compositions containing them and their use in therapy, in particular in the prophylaxis or treatment of hearing disorders, including hearing loss and tinnitus, as well as schizophrenia, substance abuse disorders, pain and Fragile X syndrome.

The Kv3 voltage-gated potassium channel family includes four members, Kv3.1, Kv3.2, Kv3.3, and Kv3.4. Kv3 channels are activated by depolarisation of the plasma membrane to voltages more positive than −20 mV; furthermore, the channels deactivate rapidly upon repolarisation of the membrane. These biophysical properties ensure that the channels open towards the peak of the depolarising phase of the neuronal action potential to initiate repolarisation. Rapid termination of the action potential mediated by Kv3 channels allows the neuron to recover more quickly to reach sub-threshold membrane potentials from which further action potentials can be triggered. As a result, the presence of Kv3 channels in certain neurons contributes to their ability to fire at high frequencies (Rudy et al., 2001). Kv3.1-3 subtypes are predominant in the CNS, whereas Kv3.4 channels are also found in skeletal muscle and sympathetic neurons (Weiser et al., 1994). Kv3.1-3 channel subtypes are differentially expressed by sub-classes of interneurons in cortical and hippocampal brain areas (e.g. Chow et al., 1999; Martina et al., 1998; McDonald et al., 2006; Chang et al., 2007), in the thalamus (e.g. Kasten et al., 2007), cerebellum (e.g. Sacco et al., 2006; Puente et al., 2010), and auditory brain stem nuclei (Li et al., 2001).

Tetraethylammonium (TEA) has been shown to inhibit the channels at low millimolar concentrations (Rudy et al., 2001), and blood-depressing substance (BDS) toxins from the sea anemone, *Anemonia sulcata* (Diochot et al., 1998), have been shown to selectively inhibit Kv3 channels with high affinity (Yeung et al., 2005).

Kv3 channels are important determinants of the function of the cerebellum, a region of the brain important for motor control (Joho et al., 2009). Characterisation of mice in which one or more of the Kv3 subtypes has been deleted shows that the absence of Kv3.1 gives rise to increased locomotor activity, altered electroencephalographic activity, and a fragmented sleep pattern (Joho et al., 1999). The deletion of Kv3.2 leads to a reduction in seizure threshold and altered cortical electroencephalographic activity (Lau et al., 2000). Deletion of Kv3.3 is associated with mild ataxia and motor deficits (McMahon et al., 2004). Double deletion of Kv3.1 and Kv3.3 gives rise to a severe phenotype characterised by spontaneous seizures, ataxia, and an increased sensitivity to the effects of ethanol (Espinosa et al., 2001; Espinosa et al., 2008). A spontaneous mutation in the Kv3.1 gene (KCNC1) causes progressive myoclonic epilepsy (Muona et al., 2014). Mutations of the Kv3.3 gene (KCNC3) in humans have been associated with forms of spinocerebellar ataxia (SCA13) (Figueroa et al., 2010).

Bipolar disorder, schizophrenia, anxiety, and epilepsy are serious disorders of the central nervous system that have been associated with reduced function of inhibitory interneurons and gamma-amino butyric acid (GABA) transmission (Reynolds et al., 2004; Benes et al., 2008; Brambilla et al., 2003; Aroniadou-Anderjaska et al., 2007; Ben-Ari, 2006). Parvalbumin positive basket cells that express Kv3 channels in the cortex and hippocampus play a key role in generating feedback inhibition within local circuits (Markram et al., 2004). Given the relative dominance of excitatory synaptic input over inhibitory input to glutamatergic pyramidal neurons in these circuits, fast-firing of interneurons supplying inhibitory input is essential to ensure balanced inhibition. Furthermore, accurate timing of inhibitory input is necessary to sustain network synchronisation, for example, in the generation of gamma frequency field potential oscillations that have been associated with cognitive function (Fisahn et al., 2005; Engel et al., 2001). Notably, a reduction in gamma oscillations has been observed in patients with schizophrenia (Spencer et al., 2004), and evidence suggests reduced expression of Kv3.1, but not Kv3.2 in the dorsolateral prefrontal cortex of patients with schizophrenia who had not been taking antipsychotic drugs for at least 2 months before death (Yanagi et al., 2014). Consequently, positive modulators of Kv3 channels might be expected to enhance the firing capabilities of specific groups of fast-firing neurons in the brain. These effects may be beneficial in disorders associated with abnormal activity of these neuronal groups. In addition, Kv3.2 channels have been shown to be expressed by neurons of the superchiasmatic nucleus (SCN) the main circadian pacemaker in the CNS (Schulz et al., 2009).

Voltage-gated ion channels of the Kv3 family are expressed at high levels in auditory brainstem nuclei (Li et al., 2001) where they permit the fast firing of neurons that transmit auditory information from the cochlear to higher brain regions. Phosphorylation of Kv3.1 and Kv3.3 channels in auditory brainstem neurons is suggested to contribute to the rapid physiological adaptation to sound levels that may play a protective role during exposure to noise (Desai et al., 2008; Song et al., 2005). Loss of Kv3.1 channel expression in central auditory neurons is observed in hearing impaired mice (von Hehn et al., 2004); furthermore, a decline in Kv3.1 expression may be associated with loss of hearing in aged mice (Jung et al. 2005), and loss of Kv3 channel function may also follow noise-trauma induced hearing loss (Pilati et al., 2012). Furthermore, pathological plasticity of auditory brainstem networks is likely to contribute to symptoms that are experienced by many people suffering from hearing loss of different types. Recent studies have shown that regulation of Kv3.1 channel function and expression has a major role in controlling auditory neuron excitability (Kaczmarek et al., 2005; Anderson et al., 2018; Glait et al., 2018; Olsen et al., 2018, Chambers et al., 2017), suggesting that this mechanism could account for some of the plastic changes that give rise to tinnitus. Tinnitus may follow noise-induced hearing loss as a result of adaptive changes in central auditory pathways from brainstem to auditory cortex (Roberts et al., 2010). Kv3.1 and/or Kv3.2 channels are expressed in many of these circuits and contribute to the function of GABAergic inhibitory interneurons that may control the function of these circuits.

Description of the Related Art

It is known that Kv3.1 and/or Kv3.2 modulators have utility in the treatment of pain (see, for example, International Patent Application Publication No. 2017/098254). In the broadest sense, pain can be grouped in to acute pain and chronic pain. Acute pain is defined as pain that is self-limited and generally requires treatment for no more than up to a few weeks, for example postoperative or acute musculoskeletal pain, such as fractures (US Food and Drug Administration, 2014). Chronic pain can be defined either as pain persisting for longer than 1 month beyond resolution of the initial trauma, or pain persisting beyond three months. There is often no clear cause of chronic pain, and a multitude of other health problems such as fatigue, depression, insomnia, mood changes and reduction in movement, often accompany chronic pain.

Chronic pain can be sub-divided in to the following groups: neuropathic pain, chronic musculoskeletal pain and miscellaneous chronic pain. Neuropathic pain usually accompanies tissue injury and is initiated or caused by damage to the nervous system (peripheral nervous system and/or central nervous system), such as amputation, stroke, diabetes, or multiple sclerosis. Chronic musculoskeletal pain can be a symptom of diseases such as osteoarthritis and chronic lower back pain and can occur following damage to muscle tissue as well as trauma to an area for example, fractures, sprains and dislocation. Miscellaneous chronic pain encompasses all other types of long term pain and includes non-neuropathic pain conditions such as cancer pain and fibromyalgia as well as headaches and tendinitis.

Chronic pain is a highly heterogeneous condition that remains amongst the most troublesome and difficult to manage of clinical indications (McCarberg et al., 2008; Woolf, 2010; Finnerup et al., 2015). Despite years of research and drug development, there has been little progress in identifying treatments that can match the opioids for efficacy without significant side effects and risk of dependence. Voltage-gated ion channels have been important targets for the management of specific pain indications, in particular neuropathic pain states. Furthermore, genetic mutations in specific ion channels have been linked to some chronic pain disorders (Bennett et al., 2014). Examples of voltage-gated ion channels that are being explored as pharmaceutical targets include: Sodium channels (in particular NaV1.7)—Sun et al., 2014; Dib-Hajj et al., 2013; *N-type calcium channels*—Zamponi et al., 2015; *Kv7 potassium channels*—Devulder, 2010; Wickenden et al., 2009; and *SLACK*—Lu et al., 2015.

The hypothesis underlying these approaches is that chronic pain states are associated with increased excitability and/or aberrant firing of peripheral sensory neurons, in particular neurons involved in the transmission of painful sensory stimuli, such as the C-fibres of the dorsal root ganglia and specific circuits within the spinal cord (Baranauskas et al., 1998; Cervero, 2009; Woolf et al., 2011; Baron et al., 2013). Animal models of neuropathic and inflammatory chronic pain provide the main support for this hypothesis, although demonstration of causality is still lacking (Cervero, 2009).

Drugs targeting hyperexcitability, such as sodium channel blockers (e.g. CNV1014802, lamotrigine, carbamazepine, and local anaesthetics), Kv7 positive modulators (e.g. flupertine and retigabine), and N-type calcium channel modulators (e.g. gabapentin, which interacts with the α2δ subunit of the N-type calcium channel, and ziconitide, derived from a cone snail toxin) show efficacy in models of inflammatory and/or neuropathic pain. However, amongst these drugs, there is mixed evidence for clinical efficacy, for example, balancing efficacy and increased burden of side effects on the central nervous system. The disparity between efficacy in animal models and efficacy in humans is likely to be due to a range of factors, but in particular, drug concentration achievable in humans (due to poor tolerability) and heterogeneity of human pain conditions are likely to be the main culprits. For pain indications, there is also a need to identify targets through which pain relief can be achieved with reduced tolerance or tachyphylaxis and reduced abuse liability and/or risk of dependence.

Thus, improving the pharmacological management of pain is focused on mechanisms that can deliver good efficacy with a reduced side-effect burden, reduced tolerance or tachyphylaxis, and reduced abuse liability and/or risk of dependence.

Recently, Kv3.4 channels have become a target of interest for the treatment of chronic pain. Kv3.4 channels are expressed on neurons of the dorsal root ganglia (Ritter et al., 2012; Chien et al., 2007), where they are predominantly expressed on sensory C-fibres (Chien et al., 2007). Kv3 channels are also expressed by specific subsets of neurons in the spinal cord. Specifically, Kv3.1b (Deuchars et al., 2001; Brooke et al., 2002), Kv3.3 (Brooke et al., 2006), and Kv3.4 subunits (Brooke et al., 2004) have been identified in rodent spinal cord, although not always in association with circuits involved with sensory processing. It is likely that Kv3 channels shape the firing properties of spinal cord neurons, including motoneurons.

In addition recent studies showed the Kv3.4 channels expressed in DRG nociceptors have a significant impact on glutamatergic synaptic transmission (Muqeem et al., 2018). animal model data suggest a down-regulation of Kv3.4 channel surface expression in DRG neurons following spinal cord injury associated with hypersensitivity to painful stimuli (Ritter et al., 2015; Zemel et al., 2017; Zemel et al., 2018). Similarly, it has been observed that there is a down-regulation of Kv3.4 expression in DRGs of rodents following spinal cord ligation (Chien et al., 2007). This latter study also showed that intrathecal administration to rats of an antisense oligonucleotide to suppress the expression of Kv3.4 led to hypersensitivity to mechanical stimuli. It has been shown that Kv3.4 channel inactivation could be influenced by protein kinase C-dependent phosphorylation of the channels, and that this physiological mechanism might allow DRG neurons to alter their firing characteristics in response to painful stimuli (Ritter et al., 2012). These studies suggest a causal relationship between the emergence of mechanical allodynia and reduced Kv3.4 channel expression or function. No evaluation of Kv3.1, Kv3.2, or Kv3.3 expression in SC or DRG neurons was conducted in any of these studies, and expression of these two subtypes has not been explicitly demonstrated on DRG neurons (although as mentioned above, they are abundant within specific regions of the spinal cord). The in vivo studies reported above provide a rationale for modulation of Kv3.4 as a novel approach to the treatment of certain neuropathic pain states.

Dementia with Lewy Bodies (DLB) and Parkinson's disease (PD) are serious neurodegenerative disorders that are associated with the accumulation of the protein, alpha-synuclein in Lewy bodies, which leads to loss of connectivity and neuronal cell death. Symptoms of DLB include progressive cognitive deficits, in particular difficulties with planning and attention. Visual hallucinations are also common, occurring in approximately 60% of patients. PD is associated initially with motor deficits, primarily due to loss of dopamine neurons. While there are currently no studies directly linking Kv3 channels to DLB or PD, the location and role of Kv3 channels, in particular Kv3.1, in cortical and basal ganglia circuits suggests that modulators of these channels could improve symptoms of DLB or PD, either alone, or in combination with current treatments, such as acetyl-cholinesterase inhibitors for DLB or L-DOPA for PD.

International Patent Application Publication Nos. 2011/069951, 2012/076877, 2012/168710, 2013/175215, 2013/083994, 2013/182850, 2017/103604, 2018/020263 and 2018/109484 disclose compounds which are modulators of Kv3.1 and Kv3.2. Further, the utility of such compounds is demonstrated in animal models of seizure, hyperactivity, sleep disorders, psychosis, hearing disorders and bipolar disorders.

International Patent Application Publication No. 2013/182851 discloses modulation of Kv3.3 channels by certain compounds.

International Patent Application Publication No. 2013/175211 discloses that modulation of Kv3.1, Kv3.2 and/or Kv3.3 channels has been found to be beneficial in preventing or limiting the establishment of a permanent hearing loss resulting from acute noise exposure. The benefits of such prevention may be observed even after administration of the Kv3.1, Kv3.2 and/or Kv3.3 modulator has ceased.

International Patent Application Publication No. 2017/098254 discloses that modulation of Kv3.1, Kv3.2 and/or Kv3.3 channels has been found to be beneficial in the prophylaxis or treatment of pain, in particular neuropathic or inflammatory pain.

International Patent Application Publication No. 2019/222816 discloses 'meta-linked' pyridinyl compounds of the general formula:

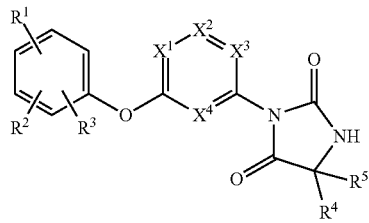

which are said to be modulators of Kv3.1 and/or Kv3.2 channels.

International Patent Application Publication No. 2020/000065 discloses 'meta-linked' diazine and triazine compounds of the general formula:

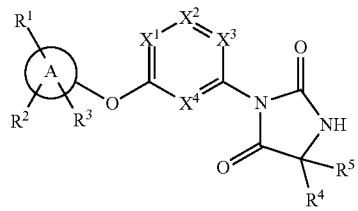

which are said to be modulators of Kv3.1 and/or Kv3.2 channels.

There remains a need for the identification of alternative modulators of Kv3.1, Kv3.2 and/or Kv3.3, in particular modulators of Kv3.1 and/or Kv3.2. Such modulators may demonstrate high in vivo potency, channel selectivity, an improved safety profile, or desirable pharmacokinetic parameters, for example high brain availability and/or low clearance rate that reduces the dose required for therapeutic effect in vivo. Alternative modulators may provide a benefit through having distinct metabolites from known modulators. Compounds which have balanced Kv3.1, Kv3.2 and/or Kv3.3 modulatory properties may be desirable e.g. compounds with modulate Kv3.1 and Kv3.2 to the same, or a similar extent. For certain therapeutic indications, there is also a need to identify compounds with a different modulatory effect on Kv3.1, Kv3.2 and/or Kv3.3 channels, for example, compounds that alter the kinetics of channel gating or channel inactivation, and which may behave in vivo as negative modulators of the channels.

BRIEF SUMMARY OF THE INVENTION

The present invention provides a compound of formula (I):

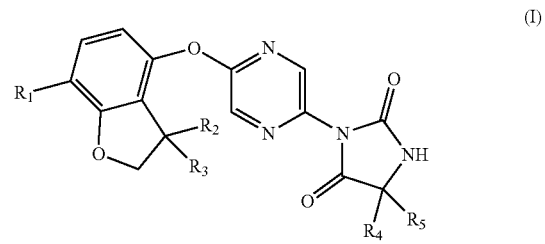

wherein:
$R_1$ is H or methyl;
$R_2$ and $R_3$ are both methyl, or $R_2$ and $R_3$, together with the carbon atom to which they are attached, are a spirocyclopropyl ring;
$R_4$ is methyl or ethyl;
$R_5$ is H or methyl;
or $R_4$ and $R_5$, together with the carbon atom to which they are attached, form a $C_3$-$C_4$ spiro carbocyclyl.

A compound of formula (I) may be provided in the form of a salt and/or solvate thereof. Suitably, the compound of formula (I) may be provided in the form of a pharmaceutically acceptable salt and/or solvate thereof and/or derivative thereof. In one embodiment of the invention a compound of formula (I) is provided in the form of a pharmaceutically acceptable salt.

The compounds of formula (I) may be used as medicaments, in particular for use in the prophylaxis or treatment of hearing disorders, including hearing loss and tinnitus, as well as schizophrenia, substance abuse disorders, pain or Fragile X syndrome.

Further, there is provided a method for the prophylaxis or treatment of hearing disorders, including hearing loss and tinnitus, as well as hearing disorders, including hearing loss and tinnitus, as well as schizophrenia, substance abuse disorders, pain or Fragile X syndrome.

Compounds of formula (I) may be used in the manufacture of a medicament for the prophylaxis or treatment of hearing disorders, including hearing loss and tinnitus, as well as schizophrenia, substance abuse disorders, pain or Fragile X syndrome.

Also provided are pharmaceutical compositions containing a compound of formula (I) and a pharmaceutically acceptable carrier or excipient.

Also provided are processes for preparing compounds of formula (I) and novel intermediates of use in the preparation of compounds of formula (I).

Additionally provided are prodrug derivatives of the compounds of formula (I).

DETAILED DESCRIPTION OF THE INVENTION

The present invention provides compounds of formula (I):

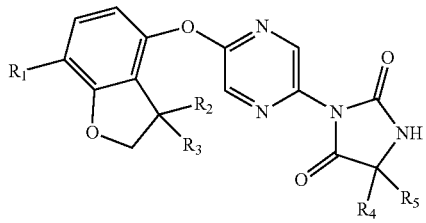

(I)

wherein:
- $R_1$ is H or methyl;
- $R_2$ and $R_3$ are both methyl, or $R_2$ and $R_3$, together with the carbon atom to which they are attached, are a spirocyclopropyl ring;
- $R_4$ is methyl or ethyl;
- $R_5$ is H or methyl;
- or $R_4$ and $R_5$, together with the carbon atom to which they are attached, form a $C_3$-$C_4$ spiro carbocyclyl;
- or a pharmaceutically acceptable salt and/or solvate and/or derivative thereof.

Embodiments set out below relating to relative stereochemistry and the nature of groups, including $R_1$, $R_2$, $R_3$, $R_4$, $R_5$, are envisaged as being independently, fully combinable with one another where appropriate to the circumstances (i.e. where chemically sensible) to form further embodiments of the invention. Such embodiments apply equally to intermediates which may be of use in the synthesis of a compound of formula (I) e.g. compounds of formulae (II), (IV), (VI), (VII) and (XVI).

Compounds of formula (I) may optionally be provided in the form of a pharmaceutically acceptable salt and/or solvate. In one embodiment of the invention a compound of formula (I) is provided in the form of a pharmaceutically acceptable salt. In a second embodiment of the invention a compound of formula (I) is provided in the form of a pharmaceutically acceptable solvate. In a third embodiment of the invention a compound of formula (I) is not in the form of a salt or solvate.

In one embodiment, $R_1$ is H. In a second embodiment $R_1$ is methyl.

In one embodiment, $R_2$ is methyl and $R_3$ is methyl. In another embodiment, $R_2$ and $R_3$ are a spiro cyclopropyl such that that the following moiety is formed:

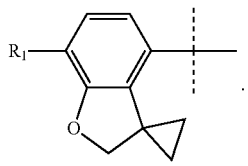

In one embodiment, $R_4$ is methyl. In a second embodiment, $R_4$ is ethyl.

In one embodiment, $R_5$ is hydrogen. In a second embodiment, $R_5$ is methyl.

In one embodiment $R_4$ and $R_5$ are the same (i.e. methyl).

In embodiments wherein $R_4$ and $R_5$ are different, they may have the following stereochemical arrangement:

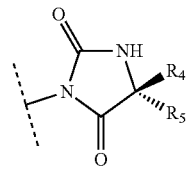

In this embodiment, for example, $R_4$ is methyl and $R_5$ is H, $R_4$ is ethyl and $R_5$ is H or $R_4$ is ethyl and $R_5$ is methyl.

In embodiments wherein $R_4$ and $R_5$ are different, they may alternatively have the following stereochemical arrangement:

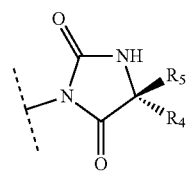

In this embodiment, for example, $R_4$ is methyl and $R_5$ is H, $R_4$ is ethyl and $R_5$ is H or $R_4$ is ethyl and $R_5$ is methyl.

In one embodiment $R_4$ and $R_5$, together with the carbon atom to which they are attached, form a spirocyclopropyl.

In another embodiment $R_4$ and $R_5$, together with the carbon atom to which they are attached, form a spirocyclobutyl.

In one embodiment, the compound of formula (I) is selected from the group consisting of:

5,5-dimethyl-3-[5-(7-methylspiro[2H-benzofuran-3,1'-cyclopropane]-4-yl)oxypyrazin-2-yl]imidazolidine-2,4-dione;

3-[5-[(3,3-dimethyl-2H-benzofuran-4-yl)oxy]pyrazin-2-yl]-5,5-dimethyl-imidazolidine-2,4-dione;

(5R)-5-ethyl-5-methyl-3-(5-spiro[2H-benzofuran-3,1'-cyclopropane]-4-yloxypyrazin-2-yl)imidazolidine-2,4-dione;

5,5-dimethyl-3-(5-spiro[2H-benzofuran-3,1'-cyclopropane]-4-yloxypyrazin-2-yl)imidazolidine-2,4-dione;

(5R)-5-ethyl-5-methyl-3-[5-(7-methylspiro[2H-benzofuran-3,1'-cyclopropane]-4-yl)oxypyrazin-2-yl]imidazolidine-2,4-dione;

(5R)-3-[5-[(3,3-dimethyl-2H-benzofuran-4-yl)oxy]pyrazin-2-yl]-5-ethyl-5-methyl-imidazolidine-2,4-dione;

5,5-dimethyl-3-[5-[(3,3,7-trimethyl-2H-benzofuran-4-yl)oxy]pyrazin-2-yl]imidazolidine-2,4-dione;

(5R)-5-ethyl-5-methyl-3-[5-[(3,3,7-trimethyl-2H-benzofuran-4-yl)oxy]pyrazin-2-yl]imidazolidine-2,4-dione;

(5R)-5-ethyl-3-[5-(7-methylspiro[2H-benzofuran-3,1'-cyclopropane]-4-yl)oxypyrazin-2-yl]imidazolidine-2,4-dione;

(5R)-5-ethyl-3-(5-spiro[2H-benzofuran-3,1'-cyclopropane]-4-yloxypyrazin-2-yl)imidazolidine-2,4-dione;

(5R)-3-[5-[(3,3-dimethyl-2H-benzofuran-4-yl)oxy]pyrazin-2-yl]-5-ethyl-imidazolidine-2,4-dione;

(5R)-5-ethyl-3-[5-[(3,3,7-trimethyl-2H-benzofuran-4-yl)oxy]pyrazin-2-yl]imidazolidine-2,4-dione;

7-[5-(7-methylspiro[2H-benzofuran-3,1'-cyclopropane]-4-yl)oxypyrazin-2-yl]-5,7-diazaspiro[3.4]octane-6,8-dione;

or a pharmaceutically acceptable salt and/or solvate thereof and/or derivative thereof.

In one embodiment, the compound of formula (I) is:
6-[5-(7-methylspiro[2H-benzofuran-3,1'-cyclopropane]-4-yl)oxypyrazin-2-yl]-4,6-diazaspiro[2.4]heptane-5,7-dione;

or a pharmaceutically acceptable salt and/or solvate thereof and/or derivative thereof.

In one embodiment, the compound of formula (I) is:
(5S)-5-ethyl-3-[5-(7-methylspiro[2H-benzofuran-3,1'-cyclopropane]-4-yl)oxypyrazin-2-yl]imidazolidine-2,4-dione;

or a pharmaceutically acceptable salt and/or solvate thereof and/or derivative thereof.

When the compound contains a $C_{1-3}$alkyl group, whether alone or forming part of a larger group, the alkyl group may be straight chain, branched or cyclic. Examples of $C_{1-3}$alkyl are methyl, ethyl, n-propyl, isopropyl and cyclopropyl. Reference to "propyl" includes n-propyl, isopropyl and cyclopropyl.

The term 'halo' or 'halogen' as used herein, refers to a fluorine, chlorine, bromine or iodine atom. Particular examples of halo are fluorine, chlorine and bromine, such as chlorine or bromine.

The term '$C_{3-4}$ spiro carbocyclyl' as used herein means a cyclic ring system containing 3 or 4 carbon atoms, namely a cyclopropyl or cyclobutyl group, wherein the cyclic ring system is attached to a secondary carbon via a spirocentre such that the secondary carbon is one of the 3 to 4 carbon atoms in the cyclic ring as follows:

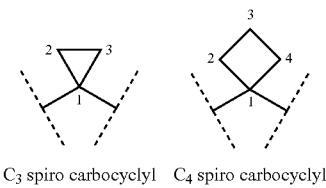

C₃ spiro carbocyclyl    C₄ spiro carbocyclyl

It will be appreciated that for use in medicine the salts of the compounds of formula (I) should be pharmaceutically acceptable. Suitable pharmaceutically acceptable salts will be apparent to those skilled in the art. Pharmaceutically acceptable salts include those described by Berge, Bighley and Monkhouse J. Pharm. Sci. (1977) 66, pp 1-19. Such pharmaceutically acceptable salts include acid addition salts formed with inorganic acids e.g. hydrochloric, hydrobromic, sulphuric, nitric or phosphoric acid and organic acids e.g. succinic, maleic, acetic, fumaric, citric, tartaric, benzoic, p-toluenesulfonic, methanesulfonic or naphthalenesulfonic acid. Non-pharmaceutically acceptable salts may be used, for example, in the isolation of compounds of formula (I) and are included within the scope of this invention.

Certain of the compounds of formula (I) may form acid addition salts with one or more equivalents of the acid. The present invention includes within its scope all possible stoichiometric and non-stoichiometric forms.

The compounds of formula (I) may be prepared in crystalline or non-crystalline form and, if crystalline, may optionally be solvated, e.g. as the hydrate. This invention includes within its scope stoichiometric solvates (e.g. hydrates) as well as compounds containing variable amounts of solvent (e.g. water).

It will be understood that the invention includes pharmaceutically acceptable derivatives of compounds of formula (I) and that these are included within the scope of the invention.

As used herein "pharmaceutically acceptable derivative" includes any pharmaceutically acceptable ester or salt of such ester of a compound of formula (I) which, upon administration to the recipient is capable of providing (directly or indirectly) a compound of formula (I) or an active metabolite or residue thereof.

A pharmaceutically acceptable prodrug may be formed by functionalising the secondary nitrogen of the hydantoin, for example with a group "L" as illustrated below (wherein $R_4$ and $R_5$ are as described above):

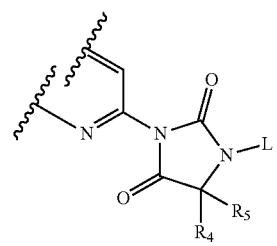

In one embodiment of the invention, a compound of formula (I) is functionalised via the secondary nitrogen of the hydantoin with a group L, wherein L is selected from:
a) —PO(OH)O⁻·M⁺, wherein M⁺ is a pharmaceutically acceptable monovalent counterion,
b) —PO(O⁻)₂·2M⁺,
c) —PO(O⁻)₂·D²⁺, wherein D²⁺ is a pharmaceutically acceptable divalent counterion,
d) —CH(R$^X$)—PO(OH)O⁻·M⁺, wherein R$^X$ is hydrogen or $C_{1-3}$ alkyl,
e) —CH(R$^X$)—PO(O⁻)₂·2M⁺,
f) —CH(R$^X$)—PO(O⁻)₂·D²⁺,
g) —SO₃⁻·M⁺,
h) —CH(R$^X$)—SO₃⁻·M⁺, and
i) —CO—CH₂CH₂—CO₂·M⁺.

It is to be understood that the present invention encompasses all isomers of formula (I) and their pharmaceutically acceptable derivatives, including all geometric, tautomeric and optical forms, and mixtures thereof (e.g. racemic mixtures). Where additional chiral centres are present in compounds of formula (I), the present invention includes within its scope all possible diastereoisomers, including mixtures thereof. The different isomeric forms may be separated or resolved one from the other by conventional methods, or any given isomer may be obtained by conventional synthetic methods or by stereospecific or asymmetric syntheses.

The present disclosure includes all isotopic forms of the compounds of the invention provided herein, whether in a form (i) wherein all atoms of a given atomic number have a mass number (or mixture of mass numbers) which predominates in nature (referred to herein as the "natural isotopic form") or (ii) wherein one or more atoms are replaced by atoms having the same atomic number, but a mass number different from the mass number of atoms which predominates in nature (referred to herein as an "unnatural variant isotopic form"). It is understood that an atom may naturally exist as a mixture of mass numbers. The term "unnatural variant isotopic form" also includes embodiments in which the proportion of an atom of given atomic number having a mass number found less commonly in nature (referred to herein as an "uncommon isotope") has been increased relative to that which is naturally occurring e.g. to the level of >20%, >50%, >75%, >90%, >95% or >99% by number of the atoms of that atomic number (the latter embodiment referred to as an "isotopically enriched variant form"). The term "unnatural variant isotopic form" also includes embodiments in which the proportion of an uncommon isotope has been reduced relative to that which is naturally occurring. Isotopic forms may include radioactive forms (i.e. they incorporate radioisotopes) and non-radioactive forms. Radioactive forms will typically be isotopically enriched variant forms.

An unnatural variant isotopic form of a compound may thus contain one or more artificial or uncommon isotopes such as deuterium ($^2$H or D), carbon-11 ($^{11}$C), carbon-13 ($^{13}$C), carbon-14 ($^{14}$C), nitrogen-13 ($^{13}$N), nitrogen-15 ($^{15}$N), oxygen-15 ($^{15}$O), oxygen-17 ($^{17}$O), oxygen-18 ($^{18}$O), phosphorus-32 ($^{32}$P), sulphur-35 ($^{35}$S), chlorine-36 ($^{36}$Cl), chlorine-37 ($^{37}$Cl), fluorine-18 ($^{18}$F) iodine-123 ($^{123}$I), iodine-125 ($^{125}$I) in one or more atoms or may contain an increased proportion of said isotopes as compared with the proportion that predominates in nature in one or more atoms.

Unnatural variant isotopic forms comprising radioisotopes may, for example, be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Unnatural variant isotopic forms which incorporate deuterium i.e. $^2$H or D may afford certain therapeutic advantages resulting from greater metabolic stability, for example, increased in vivo half-life or reduced dosage requirements, and hence may be preferred in some circumstances. Further, unnatural variant isotopic forms may be prepared which incorporate positron emitting isotopes, such as $^{11}$C, $^{18}$F, $^{15}$O and $^{13}$N, and would be useful in Positron Emission Topography (PET) studies for examining substrate receptor occupancy.

In one embodiment, the compounds of the invention are provided in a natural isotopic form.

In one embodiment, the compounds of the invention are provided in an unnatural variant isotopic form. In a specific embodiment, the unnatural variant isotopic form is a form in which deuterium (i.e. $^2$H or D) is incorporated where hydrogen is specified in the chemical structure in one or more atoms of a compound of the invention. In one embodiment, the atoms of the compounds of the invention are in an isotopic form which is not radioactive. In one embodiment, one or more atoms of the compounds of the invention are in an isotopic form which is radioactive. Suitably radioactive isotopes are stable isotopes. Suitably the unnatural variant isotopic form is a pharmaceutically acceptable form.

In one embodiment, a compound of the invention is provided whereby a single atom of the compound exists in an unnatural variant isotopic form. In another embodiment, a compound of the invention is provided whereby two or more atoms exist in an unnatural variant isotopic form.

Unnatural isotopic variant forms can generally be prepared by conventional techniques known to those skilled in the art or by processes described herein e.g. processes analogous to those described in the accompanying Examples for preparing natural isotopic forms. Thus, unnatural isotopic variant forms could be prepared by using appropriate isotopically variant (or labelled) reagents in place of the normal reagents employed in the Examples. Since the compounds of formula (I) are intended for use in pharmaceutical compositions it will readily be understood that they are each preferably provided in substantially pure form, for example at least 60% pure, more suitably at least 75% pure and preferably at least 85% pure, especially at least 98% pure (% are on a weight for weight basis). Impure preparations of the compounds may be used for preparing the more pure forms used in the pharmaceutical compositions.

Since the compounds of formula (I) are intended for use in pharmaceutical compositions it will readily be understood that they are each preferably provided in substantially pure form, for example at least 60% pure, more suitably at least 75% pure and preferably at least 85% pure, especially at least 98% pure (% are on a weight for weight basis). Impure preparations of the compounds may be used for preparing the more pure forms used in the pharmaceutical compositions.

In general, the compounds of formula (I) may be made according to the organic synthesis techniques known to those skilled in this field, as well as by the representative methods set forth below, those in the Examples and modifications thereof.

International Patent Application Publication Nos. 2011/069951, 2012/076877, 2012/168710, 2013/175215, 2013/083994, 2013/182850, 2017/103604, 2018/020263 and 2018/109484 provide methods for the synthesis of intermediates which may be of use in the production of compounds of the present invention.

General Synthesis Schemes

The following schemes detail synthetic routes to compounds of the invention and intermediates in the synthesis of such compounds. In the following schemes reactive groups can be protected with protecting groups and deprotected according to established techniques well known to the skilled person.

Compounds of formula (I), and salts and solvates thereof, may be prepared by the general methods outlined hereinafter. In the following description, the groups $R_1$, $R_2$, $R_3$, $R_4$ and $R_5$ have the meanings as previously defined for compounds of formula (I) unless otherwise stated.

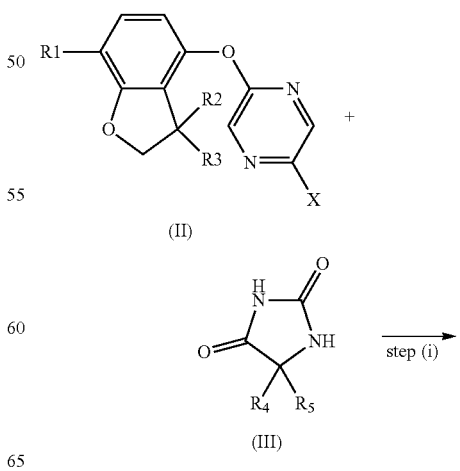

Scheme 1a

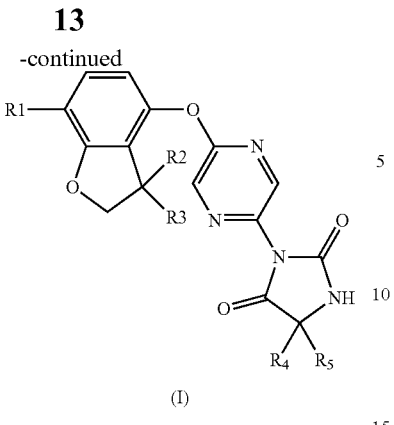

(I)

step (i): Compounds of formula (I) can be prepared by metal catalysed cross coupling reactions. In this reaction a halo-pyrazine derivative of formula (II) wherein typically X=Br and a hydantoin of formula (III) are reacted in the presence of a metal catalyst such as copper(I) oxide in a suitable solvent, e.g. in N,N-dimethylacetamide, with conventional heating or microwave heating.

Scheme 1b

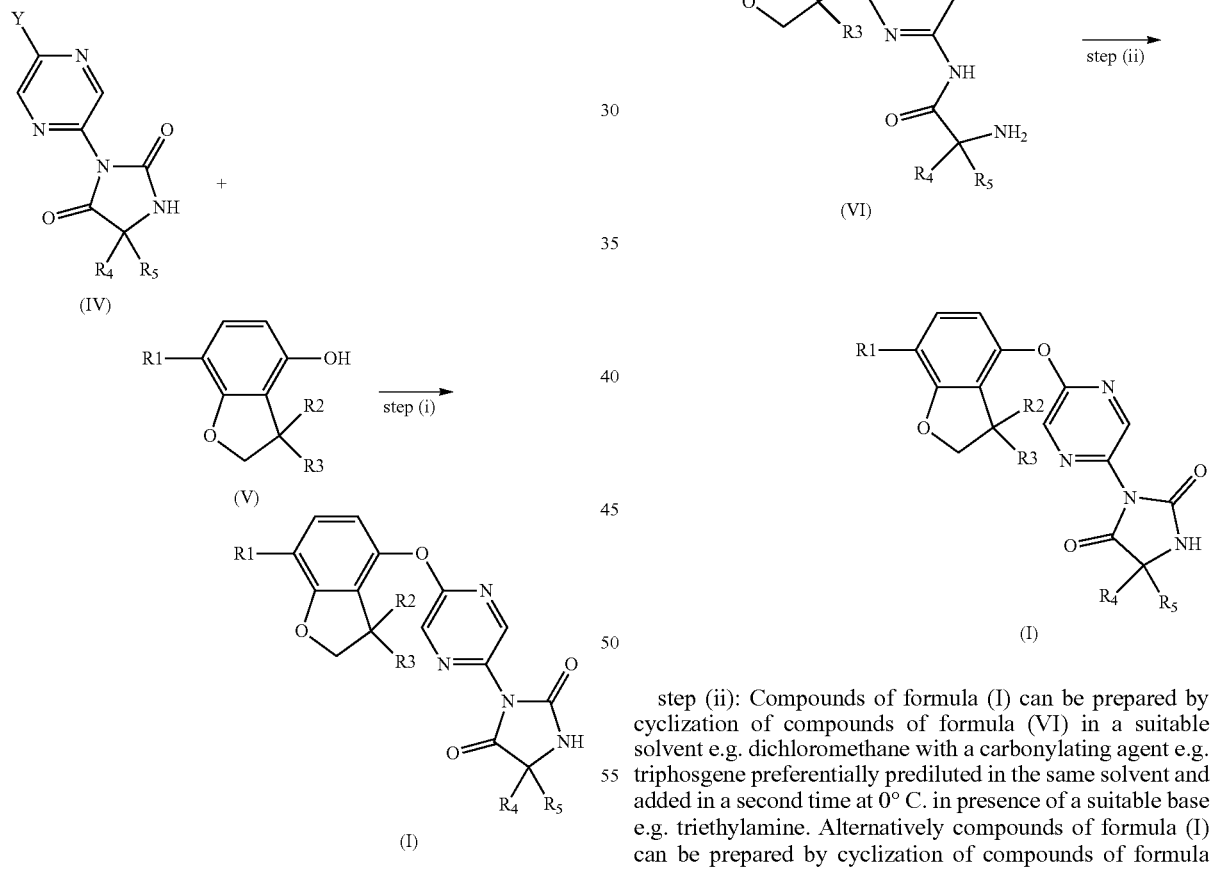

Compounds of formula (I), wherein $R_4$ and $R_5$ are not H, can be prepared by nucleophilic aromatic substitution. In this reaction a halo-pyrazine derivative of formula (IV) wherein typically Y=Cl and a phenol of formula (V) are reacted in the presence of a suitable base such as potassium carbonate in a suitable solvent, e.g. in N,N-dimethylformamide or in acetonitrile, with conventional heating or microwave heating.

Scheme 1c

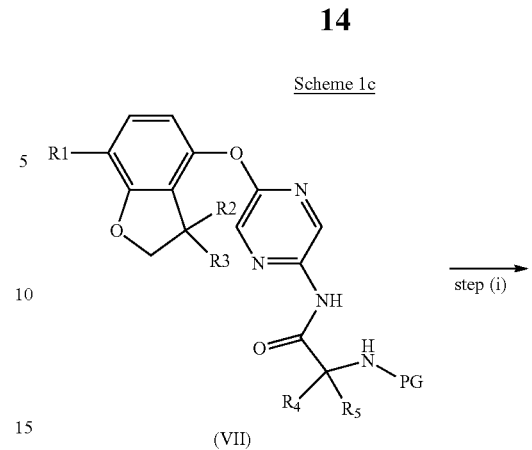

step (ii): Compounds of formula (I) can be prepared by cyclization of compounds of formula (VI) in a suitable solvent e.g. dichloromethane with a carbonylating agent e.g. triphosgene preferentially prediluted in the same solvent and added in a second time at 0° C. in presence of a suitable base e.g. triethylamine. Alternatively compounds of formula (I) can be prepared by cyclization of compounds of formula (VI) using a carbonylating agent such as carbonyldiimidazole in a suitable solvent such as ethyl acetate in presence of a base such as triethylamine or DIPEA.

step (i): Compounds of formula (VI) can be prepared by deprotection of compounds of formula (VII) wherein PG is a protecting group, suitably the protecting group is BOC, BOC may be removed in acidic conditions e.g. TFA in a suitable solvent e.g. dichloromethane at approximately 0° C. to room temperature.

Scheme 1d

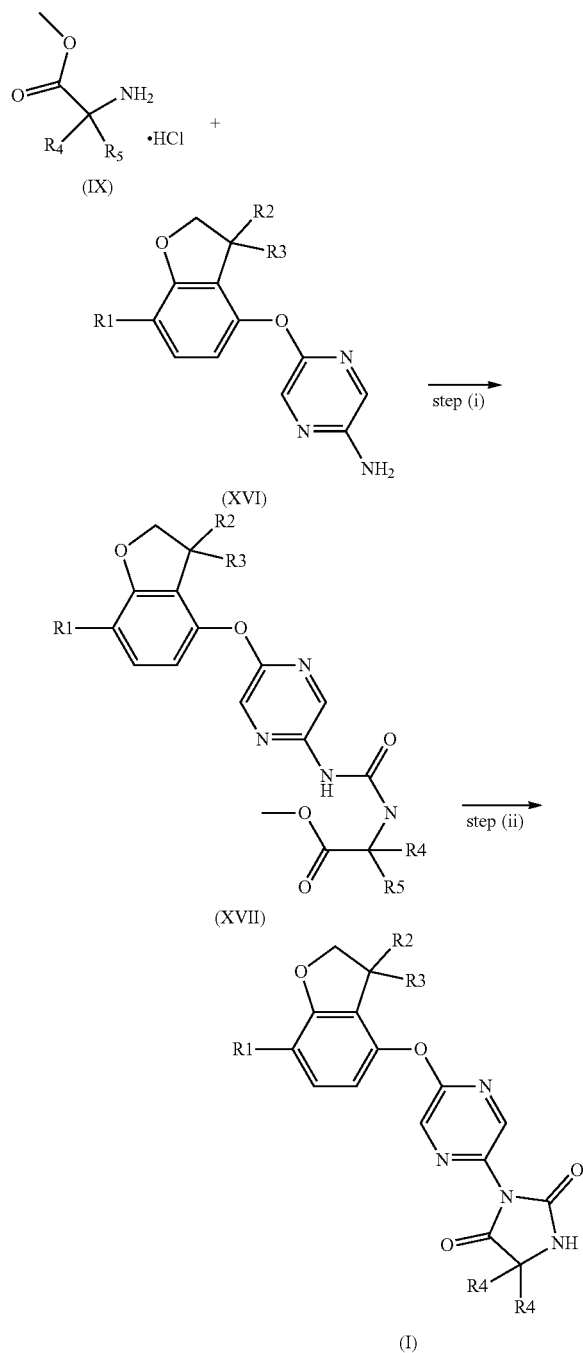

step (ii): Compounds of formula (I) can be prepared by reaction of ureas of formula (XVII) and a suitable base such as sodium methoxide in a suitable solvent such as methanol at temperature ranging from 0° C. to room temperature.

step (i): Ureas of formula (XVII) can be prepared by reaction of anilines of formula (XVI) and amino esters (such as the hydrochloride salt) of formula (IX) in a suitable solvent e.g. dichloromethane or ethyl acetate with a carbonylating agent e.g. triphosgene preferentially prediluted in the same solvent in presence of a suitable base e.g. triethylamine or diisopropylethylamine at temperature ranging from 0° C. to room temperature.

Scheme 2a

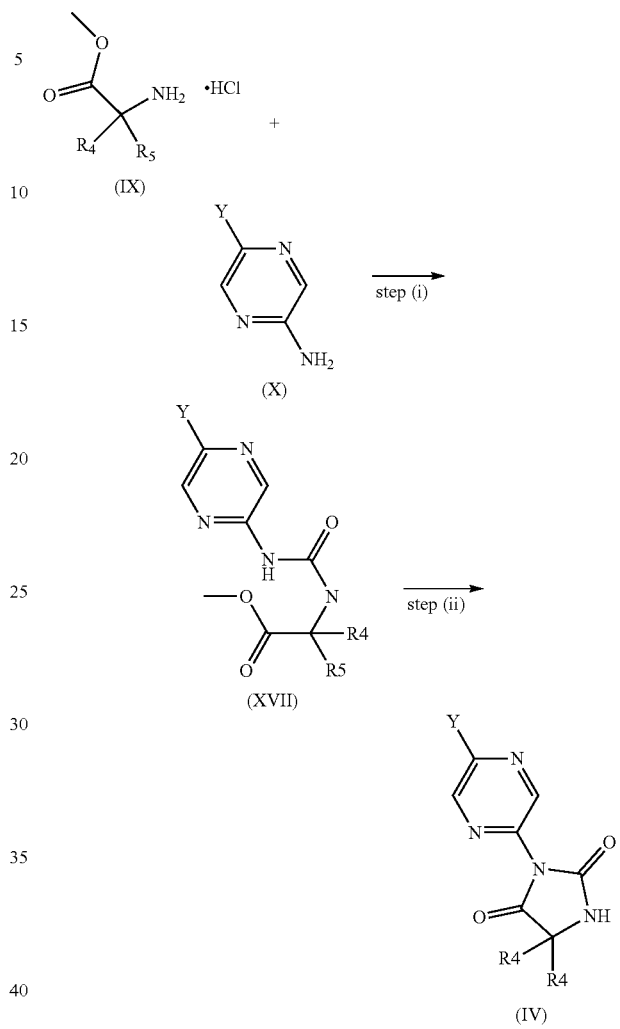

step (ii): Compounds of formula (IV) can be prepared by reaction of ureas of formula (VIII) and a suitable base such as sodium methoxide in a suitable solvent such as methanol at temperature ranging from 0° C. to room temperature.

step (i): Ureas of formula (VIII) can be prepared by reaction of commercially available halo-pyrazine derivative of formula (X), wherein typically Y=Cl, and amino esters (such as the hydrochloride salt) of formula (IX) in a suitable solvent e.g. dichloromethane or ethyl acetate with a carbonylating agent e.g. triphosgene preferentially prediluted in the same solvent in presence of a suitable base e.g. triethylamine or diisopropylethylamine at temperature ranging from 0° C. to room temperature.

Scheme 2b

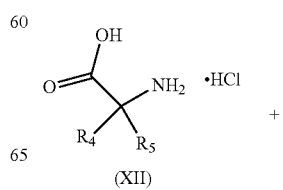

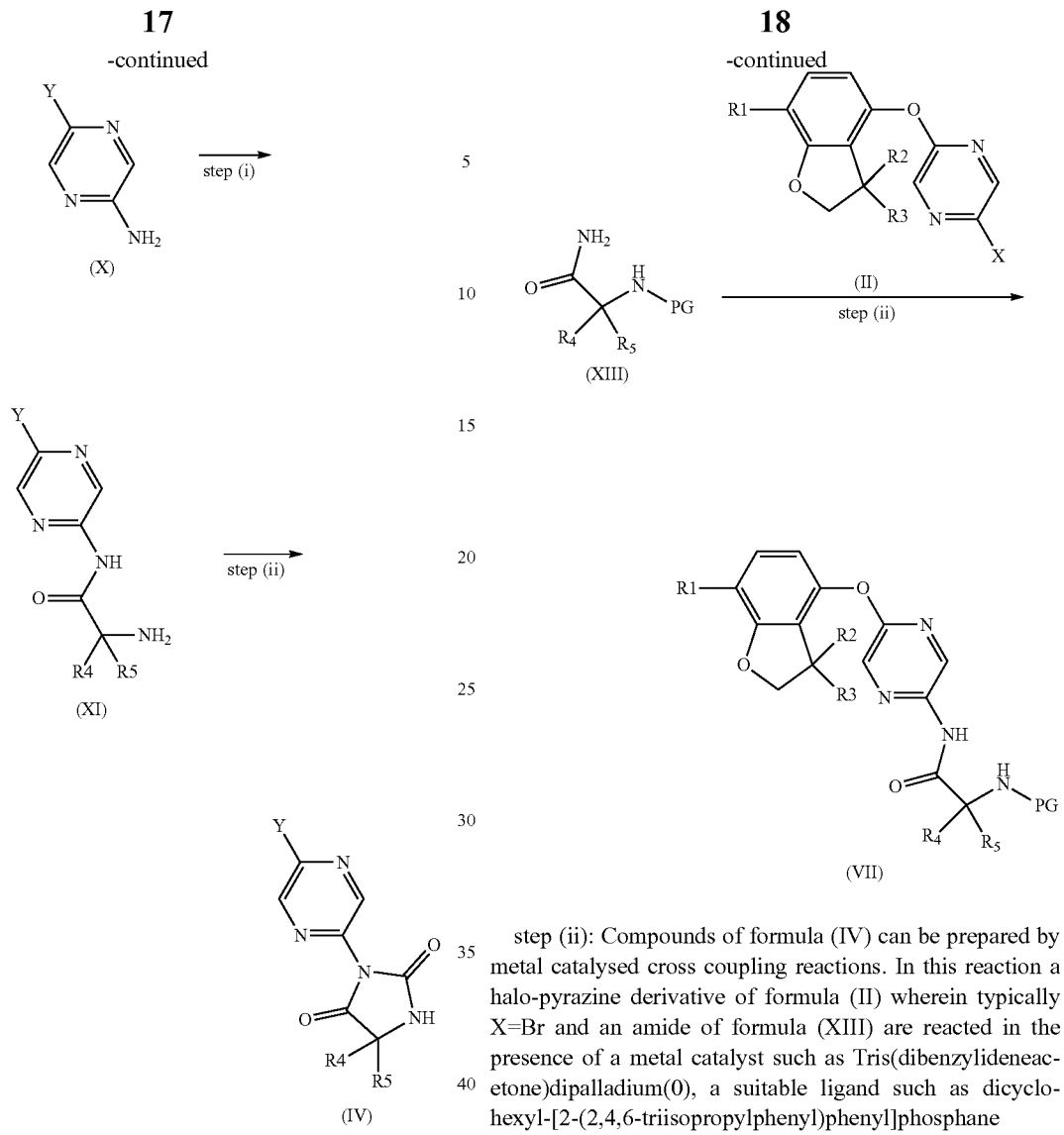

step (ii): Compounds of formula (IV) can be prepared by cyclization of compounds of formula (XI) in a suitable solvent e.g. dichloromethane with a carbonylating agent e.g. triphosgene preferentially prediluted in the same solvent and added in a second time at 0° C. in presence of a suitable base e.g. triethylamine.

step (i): Compounds of formula (XI) can be prepared from anilines of formula (X), wherein typically Y=Cl, and amino acids (as free base or hydrochloride salt) of formula (XII) by amidic coupling in the presence of a coupling agent e.g. T3P in a suitable solvent such as ethyl acetate, acetonitrile or a mixture of them.

Scheme 3

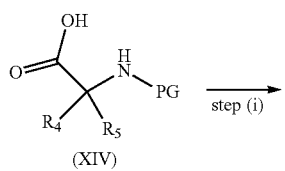

step (ii): Compounds of formula (IV) can be prepared by metal catalysed cross coupling reactions. In this reaction a halo-pyrazine derivative of formula (II) wherein typically X=Br and an amide of formula (XIII) are reacted in the presence of a metal catalyst such as Tris(dibenzylideneacetone)dipalladium(0), a suitable ligand such as dicyclohexyl-[2-(2,4,6-triisopropylphenyl)phenyl]phosphane (XPhos) and a suitable base such as cesium carbonate in a suitable solvent, e.g. in 1,4-dioxane, with conventional heating or microwave heating. Alternatively in this reaction a halo-pyrazine derivative of formula (II) wherein typically X=Br and an amide of formula (XIII) are reacted in the presence of a metal catalyst such as copper(I) iodide, a suitable ligand such as N,N'-dimethylethane-1,2-diamine and a suitable base such dipotassium carbonate in a suitable solvent, e.g. in 1-butanol, with conventional heating or microwave heating. A further alternative for the preparation of compounds of formula (IV) is to react a halo-pyrazine derivative of formula (II) wherein typically X=Br and an amide of formula (XIII) in the presence of a metal catalyst such as palladium (II) acetate, a suitable ligand such as Xantphos and a suitable base such as cesium carbonate in a suitable solvent, e.g. in 1,4-dioxane, with conventional heating or microwave heating.

step (i): Compounds of formula (XIII) can be prepared from N-protected (e.g. BOC) amino acids of formula (XIV) and an amine such as hexamethyldisilazane by amidic coupling in the presence of a base e.g. DIPEA and of a coupling agent e.g. HATU or TBTU in a solvent such as N,N-dimethylformamide.

Scheme 4

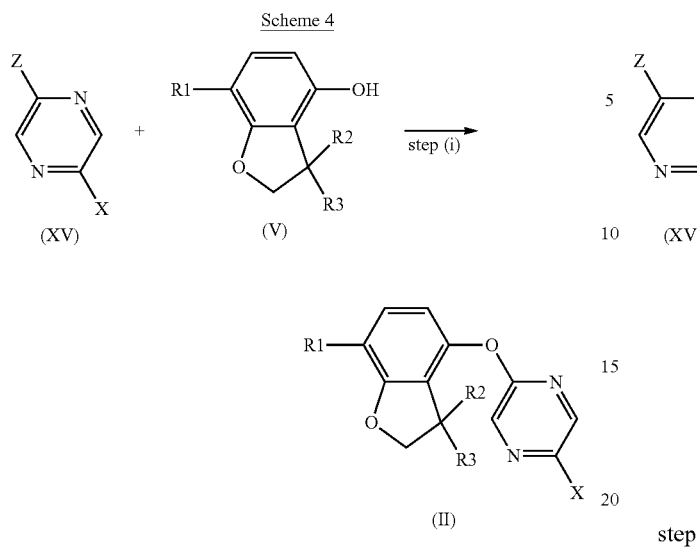

Scheme 5

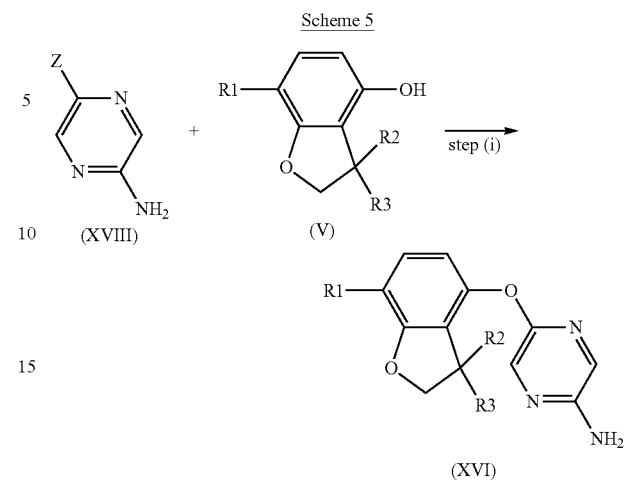

step (i): Compounds of formula (II) wherein typically X=Br can be prepared by nucleophilic aromatic substitution. In this reaction a halo-pyrazine derivative of formula (XV) wherein typically X=Z=Br and a phenol of formula (V) are reacted in the presence of a base such as potassium carbonate in a suitable solvent, e.g. in N,N-dimethylformamide, with conventional heating or microwave heating.

step (i): Anilines of formula (XVI) can be prepared by metal catalysed cross coupling reactions. In this reaction a halo-pyrazine derivative of formula (XVIII) wherein typically Z=Br and a phenol of formula (V) are reacted in the presence of a metal catalyst such as Copper(I)Iodide, a suitable ligand like picolinic acid, in a suitable solvent, e.g. in N,N-dimethylformamide or N,N-dimethylacetamide, with conventional heating or microwave heating optionally a suitable base such as potassium carbonate or caesium carbonate can be used.

Scheme 6

In Scheme 6 shown above, $PG_1$ and $PG_2$ represent suitable protecting groups. $PG_1$ in steps (i)-(iii) may be different from $PG_1$ in Steps (iv)-(vii). Suitable protecting groups include benzyl. tetrahydropyranyl or methyloxymethyl. Suitably $PG_2$ is the same as $PG_1$, e.g. both are benzyl.
Description of the Scheme Wherein $PG_1$ and $PG_2$ are Both Benzyl step (vii): Phenols of formula (V) can be prepared from the benzylated compounds of formula (XIX), by deprotection such as using a metal catalyst such as palladium on carbon and a hydrogen source such as hydrogen atmosphere or ammonium formate in a suitable solvent such as ethanol or methanol at a temperature ranging from room temperature to reflux.

step (vi): Benzylated compounds of formula (XIX) can be prepared from diols of formula (XX) using a base such as potassium tert-butoxide and a suitable solvent such as dimethyl carbonate at a temperature ranging from room temperature to reflux.

step (v): Diols of formula (XX) can be prepared from lactones of formula (XXI) using a reducing agent such as lithium aluminium hydride in a suitable solvent such as THE at a temperature ranging from 0° C. to room temperature.

step (iv): Lactones of formula (XXI) can be prepared from phenols of formula (XXII) using a benzylating agent such as benzyl bromide in presence of a base such as potassium carbonate in a suitable solvent such as acetonitrile or THE or a mixture thereof at a temperature ranging from room temperature to reflux.

step (iii): Phenols of formula (XXII) can be prepared from di-benzylated esters of formula (XXIII) wherein Rx is a suitable alkylic group such as methyl or ethyl, using a metal catalyst such as palladium on carbon and a hydrogen source such as hydrogen atmosphere or ammonium formate in a suitable solvent such as ethanol or methanol at a temperature ranging from room temperature to reflux.

step (ii): Di-benzylated esters of formula (XXIII) wherein Rx is a suitable alkylic group such as methyl or ethyl can be prepared from di-benzylated bromo derivatives of formula (XXIV) by using pre-formed organozinc derivatives of formula (XXVI) wherein Rx is a suitable alkylic group such as methyl or ethyl in presence of a metal catalyst complex such as Bis(tri-tert-butylphosphine)palladium(0) in a suitable solvent such as THE or DMF or a mixture thereof at a temperature ranging from room temperature to reflux.

step (i): Di-benzylated bromo derivatives of formula (XXIV) can be prepared from commercially available derivatives of formula (XXV) using a benzylating agent such as benzyl bromide in presence of a base such as potassium carbonate in a suitable solvent such as acetonitrile or THE or acetone or a mixture thereof at a temperature ranging from room temperature to reflux.

When $PG_1$ and/or $PG_2$ are protecting groups such as tetrahydropyranyl or methyloxymethyl, usual protection/deprotection conditions apply:

Protection conditions of phenols with tetrahydropyranyl include the reaction of a phenol with dihydro-2H-pyran in presence of a catalyst such C:Py·p-MePhSO$_3$H in a suitable solvent such us dichloromethane at a temperature ranging from 0° C. to reflux.

Cleavage conditions for a tetrahydropyranyl protecting group from phenols include the reaction of a THP protected phenol in presence of an acid such as sulphuric acid or p-MePhSO$_3$H or HCl in a suitable solvent such us methanol or ethanol at a temperature ranging from 0° C. to reflux.

Protection conditions of phenols with methyloxymethyl include the reaction of a phenol with chloromethyl methyl ether in presence of a base such us potassium carbonate in a suitable solvent such us tetrahydrofuran or acetonitrile at a temperature ranging from 0° C. to reflux.

Cleavage conditions for a methyloxymethyl protecting group from phenols include the reaction of a MOM protected phenol in presence of an acid such as sulphuric acid or p-MePhSO$_3$H or HCl in a suitable solvent such us methanol or ethanol at a temperature ranging from 0° C. to reflux.

Scheme 7

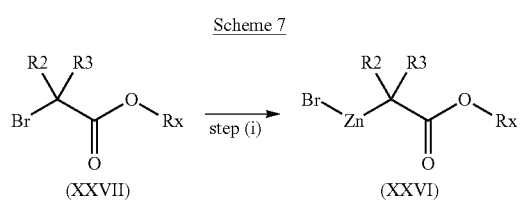

Step (i): Organozinc derivatives of formula (XXVI) wherein Rx is a suitable alkylic group such as methyl or ethyl can be prepared by adding commercially available bromo esters of formula (XXVII) to a refluxing suspension of zinc (0) in presence of 1,2-dibromoethane and chlorotrimethylsilane in a suitable solvent such as THF.

Processes of the Invention

According to further aspects of the present invention are provided processes for the preparation of compounds of formula (I) and derivatives thereof, as well as processes for preparing intermediates in the synthesis of compounds of formula (I).

The processes of the invention are described above and include any individual step of a multi-step scheme.

Intermediates

The present invention also relates to novel intermediates in the synthesis of compounds of formula (I). Such novel intermediates include compounds of formulae (II), (IV), (VI), (VII), (VIII), (XI), (XVI) and (XVII). Also of interest are intermediates of formulae (XIX) to (XXIV). Salts, such as pharmaceutically acceptable salts, of such intermediates are also provided by the present invention.

Intermediates of the invention therefore include:

compounds of formula (II):

wherein $R_1$, $R_2$ and $R_3$ are as defined previously, X is halo, such as Br;

compounds of formula (IV):

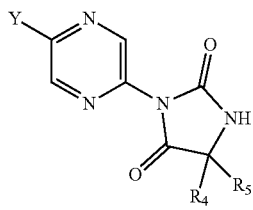

wherein $R_1$, $R_2$ and $R_3$ are as defined previously, Y is halo, such as Cl;

compounds of formula (VI):

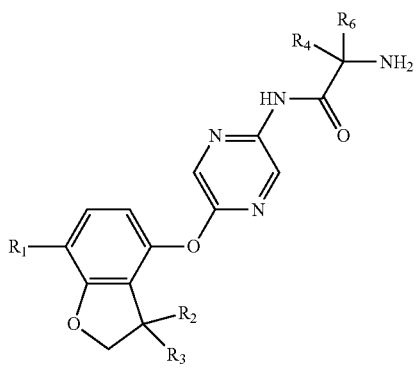

wherein $R_1$, $R_2$, $R_3$, $R_4$ and $R_5$ are as defined previously;

compounds of formula (VII):

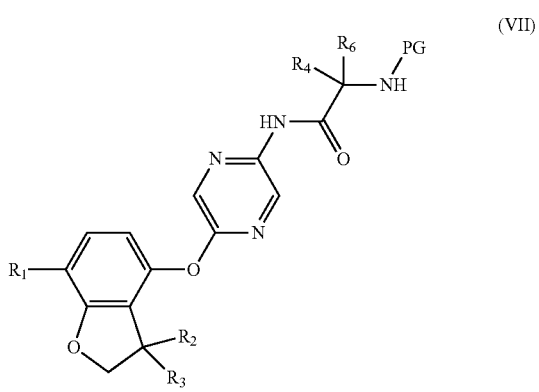

wherein $R_1$, $R_2$, $R_3$, $R_4$ and $R_5$ are as defined previously, PG is a suitable protecting group such as BOC;

compounds of formula (XVI):

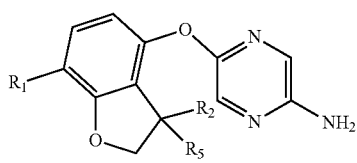

wherein $R_1$, $R_2$ and $R_3$ are as defined previously.

Kv3.1, Kv3.2 and/or Kv3.3 Modulation

Compounds of formula (I) of the present invention are modulators of Kv3.1. Compounds of formula (I) may also be modulators of Kv3.2 and/or Kv3.3. Compounds of the invention may be tested in the assay of Biological Example 1 to determine their modulatory properties for Kv3.1 and/or Kv3.2 and/or Kv3.3 channels.

A 'modulator' as used herein refers to a compound which is capable of producing at least 10% potentiation, and suitably at least 20% potentiation of whole-cell currents mediated by human Kv3.1 and/or human Kv3.2 and/or human Kv3.3 channels recombinantly expressed in mammalian cells.

The term 'Kv3.1, Kv3.2 and/or Kv3.3' shall be taken to mean the same as 'Kv3.1 and/or Kv3.2 and/or Kv3.3' and may also be referred to as 'Kv3.1/Kv3.2/Kv3.3'.

In one embodiment the modulator is capable of producing at least 10% potentiation and suitably at least 20% potentiation of whole-cell currents mediated by human Kv3.1 channels recombinantly expressed in mammalian cells. Suitably the $pEC_{50}$ of the modulator is in the range of 4-7 (such as 5-6.5).

In one embodiment the modulator is capable of producing at least 10% potentiation and suitably at least 20% potentiation of whole-cell currents mediated by human Kv3.2 channels recombinantly expressed in mammalian cells. Suitably the $pEC_{50}$ of the modulator is in the range of 4-7 (such as 5-6.5).

In one embodiment the modulator is capable of producing at least 10% potentiation and suitably at least 20% potentiation of whole-cell currents mediated by human Kv3.3 channels recombinantly expressed in mammalian cells. Suitably the $pEC_{50}$ of the modulator is in the range of 4-7 (such as 5-6.5).

In another embodiment the modulator is capable of producing at least 10% potentiation and suitably at least 20% potentiation of whole-cell currents mediated by human Kv3.1 and Kv3.2 channels recombinantly expressed in mammalian cells.

In another embodiment the modulator is capable of producing at least 10% potentiation and suitably at least 20% potentiation of whole-cell currents mediated by human Kv3.1 and Kv3.3 channels recombinantly expressed in mammalian cells.

In another embodiment the modulator is capable of producing at least 10% potentiation and suitably at least 20% potentiation of whole-cell currents mediated by human Kv3.2 and Kv3.3 channels recombinantly expressed in mammalian cells.

In a further embodiment the modulator is capable of producing at least 10% potentiation and suitably at least 20% potentiation of whole-cell currents mediated by human Kv3.1, Kv3.2 and Kv3.3 channels recombinantly expressed in mammalian cells.

The compounds of formula (I) or their pharmaceutically acceptable salts and/or solvates and/or derivatives may be of use for the treatment or prophylaxis of a disease or disorder where a modulator of the Kv3.1 or Kv3.2 or Kv3.1 and Kv3.2 channels is required. As used herein, a modulator of Kv3.1 or Kv3.2 or Kv3.1 and Kv3.2 is a compound which alters the properties of these channels, either positively or negatively. In a particular aspect of the invention, the compound of formula (I) is a positive modulator. Compounds of the invention may be tested in the assay of Biological Example 1 to determine their modulatory properties.

In one embodiment of the invention the compounds of formula (I) or their pharmaceutically acceptable salts and/or solvates and/or derivatives thereof are selective for modulation of Kv3.1 channels over modulation of Kv3.2 channels. By selective, is meant that compounds demonstrate, for example, at least a 2 fold, 5 fold or 10 fold activity for Kv3.1 channels than for Kv3.2 channels. The activity of a compound is suitably quantified by its potency as indicated by an Ec50 value.

In another embodiment of the invention, the compounds of formula (I) or their pharmaceutically acceptable salts and/or solvates and/or derivatives thereof are selective for modulation of Kv3.2 channels over modulation of Kv3.1 channels. Once again, by selective is meant that compounds demonstrate, for example at least a 2 fold, 5 fold or 10 fold activity for Kv3.2 channels than for Kv3.1 channels.

In a particular embodiment of the invention the compounds of formula (I) or their pharmaceutically acceptable salts and/or solvates and/or derivatives thereof demonstrate comparable activity between modulation of Kv3.1 and Kv3.2 channels, for example the activity for one channel is less than 2 fold that for the other channel, such as less than 1.5 fold or less than 1.2 fold.

In certain disorders it may be of benefit to utilise a modulator of Kv3.3 or Kv3.1, or Kv3.3 and Kv3.1 which demonstrates a particular selectivity profile between the two channels. For example a compound may be selective for modulation of Kv3.3 channels over modulation of Kv3.1 channels demonstrating, for example, at least a 2 fold, 5 fold or 10 fold activity for Kv3.3 channels than for Kv3.1 channels.

In another embodiment of the invention, the compounds of formula (I) or their pharmaceutically acceptable salts and/or solvates and/or derivatives thereof are selective for modulation of Kv3.1 channels over modulation of Kv3.3 channels. Once again, by selective is meant that compounds demonstrate, for example at least a 2 fold, 5 fold or 10 fold activity for Kv3.1 channels than for Kv3.3 channels.

In a particular embodiment of the invention, a compound may demonstrate comparable activity between modulation of Kv3.3 and Kv3.1 channels, for example the activity for each channel is less than 2 fold that for the other channel, such as less than 1.5 fold or less than 1.2 fold.

In certain disorders it may be of benefit to utilise a modulator of Kv3.3 or Kv3.2, or Kv3.3 and Kv3.2 which demonstrates a particular selectivity profile between the two channels. A compound may be selective for modulation of Kv3.3 channels over modulation of Kv3.2 channels demonstrating, for example, at least a 2 fold, 5 fold or 10 fold activity for Kv3.3 channels than for Kv3.2 channels.

In another embodiment of the invention, the compounds of formula (I) or their pharmaceutically acceptable salts and/or solvates and/or derivatives thereof are selective for modulation of Kv3.2 channels over modulation of Kv3.3 channels. Once again, by selective is meant that compounds demonstrate, for example at least a 2 fold, 5 fold or 10 fold activity for Kv3.2 channels than for Kv3.3 channels.

In another particular embodiment a compound may demonstrate comparable activity between modulation of Kv3.3 and Kv3.2 channels, for example the activity for each channel is less than 2 fold that for the other channel, such as less than 1.5 fold or less than 1.2 fold.

In a yet further particular embodiment of the invention a compound may demonstrate comparable activity between modulation of Kv3.3, Kv3.2 and Kv3.1 channels, for example the activity for each channel is less than 2 fold that for any other channel, such as less than 1.5 fold or less than 1.2 fold. The activity of a compound is suitably quantified by its potency as indicated by an EC50 value.

Therapeutic Methods

The invention also provides a compound of formula (I), or a pharmaceutically acceptable salt and/or solvate (e.g. salt) and/or derivative thereof, for use in the treatment or prophylaxis of a disease or disorder where a modulator of Kv3.1, Kv3.2 and/or Kv3.3 is required, for example those diseases and disorders mentioned herein below.

The invention provides a method of treating or preventing a disease or disorder where a modulator of Kv3.1, Kv3.2 and/or Kv3.3 is required, for example those diseases and disorders mentioned herein below, which comprises administering to a subject in need thereof an effective amount of a compound of formula (I) or a pharmaceutically acceptable salt and/or solvate (e.g. salt) and/or derivative thereof.

The invention also provides the use of a compound of formula (I), or a pharmaceutically acceptable salt and/or solvate thereof (e.g. salt) and/or derivative, in the manufacture of a medicament for the treatment or prophylaxis of a disease or disorder where a modulator of Kv3.1, Kv3.2 and/or Kv3.3 is required, for example those diseases and disorders mentioned herein below.

In one embodiment is provided a compound of formula (I) or a pharmaceutically acceptable salt and/or solvate thereof and/or derivative thereof for use as a medicament.

The term "treatment" or "treating" as used herein includes the control, mitigation, reduction, or modulation of the disease state or its symptoms.

The term "prophylaxis" is used herein to mean preventing symptoms of a disease or disorder in a subject or preventing recurrence of symptoms of a disease or disorder in an afflicted subject and is not limited to complete prevention of an affliction.

Suitably the subject is a human.

Diseases or disorders that may be mediated by modulation of Kv3.1 and/or Kv3.2 channels may be selected from the list below. The numbers in brackets after the listed diseases below refer to the classification code in Diagnostic and Statistical Manual of Mental Disorders, 4th Edition, published by the American Psychiatric Association (DSM-IV) and/or the International Classification of Diseases, 10th Edition (ICD-10).

In one embodiment of the invention, the compounds of formula (I) or their pharmaceutically acceptable salts and/or solvates and/or derivatives may be of use for the treatment or prophylaxis of a disease or disorder selected from the group consisting of hearing disorders, schizophrenia, depression and mood disorders, bipolar disorder, substance abuse disorders, anxiety disorders, sleep disorders, hyperacusis and disturbances of loudness perception, Mèniére's disease, disorders of balance, and disorders of the inner ear, impulse control disorder, personality disorders, attention-deficit/hyperactivity disorder, autism spectrum disorders, eating disorders, cognition impairment, ataxia, pain such as neuropathic pain, inflammatory pain and miscellaneous pain, Lewy body dementia and Parkinson's disease.

In one embodiment of the invention, the compounds of formula (I) or their pharmaceutically acceptable salts and/or solvates and/or derivatives may be of use for the treatment or prophylaxis of a disease or disorder selected from the group consisting of hearing disorders including hearing loss and tinnitus, schizophrenia, substance abuse disorders, pain such as neuropathic pain, inflammatory pain and miscellaneous pain, Lewy body dementia and Parkinson's disease.

In one embodiment of the invention, the compounds of formula (I) or their pharmaceutically acceptable salts and/or solvates and/or derivatives may be of use for the treatment or prophylaxis of a disease or disorder selected from the group consisting of Fragile-X, Rett's Disorder and Alzheimer's disease.

The invention provides a method for the prophylaxis or treatment of a disease or disorder selected from the group consisting of hearing disorders, schizophrenia, depression and mood disorders, bipolar disorder, substance abuse disorders, anxiety disorders, sleep disorders, hyperacusis and disturbances of loudness perception, Mèniére's disease, disorders of balance, and disorders of the inner ear, impulse control disorder, personality disorders, attention-deficit/hyperactivity disorder, autism spectrum disorders, eating disorders, cognition impairment, ataxia, pain such as neuropathic pain, inflammatory pain and miscellaneous pain, Lewy body dementia and Parkinson's disease, which comprises administering to a subject in need thereof an effective amount of a compound of formula (I) or a pharmaceutically acceptable salt and/or solvate (e.g. salt) and/or derivative thereof.

The invention also provides the use of a compound of formula (I), or a pharmaceutically acceptable salt and/or solvate thereof (e.g. salt) and/or derivative thereof, in the manufacture of a medicament for the treatment or prophylaxis of a disease or disorder selected from the group consisting of hearing disorders, schizophrenia, depression and mood disorders, bipolar disorder, substance abuse disorders, anxiety disorders, sleep disorders, hyperacusis and disturbances of loudness perception, Mèniére's disease, disorders of balance, and disorders of the inner ear, impulse control disorder, personality disorders, attention-deficit/hyperactivity disorder, autism spectrum disorders, eating disorders, cognition impairment, ataxia, pain such as neuropathic pain, inflammatory pain and miscellaneous pain, Lewy body dementia and Parkinson's disease.

In a particular embodiment of the invention, there is provided a compound of formula (I) or their pharmaceutically acceptable salts and/or solvates (e.g. salts) and/or derivatives thereof for use in the treatment of prophylaxis of hearing disorders. Hearing disorders include auditory neuropathy, auditory processing disorder, hearing loss, which includes sudden hearing loss, noise induced hearing loss, substance-induced hearing loss, and hearing loss in adults over 60, over 65, over 70 or over 75 years of age (presbycusis), and tinnitus.

The compounds of formula (I) or their pharmaceutically acceptable salts and/or solvates (e.g. salts) and/or derivatives thereof may be of use for the treatment or prophylaxis of Mèniére's disease, disorders of balance, and disorders of the inner ear.

In a particular embodiment of the invention, there is provided a compound of formula (I) or their pharmaceutically acceptable salts and/or solvates (e.g. salts) and/or derivatives thereof for use in the treatment or prophylaxis of schizophrenia. Schizophrenia includes the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

The compounds of formula (I) or their pharmaceutically acceptable salts and/or solvates (e.g. salts) and/or derivatives thereof may be of use for the treatment or prophylaxis of depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90); Seasonal affective disorder.

The compounds of formula (I) or their pharmaceutically acceptable salts and/or solvates (e.g. salts) and/or derivatives thereof may be of use for the treatment or prophylaxis of Epilepsy, (including, but not limited to, localization-related epilepsies, generalized epilepsies, epilepsies with both generalized and local seizures, and the like), seizures associated with Lennox-Gastaut syndrome, seizures as a complication of a disease or condition (such as seizures associated with encephalopathy, phenylketonuria, juvenile Gaucher's disease, Lundborg's progressive myoclonic epilepsy, stroke, head trauma, stress, hormonal changes, drug use or withdrawal, alcohol use or withdrawal, sleep deprivation, fever, infection, and the like), essential tremor, restless limb syndrome, partial and generalised seizures (including tonic, clonic, tonic-clonic, atonic, myoclonic, absence seizures), secondarily generalized seizures, temporal lobe epilepsy, absence epilepsies (including childhood, juvenile, myoclonic, photo- and pattern-induced), severe epileptic encephalopathies (including hypoxia-related and Rasmussen's syndrome), febrile convulsions, epilepsy partialis continua, progressive myoclonus epilepsies (including Unverricht-Lundborg disease and Lafora's disease), post-traumatic seizures/epilepsy including those related to head injury, simple reflex epilepsies (including photosensitive, somatosensory and proprioceptive, audiogenic and vestibular), metabolic disorders commonly associated with epilepsy such as pyridoxine-dependent epilepsy, Menkes' kinky hair disease, Krabbe's disease, epilepsy due to alcohol and drug abuse (e.g. cocaine), cortical malformations associated with epilepsy (e.g. double cortex syndrome or subcortical band heterotopia), chromosomal anomalies associated with seizures or epilepsy such as Partial monosomy (15Q)/Angelman syndrome).

The compounds of formula (I) or their pharmaceutically acceptable salts and/or solvates (e.g. salts) and/or derivatives thereof may be of use for the treatment or prophylaxis of substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide.

The compounds of formula (I) or their pharmaceutically acceptable salts and/or solvates (e.g. salts) and/or derivatives thereof may be of use for the treatment or prophylaxis of anxiety disorders including Panic Attack; Panic Disorder including Panic Disorder without Agoraphobia (300.01) and Panic Disorder with Agoraphobia (300.21); Agoraphobia; Agoraphobia Without History of Panic Disorder (300.22), Specific Phobia (300.29, formerly Simple Phobia) including the subtypes Animal Type, Natural Environment Type, Blood-Injection-Injury Type, Situational Type and Other Type), Social Phobia (Social Anxiety Disorder, 300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-Induced Anxiety Disorder, Separation Anxiety Disorder (309.21), Adjustment Disorders with Anxiety (309.24) and Anxiety Disorder Not Otherwise Specified (300.00).

The compounds of formula (I) or their pharmaceutically acceptable salts and/or solvates (e.g. salts) and/or derivatives thereof may be of use for the treatment or prophylaxis of sleep disorders including primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition, in particular sleep disturbances associated with such diseases as neurological disorders, neuropathic pain, restless leg syndrome, heart and lung diseases; and Substance-Induced Sleep Disorder including the subtypes Insomnia Type, Hypersomnia Type, Parasomnia Type and Mixed Type; sleep apnea and jet-lag syndrome.

The compounds of formula (I) or their pharmaceutically acceptable salts and/or solvates (e.g. salts) and/or derivatives thereof may be of use for the treatment or prophylaxis of hyperacusis and disturbances of loudness perception, including Fragile-X syndrome and autism.

The compounds of formula (I) or their pharmaceutically acceptable salts and/or solvates (e.g. salts) and/or derivatives thereof may be of use for the treatment or prophylaxis of Impulse control disorder including: Intermittent Explosive Disorder (312.34), Kleptomania (312.32), Pathological Gambling (312.31), Pyromania (312.33), Trichotillomania (312.39), Impulse-Control Disorders Not Otherwise Specified (312.3), Binge Eating, Compulsive Buying, Compulsive Sexual Behaviour and Compulsive Hoarding.

The compounds of formula (I) or their pharmaceutically acceptable salts and/or solvates (e.g. salts) and/or derivatives thereof may be of use for the treatment or prophylaxis of Sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73), Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9).

The compounds of formula (I) or their pharmaceutically acceptable salts and/or solvates (e.g. salts) and/or derivatives thereof may be of use for the treatment or prophylaxis of Personality Disorders including the subtypes Paranoid Personality Disorder (301.0), Schizoid Personality Disorder (301.20), Schizotypal Personality Disorder (301,22), Antisocial Personality Disorder (301.7), Borderline Personality Disorder (301,83), Histrionic Personality Disorder (301.50), Narcissistic Personality Disorder (301,81), Avoidant Personality Disorder (301.82), Dependent Personality Disorder (301.6), Obsessive-Compulsive Personality Disorder (301.4) and Personality Disorder Not Otherwise Specified (301.9).

The compounds of formula (I) or their pharmaceutically acceptable salts and/or solvates (e.g. salts) and/or derivatives thereof may be of use for the treatment or prophylaxis of Attention-Deficit/Hyperactivity Disorder including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23).

The compounds of formula (I) or their pharmaceutically acceptable salts and/or solvates (e.g. salts) and/or derivatives thereof may be of use for the treatment or prophylaxis of Autism Spectrum Disorders including Autistic Disorder (299.00), Asperger's Disorder (299.80), Rett's Disorder (299.80), Childhood Disintegrative Disorder (299.10) and Pervasive Disorder Not Otherwise Specified (299.80, including Atypical Autism).

The compounds of formula (I) or their pharmaceutically acceptable salts and/or solvates (e.g. salts) and/or derivatives thereof may be of use for the treatment or prophylaxis of eating disorders such as Anorexia Nervosa (307.1) including the subtypes Restricting Type and Binge-Eating/Purging Type; Bulimia Nervosa (307.51) including the subtypes Purging Type and Nonpurging Type; Obesity; Compulsive Eating Disorder; Binge Eating Disorder; and Eating Disorder Not Otherwise Specified (307.50).

The compounds of formula (I) or their pharmaceutically acceptable salts and/or solvates (e.g. salts) and/or derivatives thereof may be of use for the enhancement of cognition including the treatment of cognition impairment in other diseases such as schizophrenia, bipolar disorder, depression, other psychiatric disorders and psychotic conditions associated with cognitive impairment, e.g. Alzheimer's disease. Alternatively, the compounds of formula (I) or their pharmaceutically acceptable salts and/or solvates thereof may be of use for the prophylaxis of cognition impairment, such as may be associated with in diseases such as schizophrenia, bipolar disorder, depression, other psychiatric disorders and psychotic conditions associated with cognitive impairment, e.g. Alzheimer's disease.

The compounds of formula (I) or their pharmaceutically acceptable salts and/or solvates (e.g. salts) and/or derivatives thereof may be of use for the treatment or prophylaxis of ataxia including ataxia, in particular spinocerebellar ataxia, especially ataxia associated with R420H, R423H or F448L mutations.

The compounds of formula (I) or their pharmaceutically acceptable salts and/or solvates (e.g. salts) and/or derivatives thereof may be of use for the treatment or prophylaxis of pain including nociceptive, neuropathic, inflammatory or miscellaneous pain.

Nociceptive pain represents the normal response to noxious insult or injury of tissues such as skin, muscles, visceral organs, joints, tendons, or bones. Examples of nociceptive pain which form part of the invention include somatic pain: musculoskeletal (joint pain, myofascial pain) or cutaneous, which is often well localized; or visceral pain: hollow organs or smooth muscle.

Neuropathic pain is pain initiated or caused by a primary lesion or disease in the somatosensory nervous system. Sensory abnormalities range from deficits perceived as paraesthesia (numbness) to hypersensitivity (hyperalgesia or allodynia), and dysaesthesia (tingling and other sensations). Examples of neuropathic pain which form part of the invention include, but are not limited to, diabetic neuropathy, post-herpetic neuralgia, spinal cord injury pain, phantom limb (post-amputation) pain, and post-stroke central pain. Other causes of neuropathic pain include trauma, chemotherapy and heavy metal exposure.

Inflammatory pain occurs as a result of activation and sensitization of the nociceptive pain pathway by a variety of mediators released at a site of tissue inflammation. Mediators that have been implicated as key players in inflammatory pain are pro-inflammatory cytokines such IL-1-alpha, IL-1-beta, IL-6 and TNF-alpha, chemokines, reactive oxygen species, vasoactive amines, lipids, ATP, acid, and other factors released by infiltrating leukocytes, vascular endothelial cells, or tissue resident mast cells. Examples causes of inflammatory pain which form part of the invention include appendicitis, rheumatoid arthritis, inflammatory bowel disease, and herpes zoster.

Miscellaneous pain refers to pain conditions or disorders which are not easily classifiable. The current understanding of their underlying mechanisms is still rudimentary though specific therapies for those disorders are well known; they include cancer pain, migraine and other primary headaches and wide-spread pain of the fibromyalgia type.

Suitably, specific pain indications that may be mediated by a modulator of Kv3.1 and/or Kv3.2 and/or Kv3.3 channels are neuropathic pain and/or inflammatory pain.

Pain is a subjective condition and in a clinical setting tends to be measured by a patient's self-assessment. Therefore it can be difficult to measure and quantify pain threshold. For chronic pain, typically a subjective 11-point rating scale is used where 0 is no pain and 10 is the worst pain imaginable. Subjects generally record their worst pain over a given period, usually a day. A minimum mean baseline score is also recorded and response to the medication is measured relative to the baseline, for example, a reduction of at least 10%, 20%, 30%, 40% or 50% in pain from the baseline score may be observed.

Since individual responses to medicaments may vary, not all individuals may experience a reduction in pain from the baseline score. Consequently, suitably a reduction is observed in at least at least 10%, 20%, 30%, 40%, 50%, 60%, 70%, 80%, 90% or all individuals tested.

Therefore, in one embodiment of the invention, a reduction of at least 10%, 20%, 30%, 40% or 50% in pain from the baseline score is observed upon administration of a Kv3.1/Kv3.2/Kv3.3 modulator, such as a compound of formula (I) or a pharmaceutically acceptable salt, solvate and/or derivative thereof to a subject in need thereof.

Administration of a Kv3.1/Kv3.2/Kv3.3 modulator can occur before an anticipated onset of pain or after the onset of pain. In cases where it is anticipated that development of a disease or disorder may lead to an increase in pain experienced by the subject, a Kv3.1/Kv3.2/Kv3.3 modulator, such as a compound of formula (I) or a pharmaceutically acceptable salt, solvate and/or derivative thereof can be administered. In cases where a subject is already experiencing pain, a Kv3.1/Kv3.2/Kv3.3 modulator, such as a compound of formula (I) or a pharmaceutically acceptable salt, solvate and/or derivative thereof may be administered to a subject in need thereof.

Treatment of the subject in need thereof may continue for as long as treatment is required, for example, 1 day, 1 week, 2 weeks, 3 weeks, 1 month, 6 months, 1 year, more than 1 year more than 2 years, more than 5 years or more than 10 years. Therefore in one embodiment of the invention, a therapeutically effective amount of a Kv3.1/Kv3.2/Kv3.3 modulator, such as a compound of formula (I) or a pharmaceutically acceptable salt, solvate and/or derivative thereof, is administered to a subject in need thereof for 1 day to 1 month, 1 week to 3 months, 1 month to 6 months, 3 months to 1 year or more than 1 year.

Reduction in pain in a subject can be measured by assessing the response to an external stimuli such as mechanical or thermal (e.g. cold) stimuli (such as described in the Experimental section). The reduction can either be considered as a percentage reversal (calculated by measuring the pre- and post-dose thresholds of the affected pain site with a non-affected pain site, such as described in more detail under Data Analysis in the Experimental Section) or by measuring withdrawal thresholds of the affected pain site. Preferably, the percentage reversal calculation is used.

Therefore, in one embodiment of the invention, the sensitivity to pain (such as neuropathic pain or inflammatory pain) is reversed by more than 20%, more than 30%, more than 40%, more than 50%, more than 60%, more than 70%, more than 80% or more than 90%, upon administration of a therapeutically effective amount of a Kv3.1/Kv3.2/Kv3.3 modulator, such as a compound of formula (I) or a pharmaceutically acceptable salt, solvate and/or derivative thereof. Suitably, the sensitivity to pain is reversed by more than 80% or more than 90%.

Subjects receiving the Kv3.1/Kv3.2/Kv3.3 modulator may experience secondary benefits, such as one or more of improved function, mood, sleep, quality of life, reduced time off work.

In a particular embodiment, the compounds of formula (I) or their pharmaceutically acceptable salts and/or solvates (e.g. salts) and/or derivatives thereof may be of use for the treatment or prophylaxis of neuropathic pain.

In a particular embodiment, the compounds of formula (I) or their pharmaceutically acceptable salts and/or solvates (e.g. salts) and/or derivatives thereof may be of use for the treatment or prophylaxis of inflammatory pain.

In a particular embodiment, the compounds of formula (I) or their pharmaceutically acceptable salts and/or solvates (e.g. salts) and/or derivatives thereof may be of use for the treatment or prophylaxis of miscellaneous pain.

In one embodiment is provided a compound of formula (I) for use in the prophylaxis of acute noise-induced hearing loss.

In one embodiment is provided a method for the prophylaxis of acute noise-induced hearing loss, comprising administering to a subject in need thereof a compound of formula (I).

In one embodiment is provided the use of a compound of formula (I) in the manufacture of a medicament for the prophylaxis of acute noise-induced hearing loss.

Acute noise-induced hearing loss may be caused by events such as exposure to loud noise or a blast. In these cases, where it is anticipated that a future event may result in acute noise-induced hearing loss, the compound of formula (I) or a pharmaceutically acceptable salt, solvate and/or derivative thereof may be administered before the event in order to prevent or reduce acute noise-induced hearing loss. The administration of compound (1) or a pharmaceutically acceptable salt, solvate and/or derivative thereof may prevent any acute noise-induced hearing loss, or may reduce the severity of the acute noise-induced hearing loss or may mitigate other symptoms arising from acute noise-induced hearing loss, such as tinnitus.

"Acute hearing loss" is defined as hearing loss which occurs rapidly over a period of hours or days. For example, hearing loss may occur over a period of minutes, hours or days (for example over a period of up to 1 day, such as up to 2 days, 3 days, 4 days, 5 days, 6 days or 7 days). Acute hearing loss will typically be caused by exposure to loud sound or blast. Hearing loss caused by exposure to loud sound or blast is referred to herein as "noise-induced induced hearing loss". "Acute noise induced hearing loss" is therefore hearing loss which occurs rapidly over a period of hours or days caused by exposure to loud sound or blast.

Important symptoms of acute hearing loss include:
1. a shift in the auditory threshold, i.e. an increase in the minimum sound level of a pure tone that can be heard with no other sound present;
2. tinnitus; and
3. degradation in central auditory processing, for example impaired auditory temporal processing and/or speech understanding.

A "loud" noise or blast may be at least 90 dB, for example, at least 100 dB, at least 110 dB, at least 120 dB or at least 130 dB.

In one embodiment, administration of the compound of formula (I) or a pharmaceutically acceptable salt, solvate and/or derivative thereof is initiated before an event which is anticipated to cause noise-induced acute hearing loss. For example, administration of the compound of formula (I) or a pharmaceutically acceptable salt, solvate and/or derivative thereof may be initiated up to 2 weeks in advance, such as up to 1 week, 6 days, 5 days, 4 days, 3 days, 2 days, 24 h, 12 h, 6 h, 5 h, 4 h, 3 h, 2 h, 1 h, 30 minutes or up to 15 minutes in advance of an event which is anticipated to cause noise-induced acute hearing loss. The compound of formula (I) or a pharmaceutically acceptable salt, solvate and/or derivative thereof may be administered on multiple occasions before event which is anticipated to cause noise-induced acute hearing loss.

In one embodiment, a compound of formula (I) or a pharmaceutically acceptable salt, solvate and/or derivative thereof is administered in advance of potential exposure to a noise or blast which is anticipated to cause acute noise-induced hearing loss, for preventing or reducing the development of permanent tinnitus; for preventing or reducing the development of a permanent shift in auditory thresholds; or for preventing or reducing the development of permanently degraded central auditory processing, including for example auditory temporal processing and/or speech understanding.

It will be appreciated that administration in advance may be in circumstances where the subject is considered to be at risk of exposure to a noise or blast which is anticipated to cause acute noise-induced hearing loss and is not limited to those circumstances where such exposure ultimately occurs.

In one embodiment, administration of the compound of formula (I) or a pharmaceutically acceptable salt, solvate and/or derivative thereof is initiated during an event which is anticipated to cause noise-induced acute hearing loss. The compound of formula (I) or a pharmaceutically acceptable salt, solvate and/or derivative thereof may be administered on multiple occasions during an event which is anticipated to cause noise-induced acute hearing loss.

In one embodiment, a compound of formula (I) or a pharmaceutically acceptable salt, solvate and/or derivative thereof is initially administered during a noise or blast which is anticipated to cause acute noise-induced hearing loss, for preventing or reducing the development of permanent tinnitus; for preventing or reducing the development of a permanent shift in the auditory threshold; or for preventing or reducing the development of permanently degraded central auditory processing, including for example auditory temporal processing and/or speech understanding.

In one embodiment, administration of the compound of formula (I) or a pharmaceutically acceptable salt, solvate and/or derivative thereof is initiated after an event which is anticipated to cause acute noise-induced hearing loss.

Thus, in one embodiment, a compound of formula (I) or a pharmaceutically acceptable salt, solvate and/or derivative thereof is initially administered after a noise or blast which is anticipated to cause acute noise-induced hearing loss, for preventing or reducing the development of permanent tinnitus; for preventing or reducing the development of a permanent shift in the auditory threshold; or for preventing or reducing the development of permanently degraded central auditory processing, including for example auditory temporal processing and/or speech understanding.

When the compound of formula (I) is administered after an event which is anticipated to cause acute noise-induced hearing loss, such administration is normally undertaken during the "acute phase" i.e. before the hearing loss has become established.

In one embodiment, administration of the compound of formula (I) or a pharmaceutically acceptable salt, solvate and/or derivative thereof may be initiated up to 2 months after an event which is anticipated to cause noise-induced acute hearing loss, such as up to 1 month, 2 weeks, 1 week, 6 days, 5 days, 4 days, 3 days, 2 days, 24 h, 12 h, 6 h, 5 h, 4 h, 3 h, 2 h, 1 h, 30 minutes or up to 15 minutes after an event which is anticipated to cause acute noise-induced hearing loss. The compound of formula (I) or a pharmaceutically acceptable salt, solvate and/or derivative thereof may be administered on multiple occasions after an event which is anticipated to cause noise-induced acute hearing loss.

The compound of formula (I) or a pharmaceutically acceptable salt, solvate and/or derivative thereof may be administered over a period of up to 7 days (for example, up to 1 day, up to 2 days, up to 3 days, up to 4 days, up to 5 days, up to 6 days or up to 7 days), for 1-2 weeks (for example, 7-8 days, 7-9 days, 7-10 days, 7-11 days, 7-12 days, 7-13 days or 7-14 days), for 2-4 weeks (for example, 2-3 weeks or 2-4 weeks) or for 1-2 months (for example, 4-6 weeks or 4-8 weeks).

The compound of formula (I) or a pharmaceutically acceptable salt, solvate and/or derivative thereof may initially be administered up to 1 day in advance, such as up to 2 days in advance, up to 3 days in advance, up to 5 days in advance, up to 1 week in advance, up to 2 weeks in advance or up to 1 month in advance of a noise or blast which is anticipated to cause acute noise-induced hearing loss, administration which is initiated at any point in advance exposure to a noise or blast which is anticipated to cause acute noise-induced hearing loss will typically continue for up to 2 months after exposure to the noise or blast which is anticipated to cause acute noise-induced hearing loss, such as for up to 1 month after, up to 3 weeks after, up to two weeks after, up to 1 week after, up to 5 days after, up to 3 days after, up to 2 days after, or up to 1 day after.

In one embodiment is provided a compound of formula (I) or a pharmaceutically acceptable salt, solvate and/or derivative thereof for use in preventing or reducing the development of a permanent shift in the auditory threshold, wherein the permanent shift in auditory threshold is reduced by at least 10 dB, such as at least 15 dB, at least 20 dB, at least 30 dB, at least 40 dB, or completely.

Pharmaceutical Compositions

For use in therapy the compounds of the invention are usually administered as a pharmaceutical composition. The invention also provides a pharmaceutical composition comprising a compound of formula (I), or a pharmaceutically acceptable salt and/or solvate (e.g. salt) and/or derivative thereof, and a pharmaceutically acceptable carrier or excipient.

In one embodiment, there is provided a pharmaceutical composition comprising a compound of formula (I), or a pharmaceutically acceptable salt and/or solvate (e.g. salt) and/or derivative thereof, for use in the treatment or prevention of a disease or disorder selected from the group consisting of hearing disorders, schizophrenia, depression and mood disorders, bipolar disorder, substance abuse disorders, anxiety disorders, sleep disorders, hyperacusis and disturbances of loudness perception, Mèniére's disease, disorders of balance, and disorders of the inner ear, impulse control disorder, personality disorders, attention-deficit/hyperactivity disorder, autism spectrum disorders, eating disorders, cognition impairment, ataxia, pain such as neuropathic pain, inflammatory pain and miscellaneous pain, Lewy body dementia and Parkinson's disease.

In a further embodiment, there is provided a method for the prophylaxis or treatment of a disease or disorder selected from the group consisting of hearing disorders, schizophrenia, depression and mood disorders, bipolar disorder, substance abuse disorders, anxiety disorders, sleep disorders, hyperacusis and disturbances of loudness perception, Mèniére's disease, disorders of balance, and disorders of the inner ear, impulse control disorder, personality disorders, attention-deficit/hyperactivity disorder, autism spectrum disorders, eating disorders, cognition impairment, ataxia, pain such as neuropathic pain, inflammatory pain and miscellaneous pain, Lewy body dementia and Parkinson's disease, which comprises administering to a subject in need thereof an effective amount of a pharmaceutical composition comprising a compound of formula (I) or a pharmaceutically acceptable salt and/or solvate (e.g. salt) and/or derivative thereof.

The invention also provides the use of a pharmaceutical composition comprising a compound of formula (I), or a pharmaceutically acceptable salt and/or solvate thereof (e.g. salt) and/or derivative thereof, in the manufacture of a medicament for the treatment or prophylaxis of a disease or disorder selected from the group consisting of hearing disorders, schizophrenia, depression and mood disorders, bipolar disorder, substance abuse disorders, anxiety disorders, sleep disorders, hyperacusis and disturbances of loudness perception, Mèniére's disease, disorders of balance, and disorders of the inner ear, impulse control disorder, personality disorders, attention-deficit/hyperactivity disorder, autism spectrum disorders, eating disorders, cognition impairment, ataxia, pain such as neuropathic pain, inflammatory pain and miscellaneous pain, Lewy body dementia and Parkinson's disease.

The compounds of formula (I) or their pharmaceutically acceptable salts and/or solvates and/or derivatives thereof may be administered by any convenient method, e.g. by oral, parenteral, buccal, sublingual, nasal, rectal or transdermal administration, and the pharmaceutical compositions adapted accordingly. Other possible routes of administration include intratympanic and intracochlear.

The compounds of formula (I) or their pharmaceutically acceptable salts and/or solvates and/or derivatives thereof which are active when given orally can be formulated as liquids or solids, e.g. as syrups, suspensions, emulsions, tablets, capsules or lozenges.

A liquid formulation will generally consist of a suspension or solution of the active ingredient (such as a compound of formula (I) or a pharmaceutically acceptable salt and/or solvate (e.g. salt) and/or derivative thereof) in a suitable liquid carrier(s) e.g. an aqueous solvent such as water, ethanol or glycerine, or a non-aqueous solvent, such as polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations, such as magnesium stearate, starch, lactose, sucrose and cellulose.

A composition in the form of a capsule can be prepared using routine encapsulation procedures, e.g. pellets containing the active ingredient (such as a compound of formula (I) or a pharmaceutically acceptable salt and/or solvate (e.g. salt) and/or derivative thereof) can be prepared using standard carriers and then filled into a hard gelatin capsule; alternatively a dispersion or suspension can be prepared using any suitable pharmaceutical carrier(s), e.g. aqueous gums, celluloses, silicates or oils and the dispersion or suspension then filled into a soft gelatin capsule.

Typical parenteral compositions consist of a solution or suspension of the active ingredient (such as a compound of formula (I) or a pharmaceutically acceptable salt and/or solvate (e.g. salt) and/or derivative thereof) in a sterile aqueous carrier or parenterally acceptable oil, e.g. polyethylene glycol, polyvinyl pyrrolidone, lecithin, *arachis* oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active ingredient in a pharmaceutically acceptable aqueous or non-aqueous solvent and are usually presented in single or multidose quantities in sterile form in a sealed container which can take the form of a cartridge or refill for use with an atomising device. Alternatively, the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a fluorochlorohydrocarbon or hydrofluorocarbon. Aerosol dosage forms can also take the form of pump-atomisers.

Compositions suitable for buccal or sublingual administration include tablets, lozenges and pastilles where the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches. In one embodiment the composition is in unit dose form such as a tablet, capsule or ampoule.

The composition may contain from 0.1% to 100% by weight, for example from 10 to 60% by weight, of the active material, depending on the method of administration. The composition may contain from 0% to 99% by weight, for example 40% to 90% by weight, of the carrier, depending on the method of administration. The composition may contain from 0.05 mg to 1000 mg, for example from 1.0 mg to 500 mg, of the active material, depending on the method of administration. The composition may contain from 50 mg to 1000 mg, for example from 100 mg to 400 mg of the carrier, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 mg to 1000 mg, more suitably 1.0 mg to 500 mg, and such unit doses may be administered more than once a day, for example two or three a day. Such therapy may extend for a number of weeks or months.

The dose provided to a subject will typically be a safe and effective dose, i.e. an acceptable balance of desired benefits and undesired side effects.

The invention provides, in a further aspect, a combination comprising a compound of formula (I) or a pharmaceutically acceptable, salt, solvate and/or derivative thereof (e.g. a combination comprising a compound of formula (I) or a pharmaceutically acceptable derivative thereof) together with a further pharmaceutically acceptable active ingredient or ingredients.

The invention provides a compound of formula (I), for use in combination with a further pharmaceutically acceptable active ingredient or ingredients.

When the compounds are used in combination with other therapeutic agents, the compounds may be administered either sequentially or simultaneously by any convenient route. Alternatively, the compounds may be administered separately.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations. The individual components of combinations may also be administered separately, through the same or different routes.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

Suitably, a compound of formula (I) or a pharmaceutically acceptable, salt, solvate and/or derivative thereof is administered orally.

Suitably, a compound of formula (I) or a pharmaceutically acceptable, salt, solvate and/or derivative thereof is administered at 2 to 400 mg per day, such as 2 to 300 mg per day, especially 5 to 250 mg per day.

Suitably, a compound of formula (I) or a pharmaceutically acceptable, salt, solvate and/or derivative thereof is administered once or twice per day.

Suitably, a compound of formula (I) or a pharmaceutically acceptable, salt, solvate and/or derivative thereof is administered for a period of at least three months.

Desirably, a compound of formula (I) or a pharmaceutically acceptable, salt, solvate and/or derivative thereof is administered orally, once or twice per day, at 2 to 400 mg per day, such as 2 to 300 mg per day, especially 5 to 250 mg per day.

A human subject may be an adult, such as aged 18 to 65. Alternatively, a human subject may be 66 years old or older. A compound of formula (I) or a pharmaceutically acceptable, salt, solvate and/or derivative thereof may be administered to a human subject of less than 18 years of age, such as 4 to 17 years old. Administration to a human subject of less than 18 years of age may be of particular relevance in the context of progressive myoclonic epilepsy and Fragile X syndrome.

For convenience and to assist with patient compliance, delivery technologies such as patches or implants may be used to deliver a compound of formula (I) or a pharmaceutically acceptable, salt, solvate and/or derivative thereof over a sustained period of time e.g. at least one week or at least 4 weeks.

Examples

The invention is illustrated by the compounds described below. The following examples describe the laboratory synthesis of specific compounds of the invention and are not meant to limit the scope of the invention in any way with respect to compounds or processes. It is understood that, although specific reagents, solvents, temperatures and time periods are used, there are many possible equivalent alternatives that can be used to produce similar results. This invention is meant to include such equivalents.

Analytical Equipment

Starting materials, reagents and solvents were obtained from commercial suppliers and used without further purification unless otherwise stated. Unless otherwise stated, all compounds with chiral centres are racemic. Where reactions are described as having been carried out in a similar manner to earlier, more completely described reactions, the general reaction conditions used were essentially the same. Work up conditions used were of the types standard in the art, but may have been adapted from one reaction to another. The starting material may not necessarily have been prepared from the batch referred to. Compounds synthesised may have various purities, ranging from for example 85% to 99%. Calculations of number of moles and yield are in some cases adjusted for this.

HPLC-Mass spectra (HPLC-MS) were taken on an Agilent 1100 Series LC/MSD Mass Spectrometer coupled with HPLC instrument Agilent 1100 Series, operating in positive electrospray ionization mode and in acidic gradient conditions.

Quality Control (3 minutes method): LC/MS-ES+ under acidic conditions was performed on a Zorbax SB C18 column (1.8 µm 3×50 mm). Mobile phase: A: (H2O+0.05% TFA by vol.)/B: (CH3CN+0.05% TFA by vol). Gradient: t=0 min 0% (B), from 0 to 95% (B) in 2.5 min, 95% (B) for 0.2 min, from 95 to 100% (B) in 0.2 min, 100% (B) for 0.4 min, from 100% to 0% (B) in 0.1 min. Stop time 4 min. Column T=60° C. Flow rate: 1.5 ml/min. Mass range ES+: (100-1000 amu, F=60). UV detection wavelengths: DAD 1A=220.8, DAD 1B=254.8. The use of this methodology is indicated by "QC_3_MIN" in the analytic characterization of the described compounds.

Chiral control: LC/MS-ES+ under acidic conditions was performed on a CHIRALCEL®OD-H (250×4.6 mm-5 um). Mobile phase: A: (H2O+0.05% TFA by vol.)/B: (CH3CN+ 0.05% TFA by vol). Gradient: t=0-6 min 35% (B), t=6-40 min from 35% to 50% (B), t=40-45 min from 50% to 70% (B), t=45-50 min from 70% to 35% (B), t=50-55 min 35% (B). Stop time 60 min. Column T=40° C. Flow rate: 1.0 ml/min. UV detection wavelengths: DAD 1A=220.8, DAD 1B=254.8.

Proton Magnetic Resonance (NMR) spectra were recorded either on Varian instruments at 300, 400, 500 or 600 MHz, or on Bruker instruments at 400 MHz. Chemical shifts are reported in ppm (δ) using the residual solvent line as internal standard. Splitting patterns are designed as s (singlet), br.s (broad singlet), d (doublet), t (triplet), q (quartet), dd (doublet of doublets), dt (doublet of triplets) and m (multiplet). The NMR spectra were recorded at temperatures ranging from 25 to 60° C.

2D NMR NOESY experiments were acquired with a mixing time of 500 ms using a spectral width of 3355 Hz in both f1 and f2. A total of 256 increments were collected, processed to 1 K with linear prediction, 8 scans each. Data were processed with sine bell shift in both dimensions and with lb=0.3 Hz in f1. In a number of preparations, purification was performed using Biotage automatic flash chromatography (SP1 and SP4) or Flash Master Personal systems.

Flash chromatographies were carried out on silica gel 230-400 mesh (supplied by Merck AG Darmstadt, Germany) or on silica gel 300-400 mesh (supplied by Sinopharm Chemical Reagent Co., Ltd.), Varian Mega Be—Si pre-packed cartridges, pre-packed Biotage silica cartridges (e.g. Biotage SNAP cartridge).

Abbreviations

AIBN azobisisobutyronitrile
BuLi butyllithium
$CDCl_3$ deuterated chloroform
$CCl_4$ carbon tetrachloride
$D_2O$ deuterated water
DCM dichloromethane
DIPEA N,N-diisopropylethylamine
DMAP 4-dimethylaminopyridine
DMF N,N-dimethylformamide
DMSO dimethylsulfoxide
$DMSO-d_6$ deutrated dimethylsulfoxide
$Et_2O$ diethyl ether
EtOAc ethyl acetate
h hours
HATU (O-7-azabenzotriazol-1-yl)-N,N,N',N'-tetramethyluroniumhexafluoro phosphate)
HCl hydrogen chloride
$K_2CO_3$ potassium carbonate
MeCN/$CH_3$CN acetonitrile
MeOH methanol
MOM methyloxymethyl
NaH sodium hydride
$Na_2SO_4$ sodium sulphate
$Na_2CO_3$ sodium carbonate
NaOH sodium hydroxide
NaOMe sodium methoxide
NMR Nuclear Magnetic Resonance
r.t. room temperature
T3P propylphosphonic anhydride
MTBE Methyl tert-butyl ether
TBTU Benzotriazol-1-yl-N,N,N',N'-tetramethyluronium tetrafluoroborate
TEA triethylamine
TFA trifluoroacetic acid
THF tetrahydrofuran
THP tetrahydropyran
wt. weight

Compound Examples

Intermediate 1

2-bromo-5-(7-methylspiro[2H-benzofuran-3,1'-cyclopropane]-4-yl)oxy-pyrazine

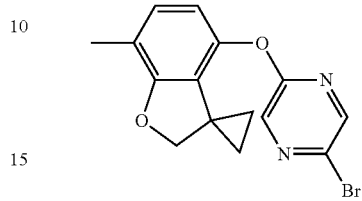

A mixture of 7-methylspiro[2H-benzofuran-3,1'-cyclopropane]-4-ol (Intermediate 156 WO2012076877, 1.11 g, 6.30 mmol), 2,5-dibromopyrazine (1.5 g, 6.30 mmol) and dipotassium carbonate (1.31 g, 9.46 mmol) in N,N-dimethylformamide (14 mL) was stirred at 120° C. for 3 hours. After cooling, the reaction mixture was diluted with MTBE (100 ml) and washed with brine (50 ml). Phases were separated and the aqueous layer was washed with MTBE (100 ml) and EtOAc (100 ml). All organic phases are collected, dried over $Na_2SO_4$, filtered and evaporated. The residue was purified by flash chromatography (Biotage System) on silica gel using a SNAP 100 g as column and Cyclohexane: Ethyl acetate from 100:0 to 90:10 as eluent affording 2-bromo-5-(7-methylspiro[2H-benzofuran-3,1'-cyclopropane]-4-yl)oxy-pyrazine (1.8 g) as white solid.

LC/MS: QC_3_MIN: Rt=2.705 min; m/z 333 & 335 [M+H]+.

The following compounds were prepared using the foregoing methodology, replacing 7-methylspiro[2H-benzofuran-3,1'-cyclopropane]-4-ol with the appropriate phenol. Final products were purified by flash-chromatography (Silica cartridge; Cyclohexane/EtOAc or other appropriate solvent system).

| Int. | Structure | Name | Phenol | LCMS |
|---|---|---|---|---|
| 2 | 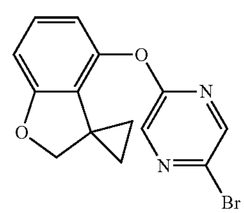 [SMILES: Brc1cnc(Oc2cccc3c2C2(CC2)CO3)cn1] | 2-bromo-5-spiro[2H-benzofuran-3,1'-cyclopropane]-4-yloxy-pyrazine | spiro[2H-benzofuran-3,1'-cyclopropane]-4-ol (Intermediate 85 WO2012076877) | LC/MS: QC_3_MIN: Rt = 2.575 min; m/z 319 & 321 [M + H]+. |
| 3 | 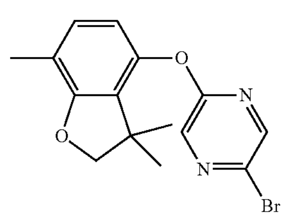 [SMILES: Cc1ccc(Oc2cnc(Br)cn2)c2c1OCC2(C)C] | 2-bromo-5-[(3,3,7-trimethyl-2H-benzofuran-4-yl)oxy]pyrazine | 3,3,7-trimethyl-2H-benzofuran-4-ol (Intermediate 184 WO2012076877) | LC/MS: QC_3_MIN: Rt = 2.365 min; m/z 335 & 337 [M + H]+. |

-continued

| Int. | Structure | Name | Phenol | LCMS |
|---|---|---|---|---|
| 4 | (structure) | 2-bromo-5-[(3,3-dimethyl-2H-benzofuran-4-yl)oxy]pyrazine | 3,3-dimethyl-2H-benzofuran-4-ol (Intermediate 50 WO2012076877) | LC/MS: QC_3_MIN: Rt = 2.632 min; m/z 321 & 323 [M + H]+. |

Intermediate 5 Route 1

3-(5-chloropyrazin-2-yl)-5,5-dimethyl-imidazolidine-2,4-dione

To a solution of bis(trichloromethyl) carbonate (950 mg, 3.20 mmol) in ethyl acetate (30 mL) at 0° C. a solution of 5-chloropyrazin-2-amine (0.75 g, 5.79 mmol)/N,N-diisopropylethylamine (6.05 ml, 34.74 mmol) in ethyl acetate (12 mL) was added dropwise and the reaction mixture was stirred for 15 minutes at the same temperature. Maintaining the reaction mixture at 0° C., vacuum was applied (5 minutes) in order to remove the excess of phosgene. A solution of 4-(dimethylamino)pyridine (710 mg, 5.81 mmol) in ethyl acetate (8 mL)/dichloromethane (2 mL) was added and the reaction mixture was stirred for 5 minutes at the same temperature. Then, methyl 2-amino-2-methyl-propanoate hydrochloride (1.4 g, 9.1 mmol) was added at 0° C. and the reaction mixture was stirred for 30 minutes at the same temperature. The reaction was quenched with a solution 0.2 N of HCl (100 ml) and the two phases were separated. The organic layer was washed with brine (100 ml), dried over Na$_2$SO$_4$, filtered and evaporated affording the urea intermediate.

The urea was dissolved in dichloromethane (20 mL) and at 0° C. sodium methoxide (315 mg, 5.83 mmol) was added. The reaction mixture was stirred 15 minutes at the same temperature; the reaction was quenched with a saturated solution of NH$_4$Cl to allow the pH to reach 3-4. The mixture was extracted with ethyl acetate (50 ml); phases were separated, and the organic layer was washed with brine (50 ml), dried over Na$_2$SO$_4$, filtered and evaporated. The residue were purified by reverse phase flash chromatography (Biotage System) on C-18 phase using a SNAP 30 g as column and Water:Acetonitrile from 95:5 to 40:60 as eluent. The appropriate fractions were combined and evaporated to dryness affording 3-(5-chloropyrazin-2-yl)-5,5-dimethyl-imidazolidine-2,4-dione (220 mg) as a pale brown solid.

LC/MS: QC_3_MIN: Rt=1.649 min; m/z 241 & 243 [M+H]+.

The following compounds were prepared using the foregoing methodology, replacing 2,2-dimethylglycine methyl ester hydrochloride with the appropriate amino ester hydrochloride. Final products were purified by flash-chromatography (Silica cartridge; Cyclohexane/EtOAc or other appropriate solvent system) or triturated in an appropriate solvent or crystallised from an appropriate solvent.

| Int. | Structure | Name | Amino ester hydrochloride | LCMS |
|---|---|---|---|---|
| 6 | (structure) | 5R)-3-(5-chloropyrazin-2-yl)-5-ethyl-5-methyl-imidazolidine-2,4-dione | methyl (2R)-2-amino-2-methyl-butanoate hydrochloride | LC/MS: QC_3_MIN: Rt = 1.546 min; m/z 255 & 257 [M + H]+. |

Intermediate 5 Route 2

3-(5-chloropyrazin-2-yl)-5,5-dimethyl-imidazolidine-2,4-dione

To a solution of 5-chloropyrazin-2-amine (500 mg, 3.86 mmol) and 2-amino-2-methyl-propanoic acid hydrochloride (646 mg, 4.63 mmol) in acetonitrile (10 mL), Propylphosphonic anhydride solution ≥50 wt. % in ethyl acetate (3.68 g, 5.78 mmol) was slowly added at RT. The reaction mixture was stirred at 80° C. for 6 h. The reaction mixture was diluted with Ethyl Acetate (10 ml) and an aqueous solution of NaOH 1 N was added, while the ph was allowed to reach ~8. The two phases were separated and the organic one was washed with brine (10 ml), dried with Na$_2$SO$_4$, concentrated under vacuum and the crude was purified by Flash Chromatography on silica gel (BIOTAGE SYSTEM), using a SNAP 25 g as column and DCM:MEOH from 99/1 to 90/10 as eluent, affording 2-amino-N-(5-chloropyrazin-2-yl)-2-methyl-propanamide (190 mg) as yellow solid.

LC/MS: QC_3_MIN: Rt=1.181 min; m/z 215 & 217 [M+H]+.

To a solution of 2-amino-N-(5-chloropyrazin-2-yl)-2-methyl-propanamide (190 mg, 0.88 mmol) and triethylamine (268 mg, 2,6555 mmol) in dichloromethane (5 mL), at 0° C. a solution of bis(trichloromethyl) carbonate (105.07 mg, 0.3541 mmol) in dichloromethane (4 mL) was slowly added. and the reaction mixture was stirred for 30 minutes at the same temperature. The reaction mixture was diluted in DCM (10 mL), washed with an aqueous solution 0.2N of HCl (10 mL) and Brine (10 mL). The organic phases were concentrated under vacuum and the crude was purified by flash chromatography on silica gel (Biotage system) using a SNAP 25 g as column and Chexane/EtOAc from 80/20 to 0/100 as eluent affording 3-(5-chloropyrazin-2-yl)-5,5-dimethyl-imidazolidine-2,4-dione (130 mg) as white solid.

LC/MS: QC_3_MIN: Rt=1.598 min; m/z 241 & 243 [M+H]+.

Intermediate 7 tert-butyl N-[(1R)-1-carbamoylpropyl]carbamate

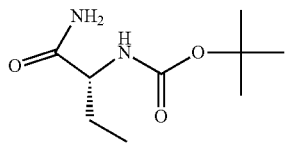

A mixture of [dimethylamino-(3-oxidotriazolo[4,5-b]pyridin-3-ium-1-yl)methylene]-dimethyl-ammonium tetrafluoroborate (1,1084 g, 3.4415 mmol), N,N-diisopropylethylamine (0.7939 g, 6.1431 mmol) and (2R)-2-(tert-butoxycarbonylamino)butanoic acid (0.5000 g, 2.4601 mmol) in dry N,N-dimethylformamide (8 mL) was stirred at room temperature for 10 minutes. Hexamethyldisilazane (0.5960 g, 3.6928 mmol) was added and the mixture stirred for 18 h.

Reaction mixture was separated in MTBE (30 mL) and Brine (20 mL). The organic layer was dried with sodium sulphate, filtered and the solvent removed. The resulting oil triturated in MTBE (3 mL) and the resulting precipitate was washed with MTBE and dried via vacuum to give tert-butyl N-[(1R)-1-carbamoylpropyl]carbamate (0.3000 g, 1.4833 mmol, 60,294%) as a white solid.

LC/MS: QC_3_MIN: m/z 147 [M-tBu+H]+.

The following compounds were prepared using the foregoing methodology, replacing (2R)-2-(tert-butoxycarbonilamino) butanoic acid with the appropriate protected amino-acid.

Intermediate 9 (route 1)

tert-butyl N-[(1R)-1-[[5-(7-methylspiro[2H-benzofuran-3,1'-cyclopropane]-4-yl)oxypyrazin-2-yl]carbamoyl]propyl]carbamate

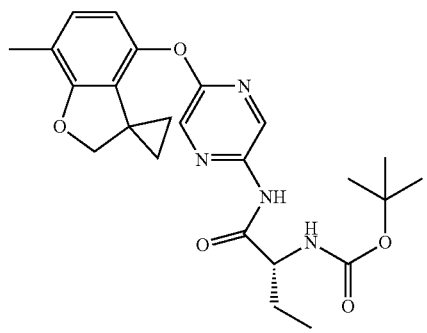 [SMILES: CC[C@@H](NC(=O)OC(C)(C)C)C(=O)Nc1cnc(Oc2ccc(C)c3c2C2(CC2)CO3)cn1]

A mixture of 2-bromo-5-(7-methylspiro[2H-benzofuran-3,1'-cyclopropane]-4-yl)oxy-pyrazine (Intermediate 1, 50 mg, 0.15 mmol), tert-butyl N-[(1R)-1-carbamoylpropyl]carbamate (Intermediate 7, 46 mg, 0.23 mmol), Tris(dibenzylideneacetone)dipalladium(0) (10.3 mg, 0.011 mmol), dicyclohexyl-[2-(2,4,6-triisopropylphenyl)phenyl]phosphane (XPhos) (5.4 mg, 0.011 mmol) and cesium carbonate (73 mg, 0.22 mmol) in 1,4-dioxane (2 mL) was stirred under an atmosphere of nitrogen at 80° C. for 3 h.

The reaction was partitioned between ethyl acetate and brine. The organic layer was separated, dried with sodium sulphate, filtered and evaporated to dryness. The residue was purified by flash chromatography on silica gel (Biotage system) using a SNAP 10 g column and cyclohexane and EtOAc from 100/0 to 0/100 as eluent. The appropriate fractions were combined and evaporated to dryness, affording tert-butyl N-[(1R)-1-[[5-(7-methylspiro[2H-benzofuran-3,1'-cyclopropane]-4-yl)oxypyrazin-2-yl]carbamoyl]propyl]carbamate (10 mg).

LC/MS: QC_3_MIN: Rt=2.696 min; m/z 455 [M+H]+.

| Int. | Structure | Name | Amino-acid | LCMS |
| --- | --- | --- | --- | --- |
| 8 | 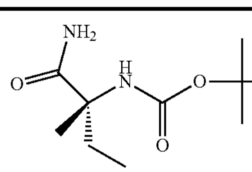 | tert-butyl N-[(1R)-1-carbamoyl-1-methyl-propyl]carbamate | (2R)-2-(tert-butoxycarbonyl-amino)-2-methyl-butanoic acid | LC/MS: QC_3_MIN: m/z 455 [2M + Na]+. |

Intermediate 9 (route 2)

tert-butyl N-[(1R)-1-[[5-(7-methylspiro[2H-benzofuran-3,1'-cyclopropane]-4-yl)oxypyrazin-2-yl]carbamoyl]propyl]carbamate

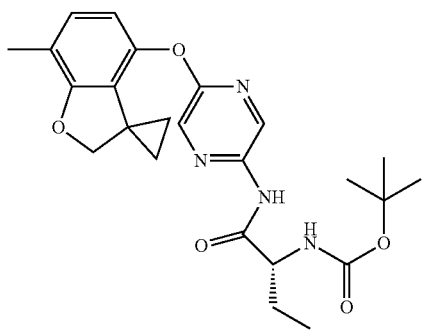 [SMILES: CC[C@@H](NC(=O)OC(C)(C)C)C(=O)Nc1cnc(Oc2ccc(C)c3c2C2(CC2)CO3)cn1]

To a mixture of 2-bromo-5-(7-methylspiro[2H-benzofuran-3,1'-cyclopropane]-4-yl)oxy-pyrazine (Intermediate 1, 16 g, 48.0 mmol), tert-butyl N-[(1R)-1-carbamoylpropyl]carbamate (Intermediate 7, 10 g, 49.4 mmol), cesium carbonate (24.16 g, 74.17 mmol) in 1,4-dioxane (150 mL), after flushing with argon, diacetoxypalladium (0.555 g, 2.47 mmol) and (5-diphenylphosphanyl-9,9-dimethyl-xanthen-4-yl)-diphenyl-phosphane (2.15 g, 3.71 mmol) were added. For three times cycle vacuum-argon was applied and the reaction mixture was stirred at 95° C. for 1.5 h. The reaction mixture was cooled using an external ice bath and then filtered under vacuum to remove cesium carbonate. The filtrate was collected, diluted with EtOAc (150 ml) and washed with an aqueous saturated solution of $NH_4Cl$ (100 ml) and then with a n aqueous saturated solution of NaCl (100 ml), dried with sodium sulphate, filtered and evaporated to dryness. The residue was purified by flash chromatography on silica gel (Biotage system) using 2×SNAP 100 g column (200 g silica) and cyclohexane/EtOAc from 0 to 40% as eluent affording tert-butyl N-[(1R)-1-[[5-(7-methylspiro[2H-benzofuran-3,1'-cyclopropane]-4-yl)oxypyrazin-2-yl]carbamoyl]propyl]carbamate (16.8 g) as yellow solid.

The following compounds were prepared using the foregoing methodology (either route 1 or route 2), replacing 2-bromo-5-(7-methylspiro[2H-benzofuran-3,1'-cyclopropane]-4-yl)oxy-pyrazine (Intermediate 1) with the appropriate bromopyrazine. Final products were purified by flash-chromatography (Silica cartridge; Cyclohexane/EtOAc or other appropriate solvent system).

| Int. | Structure | Name | bromopyrazine | LCMS |
|---|---|---|---|---|
| 10 | 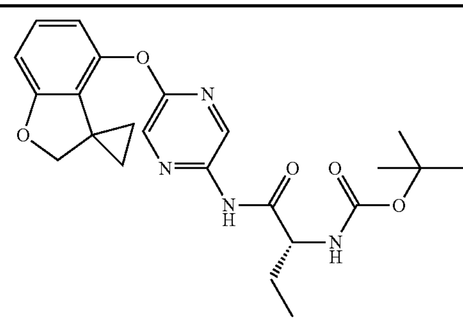 | tert-butyl N-[(1R)-1-[(5-spiro[2H-benzofuran-3,1'-cyclopropane]-4-yloxypyrazin-2-yl) carbamoyl]propyl] carbamate | 2-bromo-5-spiro[2H-benzofuran-3,1'-cyclopropane]-4-yloxy-pyrazine (Intermediate 2) | LC/MS: QC_3_MIN: Rt = 2.246 min; m/z 441 [M + H]+. |
| 11 | 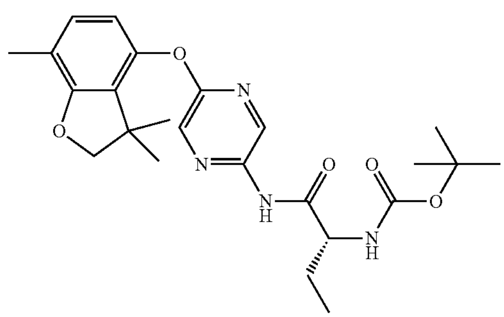 | tert-butyl N-[(1R)-1-[5-[(3,3,7-trimethyl-2H-benzofuran-4-yl)oxy]pyrazin-2-yl]carbamoyl]propyl] carbamate | 2-bromo-5-[(3,3,7-trimethyl-2H-benzofuran-4-yl)oxy]pyrazine (Intermediate 3) | LC/MS: QC_3_MIN: Rt = 2.309 min; m/z 457 [M + H]+. |
| 12 | 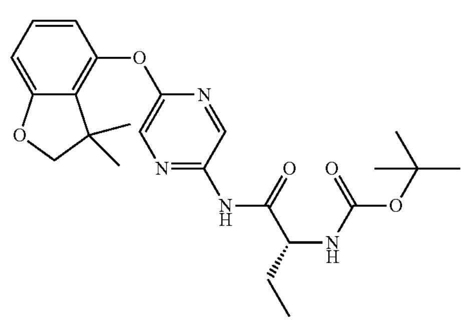 [SMILES: CC[C@@H](NC(=O)OC(C)(C)C)C(=O)Nc1cnc(Oc2cccc3c2C2(CC2)CO3)cn1] | tert-butyl N-[(1R)-1-[5-[(3,3-dimethyl-2H-benzofuran-4-yl)oxy]pyrazin-2-yl]carbamoyl]propyl] carbamate | 2-bromo-5-[(3,3-dimethyl-2H-benzofuran-4-yl)oxy]pyrazine (Intermediate 4) | LC/MS: QC_3_MIN: Rt = 2.366 min; m/z 443 [M + H]+. |

Intermediate 13

(2R)-2-amino-N-[5-(7-methylspiro[2H-benzofuran-3,1'-cyclopropane]-4-yl)oxypyrazin-2-yl]butanamide

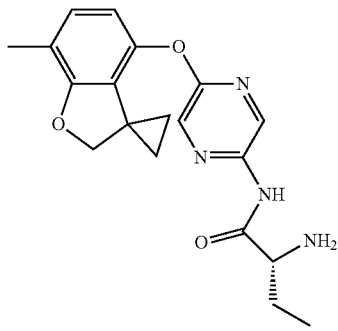 [SMILES: CC[C@@H](N)C(=O)Nc1cnc(Oc2ccc(C)c3c2C2(CC2)CO3)cn1]

A mixture of tert-butyl N-[(1R)-1-[[5-(7-methylspiro[2H-benzofuran-3,1'-cyclopropane]-4-yl)oxypyrazin-2-yl]carbamoyl]propyl]carbamate (Intermediate 9, 16 mg, 0.035 mmol) and 2,2,2-trifluoroacetic acid (0.50 mL, 6.53 mmol) in dichloromethane (2 mL) was stirred at room temperature for 2 h.

The reaction mixture was diluted with dichloromethane (20 ml) and a saturated solution of $NaHCO_3$ (aq) was added while the pH was allowed to reach 8. The phases were separated and the organic layer was washed with brine (20 ml), dried over $Na_2SO_4$, filtered and evaporated affording (2R)-2-amino-N-[5-(7-methylspiro[2H-benzofuran-3,1'-cyclopropane]-4-yl)oxypyrazin-2-yl]butanamide (13 mg) that was used in the next step without further purification.

LC/MS: QC_3_MIN: Rt=2.009 min; m/z 355 [M+H]+.

The following compounds were prepared using the foregoing methodology, replacing tert-butyl N-[(1R)-1-[[5-(7-methylspiro[2H-benzofuran-3,1'-cyclopropane]-4-yl)oxypyrazin-2-yl]carbamoyl]propyl]carbamate (Intermediate 9) with the appropriate Boc amine.

| Int. | Structure | Name | Boc amine | LCMS |
|---|---|---|---|---|
| 14 | 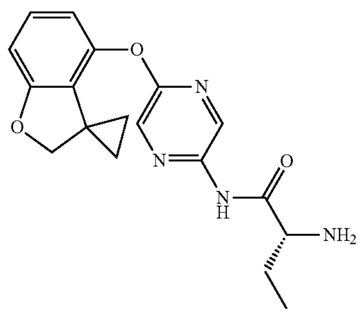 [SMILES: CC[C@@H](N)C(=O)Nc1cnc(Oc2cccc3c2C2(CC2)CO3)cn1] | (2R)-2-amino-N-(5-spiro[2H-benzofuran-3,1'-cyclopropane]-4-yloxypyrazin-2-yl)butanamide | tert-butyl N-[(1R)-1-[(5-spiro[2H-benzofuran-3,1'-cyclopropane]-4-yloxypyrazin-2-yl)carbamoyl]propyl]carbamate (Intermediate 10) | LC/MS: QC_3_MIN: Rt = 1.675 min; m/z 342 [M + H]+. |
| 15 | 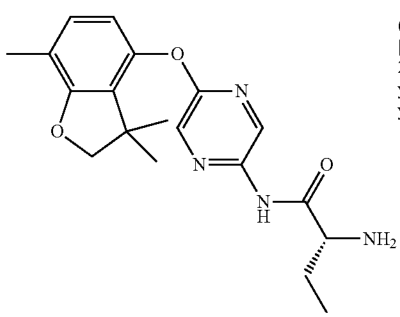 [SMILES: CC[C@@H](N)C(=O)Nc1cnc(Oc2ccc(C)c3c2C(C)(C)CO3)cn1] | (2R)-2-amino-N-[5-[(3,3,7-trimethyl-2H-benzofuran-4-yl)oxy]pyrazin-2-yl]butanamide | tert-butyl N-[(1R)-1-[5-[(3,3,7-trimethyl-2H-benzofuran-4-yl)oxy]pyrazin-2-yl]carbamoyl]propyl]carbamate (Intermediate 11) | LC/MS: QC_3_MIN: Rt = 1.756 min; m/z 357 [M + H]+. |
| 16 | 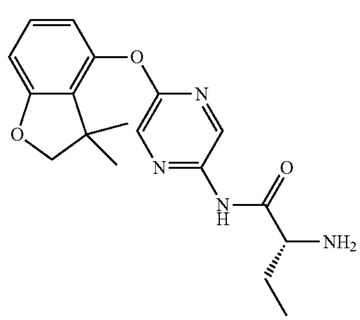 [SMILES: CC[C@@H](N)C(=O)Nc1cnc(Oc2cccc3c2C(C)(C)CO3)cn1] | (2R)-2-amino-N-[5-[(3,3-dimethyl-2H-benzofuran-4-yl)oxy]pyrazin-2-yl]butanamide | tert-butyl N-[(1R)-1-[5-[(3,3-dimethyl-2H-benzofuran-4-yl)oxy]pyrazin-2-yl]carbamoyl]propyl]carbamate (Intermediate 12) | LC/MS: QC_3_MIN: Rt = 1.673 min; m/z 343 [M + H]+. |

Intermediate 17

(5R)-5-ethyl-5-methyl-imidazolidine-2,4-dione

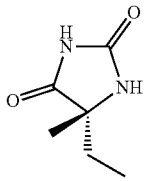

A mixture of tert-butyl N-[(1R)-1-carbamoyl-1-methyl-propyl]carbamate (Intermediate 8, 100 mg, 0.4624 mmol) and potassium carbonate (191.71 mg, 1.3871 mmol) in 1-butanol (5 mL) was stirred under an atmosphere of nitrogen at 95° C. overnight. After cooling, potassium carbonate was filtered off and the reaction mixture was diluted with ethyl acetate (30 ml) and washed with an aqueous 0.1 N HCl solution (30 ml) and then with brine (30 ml). Phases were separated and the organic layer was collected, dried over $Na_2SO_4$, filtered and evaporated affording (5R)-5-ethyl-5-methyl-imidazolidine-2,4-dione (60 mg, 0.4221 mmol, 91,283%).

LC/MS: QC_3_MIN: m/z 285 [2M+H]+.

Intermediate 18 tert-butyl N-(1-carbamoylcyclobutyl)carbamate

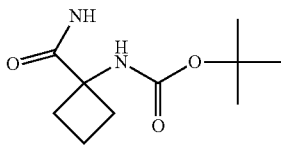

Intermediate 18 was prepared using the methodology described for Intermediate 7, replacing (2R)-2-(tert-butoxycarbonylamino)butanoic acid with 1-(tert-butoxycarbonylamino)cyclobutanecarboxylic acid.

LC/MS: QC_3MIN: m/z 159 [M-tBu+H]+.

Intermediate 19 tert-butyl N-[1-[[5-(7-methylspiro[2H-benzofuran-3,1'-cyclopropane]-4-yl)oxypyrazin-2-yl]carbamoyl]cyclobutyl]carbamate

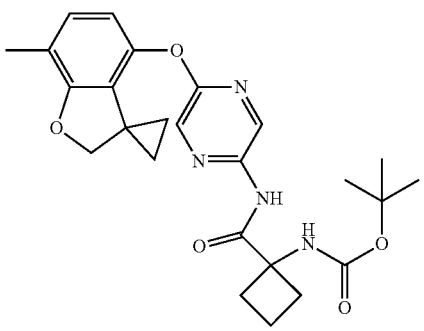 [SMILES: Cc1ccc(Oc2cnc(NC(=O)C3(NC(=O)OC(C)(C)C)CCC3)cn2)c2c1OCC21CC1]

A mixture of 2-bromo-5-(7-methylspiro[2H-benzofuran-3,1'-cyclopropane]-4-yl)oxy-pyrazine (Intermediate 1, 50 mg, 0.1501 mmol), tert-butyl N-(1-carbamoylcyclobutyl)carbamate (Intermediate 18, 64 mg, 0.2987 mmol), dipotassium carbonate (62 mg, 0.4486 mmol), copper(I) iodide (2.9 mg, 0.0152 mmol) and N,N'-dimethylethane-1,2-diamine (0.0065 mL, 0.0601 mmol) in 1-butanol (1 mL) was stirred under an atmosphere of nitrogen at 95° C. for 4 h. After cooling, the reaction mixture was diluted with ethyl acetate (30 ml) and washed with an aqueous 0.1 M HCl solution (30 ml) and then with brine (30 ml). Phases were separated, and the organic layer was collected, dried over $Na_2SO_4$, filtered and evaporated. The residue was purified by flash chromatography (Biotage System) on silica gel using a SNAP 10 g as column and Cyclohexane: Ethyl acetate from 100:0 to 30:70 as eluent affording tert-butyl N-[1-[[5-(7-methylspiro[2H-benzofuran-3,1'-cyclopropane]-4-yl)oxypyrazin-2-yl]carbamoyl]cyclobutyl]carbamate (18 mg).

LC/MS: QC_3_MIN: Rt=2.675 min; m/z 467 [M+H]+.

Intermediate 20

1-amino-N-[5-(7-methylspiro[2H-benzofuran-3,1'-cyclopropane]-4-yl)oxypyrazin-2-yl]cyclobutanecarboxamide

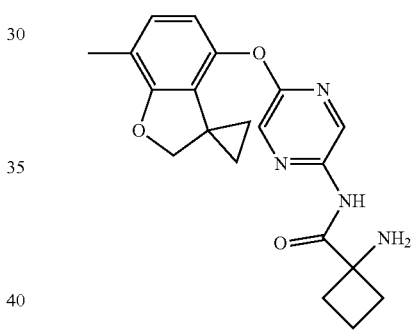

Intermediate 20 was prepared using the methodology described for Intermediate 13, replacing tert-butyl N-[(1R)-1-[[5-(7-methylspiro[2H-benzofuran-3,1'-cyclopropane]-4-yl)oxypyrazin-2-yl]carbamoyl]propyl]carbamate (Intermediate 9) with tert-butyl N-[1-[[5-(7-methylspiro[2H-benzofuran-3,1'-cyclopropane]-4-yl)oxypyrazin-2-yl]carbamoyl]cyclobutyl]carbamate (Intermediate 19).

LC/MS: QC_3_MIN: Rt=1.979 min; m/z 367 [M+H]+.

Intermediate 21 tert-butyl N-(1-carbamoylcyclopropyl)carbamate

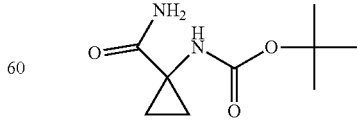

Intermediate 21 was prepared using the methodology described for Intermediate 7, replacing (2R)-2-(tert-butoxycarbonylamino)butanoic acid with 1-(tert-butoxycarbonylamino)cyclopropanecarboxylic acid.

Intermediate 22 tert-butyl N-[1-[[5-(7-methylspiro[2H-benzofuran-3,1'-cyclopropane]-4-yl)oxypyrazin-2-yl]carbamoyl]cyclopropyl]carbamate

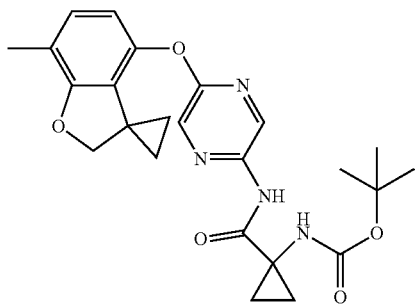 [SMILES: Cc1ccc(Oc2cnc(NC(=O)C3(NC(=O)OC(C)(C)C)CC3)cn2)c2c1OCC21CC1]

A mixture of dicyclohexyl-[2-(2,4,6-triisopropylphenyl)phenyl]phosphane (12 mg, 0.0252 mmol), tert-butyl N-(1-carbamoylcyclopropyl)carbamate (Intermediate 21, 67 mg, 0.3346 mmol), Tris(dibenzylideneacetone)dipalladium(0) (22 mg, 0.0240 mmol), 2-bromo-5-(7-methylspiro[2H-benzofuran-3,1'-cyclopropane]-4-yl)oxy-pyrazine (Intermediate 1, 79.518 mg, 0.2387 mmol) and caesium carbonate (116 mg, 0.3560 mmol) in 1,4-dioxane (1 mL) were stirred under an atmosphere of nitrogen at 95° C. for 2 h. Additional tert-butyl N-(1-carbamoylcyclopropyl)carbamate (Intermediate 21, 67 mg, 0.3346 mmol) and Tris(dibenzylideneacetone)dipalladium(0) (22 mg, 0.0240 mmol) was added and the reaction mixture was stirred at 95° C. under nitrogen for a further 2 h, followed by the addition of a further dicyclohexyl-[2-(2,4,6-triisopropylphenyl)phenyl]phosphane (12 mg, 0.0252 mmol), Tris(dibenzylideneacetone)dipalladium(0) (22 mg, 0.0240 mmol) and caesium carbonate (58 mg) and the mixture was stirred under nitrogen for a further 2 h. The reaction mixture was then quenched with water (10 mL), NH$_4$Cl (10 mL) and extracted with ethyl acetate (20 mL). The organic layer was then washed with brine (15 mL), dried over Na$_2$SO$_4$, filtered, then concentrated in vacuo. The crude was purified by flash chromatography (Biotage System) on silica gel using a SNAP 10 g as column and Cyclohexane:Ethyl acetate 90:10 to 70:30 as eluent to afford tert-butyl N-[1-[[5-(7-methylspiro[2H-benzofuran-3,1'-cyclopropane]-4-yl)oxypyrazin-2-yl]carbamoyl]cyclopropyl]carbamate (55 mg) as a yellow solid.

LC/MS: QC_3_MIN: Rt=2.634 min; m/z 453 [M+H]+.

Intermediate 23

1-amino-N-[5-(7-methylspiro[2H-benzofuran-3,1'-cyclopropane]-4-yl)oxypyrazin-2-yl]cyclopropanecarboxamide

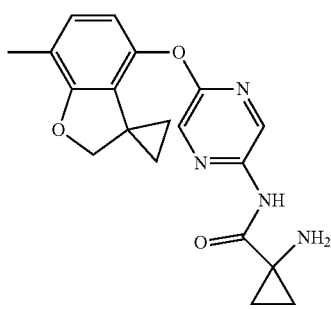 [SMILES: Cc1ccc(Oc2cnc(NC(=O)C3(N)CC3)cn2)c2c1OCC21CC1]

tert-butyl N-[1-[[5-(7-methylspiro[2H-benzofuran-3,1'-cyclopropane]-4-yl)oxypyrazin-2-yl]carbamoyl]cyclopropyl]carbamate (Intermediate 22, 55 mg, 0.1215 mmol) was dissolved in dichloromethane (4 mL) and cooled to 0° C. 2,2,2-trifluoroacetic acid (1154.7 mg, 10.026 mmol) (0.8 mL) was added dropwise and the reaction was stirred at room temperature for 1 hour. The reaction mixture was then cooled to 0° C. and NaHCO$_3$ was added until the pH reached 8. The mixture was then allowed to warm to room temperature and extracted with DCM (10 mL). The organic layer was dried over Na$_2$SO$_4$, filtered and concentrated in vacuo to afford 1-amino-N-[5-(7-methylspiro[2H-benzofuran-3,1'-cyclopropane]-4-yl)oxypyrazin-2-yl]cyclopropanecarboxamide (40 mg) as a yellow oil.

LC/MS: QC_3_MIN: Rt=1.935 min; m/z 353 [M+H]+.

Intermediate 24

1,3-dibenzyloxy-2-bromo-benzene

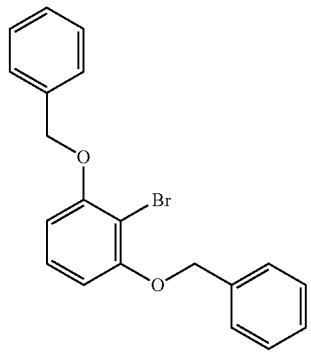 [SMILES: Brc1c(OCc2ccccc2)cccc1OCc1ccccc1]

To a solution of 2-bromobenzene-1,3-diol (20 g, 105.8 mmol) in acetone (200 mL), potassium carbonate (43.87 g, 317.4 mmol) was added followed by the addition of benzyl bromide (40.72 g, 238.1 mmol) (28 ml) and the reaction mixture was refluxed for 1.5 hours. After cooling, the reaction mixture was filtered under vacuum and the filtrate was concentrated to dryness. The residue was diluted with ethyl acetate (100 ml) and washed with water (100 ml) and then with brine (100 ml). Phases were separated and the organic layer was dried over Na$_2$SO$_4$, filtered and concentrated. The residue was suspended in isopropanol (8 volumes) and the mixture heated at 80° C. and stirred for 1 hour at this temperature (to obtain a clear solution). Then, the mixture was allowed to reach room temperature (in 1 h) and the obtained suspension was filtered. The solid was washed with ice cold isopropanol and then dried affording the title compound 1,3-dibenzyloxy-2-bromo-benzene (34 g) as pale pink solid.

LC/MS: QC_3_MIN: Rt=2.688 min.

Intermediate 25 bromo-(1-methoxycarbonylcyclopropyl)zinc

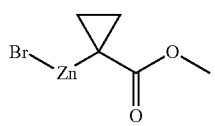

In a two-neck round-bottom flask activated zinc powder (6.84 g, 104.6 mmol) was added and the powder was heated under vacuum. The system was put under argon and dry tetrahydrofuran (58 mL) was added. Then, 1,2-dibromoethane (2.18 g, 11.62 mmol) was added and the mixture was heated to reflux. Chlorotrimethylsilane (505 mg, 4.65 mmol) was added in a single portion and the mixture kept stirring at reflux temperature. A solution of methyl 1-bromocyclopropylcarboxylate (10.4 g, 58.1 mmol) in dry tetrahydrofuran (12 mL) was slowly added at the same temperature and the reaction mixture was refluxed for 1.5 h. The reaction mixture was cooled down to room temperature and the zinc was allowed to settle affording 70 ml of a 0.83M (theoretical) solution of bromo-(1-methoxycarbonylcyclopropyl)zinc in THF which was used in the next step without further work up.

Intermediate 26 methyl 1-(2,6-dibenzyloxyphenyl)cyclopropanecarboxylate

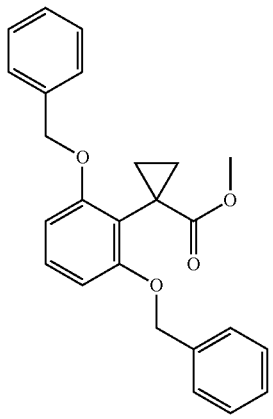 [SMILES: COC(=O)C1(c2c(OCc3ccccc3)cccc2OCc2ccccc2)CC1]

To a solution of 1,3-dibenzyloxy-2-bromo-benzene (Intermediate 24, 16 g, 43.33 mmol) and Bis(tri-tert-butylphosphine)palladium(0) (221 mg, 0.43 mmol) in N,N-dimethylformamide (150 mL) pre-heated at 70° C., a 0.83M (theoretical) solution of bromo-(1-methoxycarbonylcyclopropyl)zinc in THF (Intermediate 25, 60 ml) was added (via cannulation) and the reaction mixture was stirred at the same temperature for 40 minutes. After cooling, the reaction mixture was concentrated under vacuum up to ~30 ml and the residue was diluted with ethyl acetate (450 ml) and washed twice with a 1 N aqueous solution of HCl (2×100 ml) and then three times with ice cold brine (3×100 ml). Phases were separated and the organic layer was filtered under vacuum on a Gooch filter assembled with filter paper and cellulose and washing with ethyl acetate. The filtrate was dried over Na₂SO₄, filtered and evaporated affording the title compound methyl 1-(2,6-dibenzyloxyphenyl)cyclopropanecarboxylate (15.5 g) that was in the next step without further purification.

LC/MS: QC_3_MIN: Rt=2.606 min; m/z 389 [M+H]+.

Intermediate 27

4-hydroxyspiro[benzofuran-3,1'-cyclopropane]-2-one

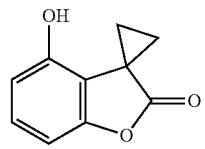

The reaction was performed in three different runs using about 20 g of starting material each. General procedure: to a mixture of methyl 1-(2,6-dibenzyloxyohenyl)cyclopropanecarboxylate (Intermediate 26, 20.4 g, 52.52 mmol) and palladium 5% wt. on carbon (1.02 g) in ethanol (200 ml), ammonium formate (16.56 g, 262.6 mmol) was added and the reaction mixture was stirred at 80° C. for 1 hour. After cooling, the catalyst was filtered off on a cellulose pad and the filtrate was concentrated under vacuum up to ~20 ml.

The residues coming from the 3 runs were put together and diluted with ethyl acetate (400 ml) and washed twice with water (2×300 ml). The two phases were separated and the organic one was washed with brine (300 ml), dried with Na₂SO₄ and concentrated under vacuum affording 4-hydroxyspiro[benzofuran-3,1'-cyclopropane]-2-one (27.55 g) (containing ~10-15% of the uncyclized methyl 1-(2,6-dihydroxyphenyl)cyclopropanecarboxylate intermediate) that was used in the next step without further purification.

LC/MS: QC_3_MIN: Rt=1.707 min.

Intermediate 28

4-benzyloxyspiro[benzofuran-3,1'-cyclopropane]-2-one

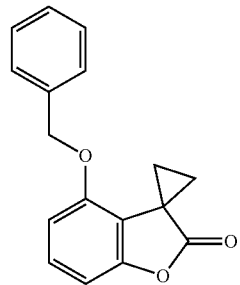 [SMILES: O=C1Oc2cccc(OCc3ccccc3)c2C12CC2]

To a solution of 4-hydroxyspiro[benzofuran-3,1'-cyclopropane]-2-one (Intermediate 27, 28.5 g, 161.8 mmol) (containing ~10-15% of the uncyclized methyl 1-(2,6-dihydroxyphenyl)cyclopropanecarboxylate intermediate) in acetonitrile (200 mL)/tetrahydrofuran (50 mL), potassium carbonate (33.54 g, 242.7 mmol) was added and the reaction mixture was stirred at 70° C. for 1.5 hours. The reaction mixture was then cooled to room temperature and benzyl bromide (27.67 g, 161.8 mmol) was slowly added. The reaction mixture was stirred at 60° C. for 5 hours. After cooling, the reaction mixture was filtered under vacuum and the solid discarded, the filtrate was concentrated up to 50 ml, diluted with ethyl acetate (250 ml) and washed twice with brine (2×100 ml). Phases were separated and the organic layer was dried over Na₂SO₄, filtered and evaporated affording the title compound 4-benzyloxyspiro[benzofuran-3,1'-cyclopropane]-2-one (42.4 g) that was used in the next step without further purification.

LC/MS: QC_3MIN: Rt=2.389 min; m/z 267 [M+H]+.

Intermediate 29

3-benzyloxy-2-[1-(hydroxymethyl)cyclopropyl]phenol

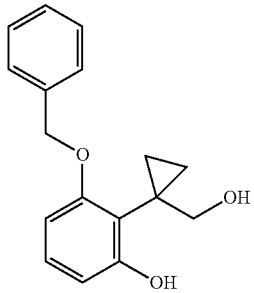 [SMILES: OCC1(c2c(O)cccc2OCc2ccccc2)CC1]

To a solution of 4-benzyloxyspiro[benzofuran-3,1'-cyclopropane]-2-one (Intermediate 28, 42.4 g, 159.2 mmol) in dry tetrahydrofuran (300 mL), a 1M solution of lithium aluminium hydride in THF (79.6 ml, 79.6 mmol) was slowly added at 0° C. and the reaction mixture was stirred at the same temperature for 30 minutes. The reaction was quenched with ice, water (400 ml) and an aqueous 1 M solution of HCl (160 ml) and then diluted with ethyl acetate (700 ml). Phases were separated and the aqueous layer was back extracted with ethyl acetate (500 ml). The combined organic phases were washed with brine (600 ml), dried over Na₂SO₄, filtered and evaporated affording the title compound 3-benzyloxy-2-[1-(hydroxymethyl)cyclopropyl]phenol (43 g) which was used in the next step without further purification.

LC/MS: QC_3_MIN: Rt=2.148 min; m/z 271 [M+H]+, m/z 293 [M+Na]+, m/z 253 [M-OH]+.

Intermediate 30

4-benzyloxyspiro[2H-benzofuran-3,1'-cyclopropane]

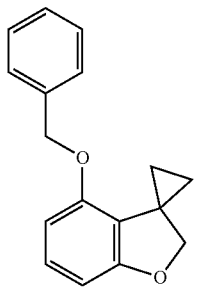 [SMILES: c1ccc(COc2cccc3c2C2(CC2)CO3)cc1]

To a solution of 3-benzyloxy-2-[1-(hydroxymethyl)cyclopropyl]phenol (Intermediate 29, 43 g, 159.1 mmol) in dimethyl carbonate (430 mL), potassium tert-butoxide (35.7 g, 318.1 mmol) was slowly added and the reaction mixture was stirred at 85° C. for 3.5 hours. The reaction mixture was cooled to room temperature, concentrated under vacuum up to 150 mL, diluted with MTBE (400 ml) and washed with water (400 ml). Phases were separated and the aqueous layer was back extracted with MTBE (250 ml). The combined organic layers were washed with brine (350 ml), dried over Na₂SO₄, filtered and concentrated affording the title compound 4-benzyloxyspiro[2H-benzofuran-3,1'-cyclopropane] (40 g) that was used in the next step without further purification.

LC/MS: QC_3_MIN: Rt=2.457 min; m/z 253 [M+H]+.

Intermediate 31 (Intermediate 85 WO2012/076877)

1 spiro[2H-benzofuran-3,1'-cyclopropane]-4-ol

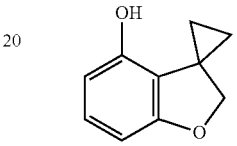

The reaction was done in two runs using 20 g of starting material each.

To a mixture of 4-benzyloxyspiro[2H-benzofuran-3,1'-cyclopropane](Intermediate 30, 20 g, 79.27 mmol) and ammonium formate (24.99 g, 396.34 mmol) in ethanol (160 ml), palladium 5% wt. on carbon (2.0 g) was added and the reaction mixture was stirred at 80° C. for 10 minutes. After cooling, the catalyst was filtered off through a cellulose pad and the filtrate was concentrated under vacuum up to −20 ml. The residues coming from the two reactions were combined and the mixture was diluted with ethyl acetate (300 ml) and washed three times with water (3×200 ml) and then with brine (200 ml). The two phases were separated and the organic one was dried over Na₂SO₄ and concentrated under vacuum. The residue was purified by flash chromatography (Biotage System) on silica gel using Cyclohexane: Ethyl acetate from 99:1 to 85:15 as eluent affording spiro [2H-benzofuran-3,1'-cyclopropane]-4-ol (17.75 g) as white solid.

LC/MS: QC_3_MIN: Rt=1.723 min; m/z 163 [M+H]+.

Intermediate 32 tert-butyl N-[(1S)-1-carbamoylpropyl]carbamate

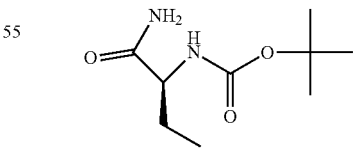

The title compound was synthesized following the same methodology used for the synthesis of Intermediate 7 replacing (2R)-2-(tert-butoxycarbonylamino)butanoic acid with (2S)-2-(tert-butoxycarbonylamino)butanoic acid LC/MS: QC_3_MIN: m/z 147 [M-tBu+H]+, m/z 427 [2M+Na]+

Intermediate 33 tert-butyl N-[(1S)-1-[[5-(7-methylspiro[2H-benzo-furan-3,1'-cyclopropane]-4-yl)oxypyrazin-2-yl]carbamoyl]propyl]carbamate

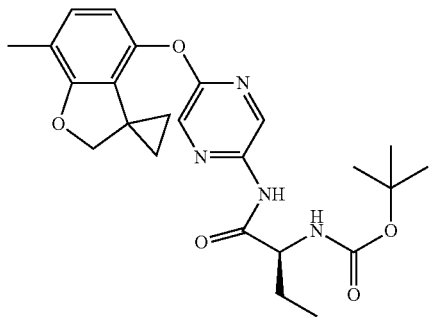 [SMILES: CC[C@H](NC(=O)OC(C)(C)C)C(=O)Nc1cnc(Oc2ccc(C)c3c2C2(CC2)CO3)cn1]

The title compound was synthesized following the "route 1" methodology used for the synthesis of Intermediate 9 replacing tert-butyl N-[(1R)-1-carbamoylpropyl]carbamate (Intermediate 7) with tert-butyl N-[(1S)-1-carbamoylpropyl]carbamate (Intermediate 32).

LC/MS: QC_3_MIN: Rt=2.65 min; m/z 455 [M+H]+.

Intermediate 34

(2S)-2-amino-N-[5-(7-methylspiro[2H-benzofuran-3,1'-cyclopropane]-4-yl)oxypyrazin-2-yl]butanamide

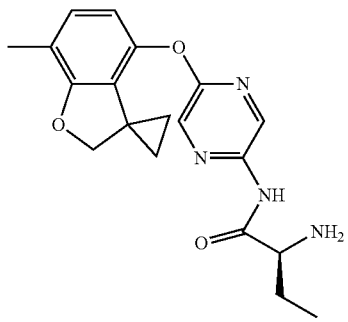 [SMILES: CC[C@H](N)C(=O)Nc1cnc(Oc2ccc(C)c3c2C2(CC2)CO3)cn1]

The title compound was synthesized following the same methodology used for the synthesis of Intermediate 13 replacing tert-butyl N-[(1R)-1-[[5-(7-methylspiro[2H-benzofuran-3,1'-cyclopropane]-4-yl)oxypyrazin-2-yl]carbamoyl]propyl]carbamate (Intermediate 9) with tert-butyl N-[(1S)-1-[[5-(7-methylspiro[2H-benzofuran-3,1'-cyclopropane]-4-yl)oxypyrazin-2-yl]carbamoyl]propyl]carbamate (Intermediate 33) LC/MS: QC_3_MIN: Rt=1.98 min; m/z 355 [M+H]+.

Example 1 Route 1

5,5-dimethyl-3-[5-(7-methylspiro[2H-benzofuran-3,1'-cyclopropane]-4-yl)oxypyrazin-2-yl]imidazolidine-2,4-dione

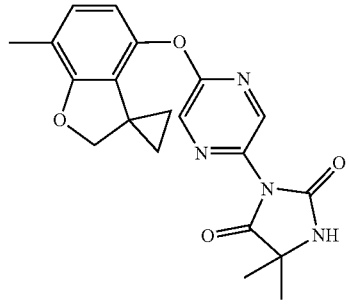 [SMILES: Cc1ccc(Oc2cnc(N3C(=O)NC(C)(C)C3=O)cn2)c2c1OCC21CC1]

To a solution of 2-bromo-5-(7-methylspiro[2H-benzofuran-3,1'-cyclopropane]-4-yl)oxy-pyrazine (Intermediate 1, 30 mg, 0.069 mmol) in N,N-dimethylacetamide (1 mL) 5,5-dimethylimidazolidine-2,4-dione (44.4 mg, 0.345 mmol) and copper (I) oxide (5 mg, 0.035 mmol) were added. The flask was flushed with nitrogen gas and left stirring overnight at 135° C. The reaction was diluted with EtOAc (10 mL) and first washed with an aqueous saturated solution of ammonium chloride (20 mL) and then brine (20 mL). The organic layer was collected, dried with sodium sulphate and evaporated to dryness. The residue was then purified using flash column chromatography using cyclohexane:ethyl acetate from 80:20 to 40:60 as eluent to afford 5,5-dimethyl-3-[5-(7-methylspiro[2H-benzofuran-3,1'-cyclopropane]-4-yl)oxypyrazin-2-yl]imidazolidine-2,4-dione (17 mg) as a white solid.

$^1$H-NMR (400 MHz; DMSO-d6): δ ppm 8.72 (bs, 1H), 8.51 (d, 1H), 8.30 (d, 1H), 6.95 (dd, 1H), 6.53 (d, 1H), 4.46 (s, 2H), 2.14 (s, 3H), 1.42 (s, 6H), 1.07-1.14 (m, 2H), 0.89-0.95 (m, 2H).

The following compounds were prepared using the foregoing methodology, replacing 2-bromo-5-(7-methylspiro[2H-benzofuran-3,1'-cyclopropane]-4-yl)oxy-pyrazine (Intermediate 1) with the appropriate bromopyrazine and 5,5-dimethylimidazolidine-2,4-dione with the appropriate hydantoin. Final products were purified by flash-chromatography (Silica cartridge; Cyclohexane/EtOAc or other appropriate solvent system) and/or reverse chromatography (C-18 cartridge; water/acetonitrile or other appropriate solvent system).

| Ex. | Structure | Name | Bromopyrazine | Hydantoin | LCMS/NMR |
|---|---|---|---|---|---|
| 2 | 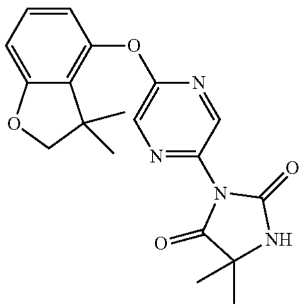 [SMILES: CC1(C)NC(=O)N(c2cnc(Oc3cccc4c3C(C)(C)CO4)cn2)C1=O] | 3-[5-[(3,3-dimethyl-2H-benzofuran-4-yl)oxy]pyrazin-2-yl]-5,5-dimethyl-imidazolidine-2,4-dione | 2-bromo-5-[(3,3-dimethyl-2H-benzofuran-4-yl)oxy]pyrazine (Intermediate 4) | 5,5-dimethyl-imidazolidine-2,4-dione | LC/MS: QC_3_MIN: Rt = 2.288 min; m/z 369 [M + H]+. 1H-NMR (500 MHz; DMSO-d6): δ ppm 8.73 (bs, 1H), 8.60 (d, 1H), 8.32 (d, 1H), 7.17 (dd, 1H), 6.70 (d, 1H), 6.66 (d, 1H), 4.23 (s, 2H), 1.42 (s, 6H), 1.28 (s, 6H). |
| 3 | 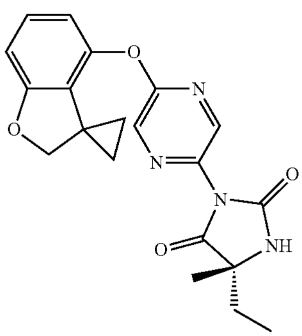 [SMILES: CC[C@@]1(C)NC(=O)N(c2cnc(Oc3cccc4c3C3(CC3)CO4)cn2)C1=O] | (5R)-5-ethyl-5-methyl-3-(5-spiro[2H-benzofuran-3,1'-cyclopropane]-4-yloxypyrazin-2-yl)imidazolidine-2,4-dione | 2-bromo-5-spiro[2H-benzofuran-3,1'-cyclopropane]-4-yloxy-pyrazine (Intermediate 2) | (5R)-5-ethyl-5-methyl-imidazolidine-2,4-dione (Intermediate 17) | LC/MS: QC_3_MIN: Rt = 2.228 min; m/z 381 [M + H]+. |

Example 1 Route 2

5,5-dimethyl-3-[5-(7-methylspiro[2H-benzofuran-3,1'-cyclopropane]-4-yl)oxypyrazin-2-yl]imidazolidine-2,4-dione

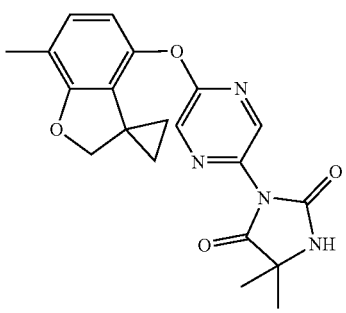 [SMILES: Cc1ccc(Oc2cnc(N3C(=O)NC(C)(C)C3=O)cn2)c2c1OCC21CC1]

To a solution of 3-(5-chloropyrazin-2-yl)-5,5-dimethyl-imidazolidine-2,4-dione (Intermediate 5, 20 mg, 0.083 mmol) and 7-methylspiro[2H-benzofuran-3,1'-cyclopropane]-4-ol (Intermediate 156 WO2012076877, 22 mg, 0.125 mmol) in acetonitrile (1 mL), dipotassium carbonate (17.2 mg, 0.12 mmol) was added. The reaction mixture was stirred overnight at 60° C. and then for 3 h at 80° C. The reaction mixture was concentrated under vacuum and the crude was purified by flash chromatography on silica gel (BIOTAGE SYSTEM) using a SNAP 10 g as column and Chexane/EtOAc from 80/20 to 20/80 as eluent. The fraction were still impure and they were purified by reverse chromatography using a SNAP C-18 as column and H2O/ACN from 95/5 to 5/95 as eluent affording 5,5-dimethyl-3-[5-(7-methylspiro[2H-benzofuran-3,1'-cyclopropane]-4-yl)oxypyrazin-2-yl]imidazolidine-2,4-dione (9.4 mg) as a white solid. LC/MS: QC_3_MIN: Rt=2.224 min; m/z 381 [M+H]+.

The following compounds were prepared using the foregoing methodology, replacing 7-methylspiro[2H-benzofuran-3,1'-cyclopropane]-4-ol with the appropriate phenol and use 3-(5-chloropyrazin-2-yl)-5,5-dimethyl-imidazolidine-2,4-dione (Intermediate 5) or replace it with the appropriate chloropyrazine intermediate. Final products were purified by flash-chromatography (Silica cartridge; Cyclohexane/EtOAc or other appropriate solvent system) and/or reverse chromatography (C-18 cartridge; water/acetonitrile or other appropriate solvent system).

| Ex. | Structure | Name | Phenol | Chloropyrazine intermediate | LCMS/NMR |
|---|---|---|---|---|---|
| 4 | 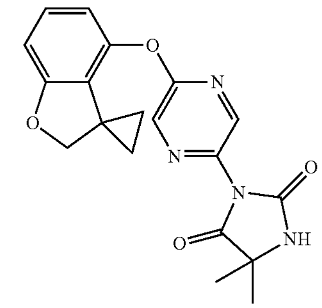 [SMILES: CC1(C)NC(=O)N(c2cnc(Oc3cccc4c3C3(CC3)CO4)cn2)C1=O] | 5,5-dimethyl-3-(5-spiro[2H-benzofuran-3,1'-cyclopropane]-4-yloxypyrazin-2-yl)imidazolidine-2,4-dione | spiro[2H-benzofuran-3,1'-cyclopropane]-4-ol (Intermediate 85, WO2012/076877) | 3-(5-chloropyrazin-2-yl)-5,5-dimethyl-imidazolidine-2,4-dione (Intermediate 5) | LC/MS: QC_3_MIN: Rt = 2.085 min; m/z 367 [M + H]+. $^1$H-NMR (500 MHz; DMSO-d6): δ ppm 8.73 (bs, 1H), 8.54 (d, 1H), 8.32 (d, 1H), 7.11 (dd, 1H), 6.71 (d, 1H), 6.62 (d, 1H), 4.46 (s, 2H), 1.42 (s, 6H), 1.12-1.16 (m, 2H), 0.92-0.97 (m, 5H). |
| 5 | 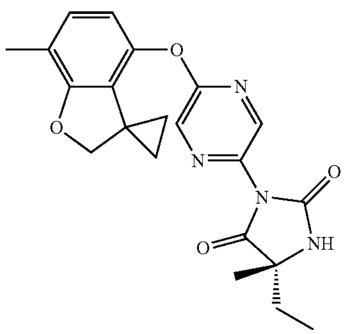 [SMILES: CC[C@@]1(C)NC(=O)N(c2cnc(Oc3ccc(C)c4c3C3(CC3)CO4)cn2)C1=O] | (5R)-5-ethyl-5-methyl-3-[5-(7-methylspiro[2H-benzofuran-3,1'-cyclopropane]-4-yl)oxypyrazin-2-yl]imidazolidine-2,4-dione | 7-methylspiro[2H-benzofuran-3,1'-cyclopropane]-4-ol (Intermediate 156 WO2012/076877) | 5R)-3-(5-chloropyrazin-2-yl)-5-ethyl-5-methyl-imidazolidine-2,4-dione (Intermediate 6) | LC/MS: QC_3_MIN: Rt = 2.361 min; m/z 395 [M + H]+. $^1$H-NMR (500 MHz; DMSO-d6): δ ppm 8.64 (bs, 1H), 8.48 (d, 1H), 8.25 (d, 1H), 6.91 (dd, 1H), 6.49 (d, 1H), 4.42 (s, 2H), 2.11 (s, 3H), 1.71-1.79 (m, 1H), 1.60-1.68 (m, 1H), 1.38 (s, 3H), 1.02-1.09 (m, 2H), 0.82-0.92 (m, 5H). |
| 6 | 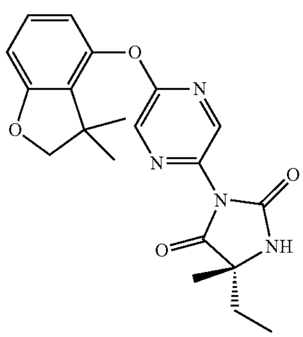 [SMILES: CC[C@@]1(C)NC(=O)N(c2cnc(Oc3cccc4c3C(C)(C)CO4)cn2)C1=O] | (5R)-3-[5-[(3,3-dimethyl-2H-benzofuran-4-yl)oxy]pyrazin-2-yl]-5-ethyl-5-methyl-imidazolidine-2,4-dione | 3,3-dimethyl-2H-benzofuran-4-ol (Intermediate 50 WO2012/076877 | 5R)-3-(5-chloropyrazin-2-yl)-5-ethyl-5-methyl-imidazolidine-2,4-dione (Intermediate 6) | LC/MS: QC_3_MIN: Rt = 2.008 min; m/z 383 [M + H]+. |
| 7 | 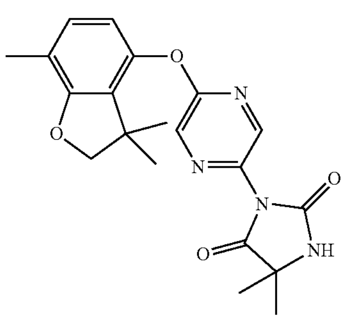 [SMILES: Cc1ccc(Oc2cnc(N3C(=O)NC(C)(C)C3=O)cn2)c2c1OCC2(C)C] | 5,5-dimethyl-3-[5-[(3,3,7-trimethyl-2H-benzofuran-4-yl)oxy]pyrazin-2-yl]imidazolidine-2,4-dione | 3,3,7-trimethyl-2H-benzofuran-4-ol (Intermediate 184 WO2012/076877) | 3-(5-chloropyrazin-2-yl)-5,5-dimethyl-imidazolidine-2,4-dione (Intermediate 5) | LC/MS: QC_3_MIN: Rt = 2.025 min; m/z 383 [M + H]+. |

| Ex. | Structure | Name | Phenol | Chloropyrazine intermediate | LCMS/NMR |
|---|---|---|---|---|---|
| 8 | 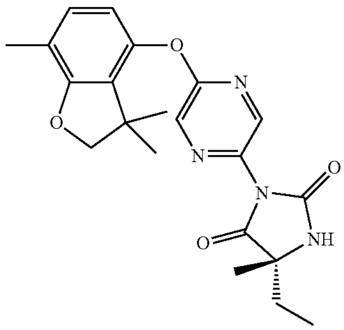 [SMILES: CC[C@@]1(C)NC(=O)N(c2cnc(Oc3ccc(C)c4c3C(C)(C)CO4)cn2)C1=O] | (5R)-5-ethyl-5-methyl-3-[5-[(3,3,7-trimethyl-2H-benzofuran-4-yl)oxy]pyrazin-2-yl]imidazolidine-2,4-dione | 3,3,7-trimethyl-2H-benzofuran-4-ol (Intermediate 184 WO2012/076877 | (5R)-3-(5-chloropyrazin-2-yl)-5-ethyl-5-methyl-imidazolidine-2,4-dione (Intermediate 6) | LC/MS: QC_3_MIN: Rt = 2.111 min; m/z 397 [M + H]+. |

Example 9 (route 1)

(5R)-5-ethyl-3-[5-(7-methylspiro[2H-benzofuran-3,1'-cyclopropane]-4-yl)oxypyrazin-2-yl]imidazolidine-2,4-dione

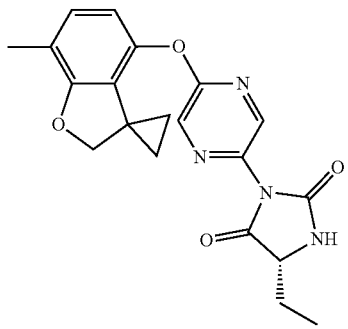 [SMILES: CC[C@H]1NC(=O)N(c2cnc(Oc3ccc(C)c4c3C3(CC3)CO4)cn2)C1=O]

A mixture of (2R)-2-amino-N-[5-(7-methylspiro[2H-benzofuran-3,1'-cyclopropane]-4-yl)oxypyrazin-2-yl]butanamide (Intermediate 13, 13 mg, 0.037 mmol) and N,N-diethylethanamine (11 mg, 0.11 mmol) in dichloromethane (2 mL) was cooled to 0° C. A solution of bis(trichloromethyl) carbonate (4.5 mg, 0.015 mmol) in dichloromethane (0.5 mL) was added dropwise and the reaction mixture was stirred for 1 hour at the same temperature. Additional bis(trichloromethyl) carbonate (1.5 mg) in dichloromethane (0.5 mL) was added and stirring continued for 30 minutes. The mixture was allowed to warm to room temperature. The reaction mixture was diluted with dichloromethane (20 ml) and the organic phase was washed with an aqueous solution 0.1 N HCl (20 ml) and then with brine (20 ml). Phases were separated and the organic layer was dried over Na$_2$SO$_4$, filtered and evaporated. The residue was purified by reverse phase chromatography using a SNAP C-18 column, eluting with water:acetonitrile from 90:10 to 0:100. The appropriate fractions were combined and evaporated to dryness, affording (5R)-5-ethyl-3-[5-(7-methylspiro[2H-benzofuran-3,1'-cyclopropane]-4-yl)oxypyrazin-2-yl]imidazolidine-2,4-dione (7.5 mg) as a white solid.

LC/MS: QC_3_MIN: Rt=2.305 min; m/z 381 [M+H]+. Enantiomeric purity was confirmed as >95% using Chiral Control method.

Example 9 (route 2)

(5R)-5-ethyl-3-[5-(7-methylspiro[2H-benzofuran-3,1'-cyclopropane]-4-yl)oxypyrazin-2-yl]imidazolidine-2,4-dione

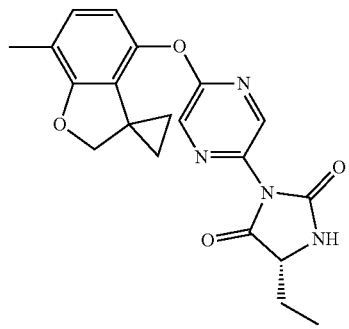 [SMILES: CC[C@H]1NC(=O)N(c2cnc(Oc3ccc(C)c4c3C3(CC3)CO4)cn2)C1=O]

To a solution of (2R)-2-amino-N-[5-(7-methylspiro[2H-benzofuran-3,1'-cyclopropane]-4-yl)oxypyrazin-2-yl]butanamide (Intermediate 13, 21 g, 59.26 mmol) in ethyl acetate (500 mL) 1-1'-carbonyldiimidazole (10.57 g, 65.18 mmol) was added in 5 portions of about 2 g each, and stirred at room temperature for 4 h. The reaction was quenched with ice and an aqueous 0.2N solution of HCl (250 ml) was added. The two phases were separated and the organic layer was washed with an aqueous 0.2N solution of HCl (250 ml) and with brine (200 ml), then dried with sodium sulphate, filtered and evaporated to dryness. The crude was split into 4 aliquots of ~4.2 g each and each aliquot was purified by flash chromatography on silica gel using a SNAP (100G) as column and Cyclohexane/Ethyl acetate from 80/20 to 20/80 as eluent. The desired fractions from each run were collected and the solvent evaporated to dryness. The obtained light-yellow solid was suspended in a solution of Cyclohexane/Ethyl acetate (1/1, 3 volumes) (90 ml) and stirred for 2 h at 50° C. The mixture was then allowed to cool to room temperature and filtered under vacuum. The wet cake was washed with ice cold cyclohexane (15 ml), the solid was collected and dried to afford the title compound (5R)-5-ethyl-3-[5-(7-methylspiro[2H-benzofuran-3,1'-cyclopropane]-4-yl)oxypyrazin-2-yl]imidazolidine-2,4-dione (13.6 g) as a white solid.

¹H-NMR (500 MHz; DMSO-d6): b ppm 8.69 (bs, 1H), 8.52 (d, 1H), 8.26 (d, 1H), 6.94 (d, 1H), 6.53 (d, 1H), 4.46 (s, 2H), 4.26-4.30 (m, 1H), 2.14 (s, 3H), 1.77-1.86 (m, 1H), 1.65-1.76 (m, 1H), 1.07-1.12 (m, 2H), 0.90-0.99 (m, 5H).

The following compounds were prepared using the foregoing methodology (either route 1 or route 2), replacing (2R)-2-amino-N-[5-(7-methylspiro[2H-benzofuran-3,1'-cyclopropane]-4-yl)oxypyrazin-2-yl]butanamide (Intermediate 13) with the appropriate butanamide. Final products were purified by flash-chromatography (Silica cartridge; Cyclohexane/EtOAc or other appropriate solvent system) and/or reverse chromatography (C-18 cartridge; water/acetonitrile or other appropriate solvent system).

| Ex. | Structure | Name | Butanamide | LCMS/NMR |
|---|---|---|---|---|
| 10 | 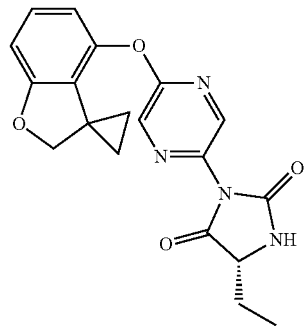 [SMILES: CC[C@H]1NC(=O)N(c2cnc(Oc3cccc4c3C3(CC3)CO4)cn2)C1=O] | (5R)-5-ethyl-3-(5-spiro[2H-benzofuran-3,1'-cyclopropane]-4-yloxypyrazin-2-yl) imidazolidine-2,4-dione | (2R)-2-amino-N-(5-spiro[2H-benzofuran-3,1'-cyclopropane]-4-yloxypyrazin-2-yl)butanamide (Intermediate 14) | LC/MS: QC_3_MIN: Rt = 2.081 min; m/z 367 [M + H]+. Enantiomeric purity was confirmed as >95% using Chiral Control method. ¹H-NMR (500 MHz; DMSO-d6): δ ppm 8.70 (bs, 1H), 8.55 (d, 1H), 8.27 (d, 1H), 7.11 (dd, 1H), 6.71 (dd, 1H), 6.62 (dd, 1H), 4.46 (s, 2H), 4.27-4.31 (m, 1H), 1.76-1.87 (m, 1H), 1.65-1.76 (m, 1H), 1.11-1.17 (m, 2H), 0.92-0.98 (m, 5H). |
| 11 | 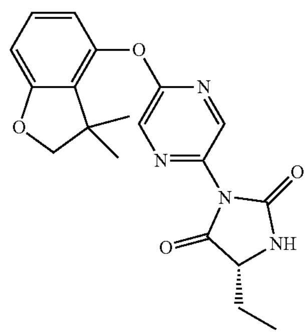 [SMILES: CC[C@H]1NC(=O)N(c2cnc(Oc3cccc4c3C(C)(C)CO4)cn2)C1=O] | (5R)-3-[5-[(3,3-dimethyl-2H-benzofuran-4-yl)oxy]pyrazin-2-yl]-5-ethyl-imidazolidine-2,4-dione | (2R)-2-amino-N-[5-[(3,3-dimethyl-2H-benzofuran-4-yl)oxy]pyrazin-2-yl]butanamide (Intermediate 16) | LC/MS: QC_3_MIN: Rt = 2.142 min; m/z 369 [M + H]+. |
| 12 | 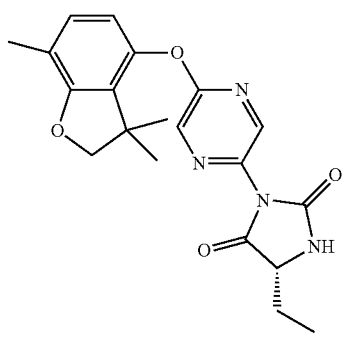 [SMILES: CC[C@H]1NC(=O)N(c2cnc(Oc3ccc(C)c4c3C(C)(C)CO4)cn2)C1=O] | (5R)-5-ethyl-3-[5-[(3,3,7-trimethyl-2H-benzofuran-4-yl)oxy]pyrazin-2-yl]imidazolidine-2,4-dione | (2R)-2-amino-N-[5-[(3,3,7-trimethyl-2H-benzofuran-4-yl)oxy]pyrazin-2-yl]butanamide (Intermediate 15) | LC/MS: QC_3_MIN: Rt = 2.111 min; m/z 383 [M + H]+. |
| 13 | 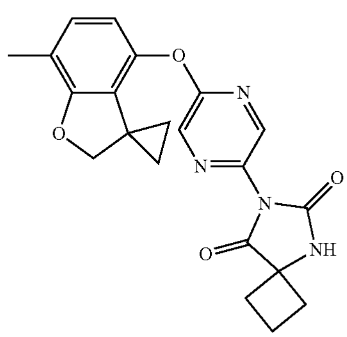 [SMILES: Cc1ccc(Oc2cnc(N3C(=O)NC4(CCC4)C3=O)cn2)c2c1OCC21CC1] | 7-[5-(7-methylspiro[2H-benzofuran-3,1'-cyclopropane]-4-yl)oxypyrazin-2-yl]-5,7-diazaspiro[3.4]octane-6,8-dione | 1-amino-N-[5-(7-methylspiro[2H-benzofuran-3,1'-cyclopropane]-4-yl)oxypyrazin-2-yl]cyclobutanecarboxamide (Intermediate 20) | LC/MS: QC_3_MIN: Rt = 2.309 min; 393 m/z [M + H]+. |

| Ex. | Structure | Name | Butanamide | LCMS/NMR |
|---|---|---|---|---|
| 14 | 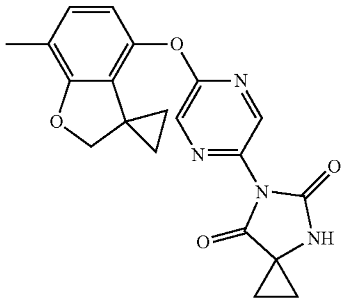 [SMILES: Cc1ccc(Oc2cnc(N3C(=O)NC4(CC4)C3=O)cn2)c2c1OCC21CC1] | 6-[5-(7-methylspiro[2H-benzofuran-3,1'-cyclopropane]-4-yl)oxypyrazin-2-yl]-4,6-diazaspiro[2.4]heptane-5,7-dione | 1-amino-N-[5-(7-methylspiro[2H-benzofuran-3,1'-cyclopropane]-4-yl)oxypyrazin-2-yl]cyclopropanecarboxamide | LC/MS: QC_3_MIN: Rt = 2.236 min; 379 m/z [M + H]+. |

Example 15

(5S)-5-ethyl-3-[5-(7-methylspiro[2H-benzofuran-3,1'-cyclopropane]-4-yl)oxypyrazin-2-yl]imidazolidine-2,4-dione

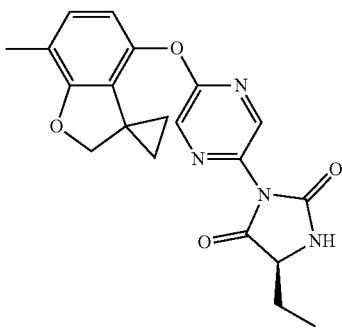 [SMILES: CC[C@@H]1NC(=O)N(c2cnc(Oc3ccc(C)c4c3C3(CC3)CO4)cn2)C1=O]

The title compound was synthesized following the "route 1" methodology used for the synthesis of Intermediate 9 replacing (2R)-2-amino-N-[5-(7-methylspiro[2H-benzofuran-3,1'-cyclopropane]-4-yl)oxypyrazin-2-yl]butanamide (Intermediate 13) with (2S)-2-amino-N-[5-(7-methylspiro[2H-benzofuran-3,1'-cyclopropane]-4-yl)oxypyrazin-2-yl]butanamide (Intermediate 34)

LC/MS: QC_3_MIN: Rt=2.29 min; m/z 381 [M+H]+.

Biological Examples

Biological Example 1: Measurement of Kv3.1, Kv3.2 and Kv3.3 Channel Modulation The ability of the compounds of the invention to modulate the voltage-gated potassium channel subtypes Kv3.3/Kv3.2/Kv3.1 may be determined using the following assay. Analogous methods may be used to investigate the ability of the compounds of the invention to modulate other channel subtypes.

Cell Biology

To assess compound effects on human Kv3.3 channels (hKv3.3), a stable cell line expressing human Kv3.3 channels is created by transfecting Chinese Hamster Ovary (CHO)-K1 cells with a pBacMire_KCNC-3 vector. Cells are cultured in DMEM/F12 (Gibco) supplemented with 10% Foetal Bovine Serum (Gibco), 1× non-essential amino acids (Invitrogen) and geneticin (G418) 400 microg/mL. Cells are grown and maintained at 37° C. in a humidified environment containing 5% $CO_2$ in air.

To assess compound effects on human Kv3.2 channels (hKv3.2), a stable cell line expressing human Kv3.2 channels (hKv3.2) is created by transfecting CHO-K1 cells with a pCIH5-hKv3.2 vector. Cells are cultured in DMEM/F12 medium supplemented by 10% Foetal Bovine Serum, 1× non-essential amino acids (Invitrogen) and 500 ug/ml of Hygromycin-B (Invitrogen). Cells are grown and maintained at 37° C. in a humidified environment containing 5% $CO_2$ in air.

To assess compound effects on human Kv3.1 channels (hKv3.1):

Human embryonic kidney (HEK)-hKv3.1 cell line is generated by transfecting HEK-293 cells with an expression vector with human Kv3.1 (NM_004976.4). Cells are cultured with MEM supplemented with 10% Heat-Inactivated FBS, 2 mM L-glutamine, 1% Penicillin-Streptomycin, and 0.6 mg/ml of Geneticin (G418). HEK-hKv3.1b cells were amplified in T175 cm2 flask at 37° C. with 5% CO2, using MEM amplification medium, containing the G418 selection antibiotic (0.6 mg/ml). Cells were detached every 3-4 days, using DPBS to wash twice the flask, then TrypLE to dislodge the cells, and re-plated at a density of 2-4×106 cells/flask.

Cell Preparation for IonWorks Quattro™ Experiments

The day of the experiment, cells are removed from the incubator and the culture medium removed. Cells are washed with 5 ml of Dulbecco's PBS (DPBS) calcium and magnesium free and detached by the addition of 3 ml Versene (Invitrogen, Italy) followed by a brief incubation at 37° C. for 5 minutes. The flask is tapped to dislodge cells and 10 ml of DPBS containing calcium and magnesium is added to prepare a cell suspension. The cell suspension is then placed into a 15 ml centrifuge tube and centrifuged for 2 min at 1200 rpm. After centrifugation, the supernatant is removed and the cell pellet re-suspended in 4 ml of DPBS containing calcium and magnesium using a 5 ml pipette to break up the pellet. Cell suspension volume is then corrected to give a cell concentration for the assay of approximately 3 million cells per ml.

All the solutions added to the cells are pre-warmed to 37° C.

Electrophysiology

Ionworks

Experiments are conducted at r.t. using IonWorks Quattro™ planar array electrophysiology technology (Molecular Devices Corp.) with PatchPlate™ PPC. Stimulation protocols and data acquisition are carried out using a microcomputer (Dell Pentium 4). Planar electrode hole resistances (Rp) are determined by applying a 10 mV voltage step across each well. These measurements are performed before cell addition. After cell addition and seal formation, a seal test is performed by applying a voltage step from −80 mV to −70 mV for 160 ms. Following this, amphotericin-B solution is added to the intracellular face of the electrode to achieve intracellular access. Cells are held at −70 mV. Leak subtraction is conducted in all experiments by applying 50 ms hyperpolarizing (10 mV) prepulses to evoke leak currents followed by a 20 ms period at the holding potential before test pulses.

For hKv3.2 and hKv3.1, assays from the holding potential of −70 mV, a first test pulse at −15 mV was applied for 100 ms and after 100 ms at −70 mV a second pulse at +40 mV was applied for 50 ms. Cells were then maintained for 100 ms at −100 mV and another pulse from −70 mV to +40 mV (duration 50 ms) was applied to clamp later the voltage at −40 mV during 200 ms For hKv3.3 assays, from the holding potential of −70 mV, a first test pulse to 0 mV is applied for 500 ms and following a further 100 ms at −70 mV, a second pulse to 40 mV is applied for 200 ms. These longer test pulses are used to study inactivation of hKv3.3 channels. Test pulses protocol may be performed in the absence (pre-read) and presence (post-read) of the test compound. Pre- and post-reads may be separated by the compound addition followed by a 3 minute incubation.

Solutions and Drugs

The intracellular solution contains the following (in mM): K-gluconate 100, KCl 54, $MgCl_2$ 3.2, HEPES 5, adjusted to pH 7.3 with KOH. Amphotericin-B solution is prepared as 50 mg/ml stock solution in DMSO and diluted to a final working concentration of 0.1 mg/ml in intracellular solution. The external solution is Dulbecco's Phosphate Buffered Saline (DPBS) and contained the following (in mM): $CaCl_2$ 0.90, KCl 2.67, $KH_2PO_4$ 1.47, $MgCl·6H_2O$ 0.493, NaCl 136.9, $Na_3PO_4$ 8.06, with a pH of 7.4.

Compounds of use in the invention (or reference compounds such as N-cyclohexyl-N-[(7,8-dimethyl-2-oxo-1,2-dihydro-3-quinolinyl)methyl]-N-phenylurea) are dissolved in dimethylsulfoxide (DMSO) at a stock concentration of 10 mM. These solutions are further diluted with DMSO using a Biomek FX (Beckman Coulter) in a 384 compound plate. Each dilution (1 μL) is transferred to another compound plate and external solution containing 0.05% pluronic acid (66 μL) is added. 3.5 μL from each plate containing a compound of the invention is added and incubated with the cells during the IonWorks Quattro™ experiment. The final assay dilution is 200 and the final compound concentrations are in the range 50 μM to 50 nM.

Data Analysis

The recordings are analysed and filtered using both seal resistance (>20 MO) and peak current amplitude (>500 pA at the voltage step of 40 mV) in the absence of compound to eliminate unsuitable cells from further analysis. For hKv3.2 and hKv3.1 assays, paired comparisons of evoked currents between pre- and post-drug additions measured for the −15 mV voltage step are used to determine the positive modulation effect of each compound. Kv3 channel-mediated outward currents are measured determined from the mean amplitude of the current over the final 10 ms of the −15 mV voltage pulse minus the mean baseline current at −70 mV over a 10 ms period just prior to the −15 mV step. These Kv3 channel currents following addition of the test compound are then compared with the currents recorded prior to compound addition. Data are normalised to the maximum effect of the reference compound (50 microM of N-cyclohexyl-N-[(7,8-dimethyl-2-oxo-1,2-dihydro-3-quinolinyl)methyl]-N-phenylurea) and to the effect of a vehicle control (0.5% DMSO). The normalised data are analysed using ActivityBase or Excel software. The concentration of compound required to increase currents by 50% of the maximum increase produced by the reference compound ($EC_{50}$) is determined by fitting of the concentration-response data using a four parameter logistic function in ActivityBase. For hKv3.3 assays, paired comparisons of evoked currents between pre- and post-drug additions are measured for the 0 mV step, considering the peak current and the decay (inactivation) of the current over the duration of the 0 mv test pulse (500 ms).

N-cyclohexyl-N-[(7,8-dimethyl-2-oxo-1,2-dihydro-3-quinolinyl)methyl]-N-phenylurea is obtained from ASINEX (Registry Number: 552311-06-5).

| Ex. | Compound | Kv3.1 pEC50 | Kv3.1 max R % | Reference/LCMS |
|---|---|---|---|---|
| RE1 | 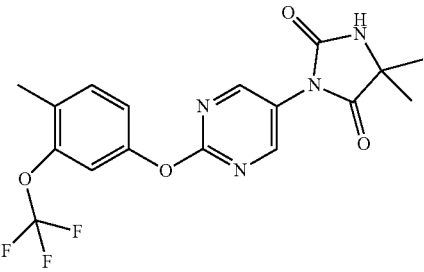 | 4.78 | 105 | Ex57 WO2011/069951 |

| Ex. | Compound | Kv3.1 pEC50 | Kv3.1 max R % | Reference/LCMS |
|---|---|---|---|---|
| RE2 | | 5.25 | 118 | Ex45 WO2011/069951 |
| RE3 | | 4.89 | 79 | LC/MS: QC_3_MIN: Rt = 2.376 min; m/z 396 [M + H]+. |
| RE4 | | <4.3 | 24 | LC/MS: QC_3_MIN: Rt = 2.346 min; m/z 397 [M + H]+. |
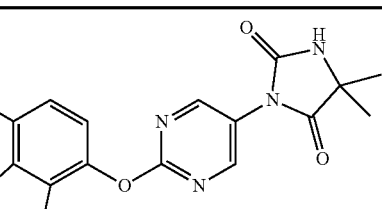
As shown by testing of RE1-RE4, the incorporation of a pyrazine ring can detrimentally impact the pEC50 and maxR of Kv3.1 modulators.
| Ex. | Compound | Kv3.1 pEC50 | Kv3.1 max R % | Reference/LCMS |
|---|---|---|---|---|
| RE5 | | 5.14 | 158 | Ex58 WO2012/076877 |
| RE6 | | 5.58 | 144 | Ex70 WO2012/076877 |
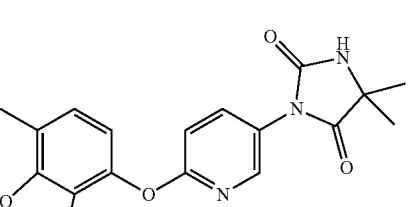

-continued

| Ex. | Compound | Kv3.1 pEC50 | Kv3.1 max R % | Reference/LCMS |
|---|---|---|---|---|
| RE7 | | 5.56 | 130 | Ex3 WO2017/103604 |
| RE8 | | 4.98 | 42 | LC/MS: QC_3_MIN: Rt = 2.224 min; m/z 381 [M + H]+. |
| RE9 | | <4.3 | 16 | LC/MS: QC_3_MIN: Rt = 2.043 min; m/z 381 [M + H]+. |
| RE10 | | <4.3 | 22 | LC/MS: QC_3_MIN: Rt = 2.29 min; m/z 381 [M + H]+. |
| 1+ | | 5.47 | 164 | Example 1 |

+n = 10. For n = 18, pEC50 was 5.56 and maxR % 152

As shown by testing of RE5-RE9 as compared to Example 1, the incorporation of a para-pyrazine ring in Example 1 unexpectedly results in high pEC50 and high maxR in the Kv3.1 assay. RE10 shows that a meta-pyrazine central ring has greatly reduced pEC50 and maxR as compared to the para-pyrazine of Example 1.

| Example | Kv3.1 pEC50 | Kv3.1 max R % |
|---|---|---|
| 1+ | 5.47 | 164 |
| 2 | 4.68 | 149 |
| 3 | 5.15 | 205 |

77
-continued
| Example | Kv3.1 pEC50 | Kv3.1 max R % |
|---|---|---|
| 4 | 5.17 | 170 |
| 5 | 5.69 | 149 |
| 6 | 4.75 | 165 |
| 7 | 5.12 | 134 |
| 8 | 5.29 | 119 |
| 9* | 5.88 | 172 |
| 10$ | 5.45 | 153 |
| 11 | 4.89 | 165 |
78
-continued
| Example | Kv3.1 pEC50 | Kv3.1 max R % |
|---|---|---|
| 12 | 5.56 | 118 |
| 13 | 5.09 | 165 |
| 14 | 5.51 | 145 |
†n = 10. For n = 18, pEC50 was 5.56 and maxR % 152
*n = 4. For n = 22, pEC50 was 5.90 and maxR % 146
$n = 2. For n = 26, pEC50 was 5.63 and maxR % 147
| Ex. | Compound | Kv3.1 PEC50 | Kv3.1 max R % | Reference/LCMS |
|---|---|---|---|---|
| RE11 | 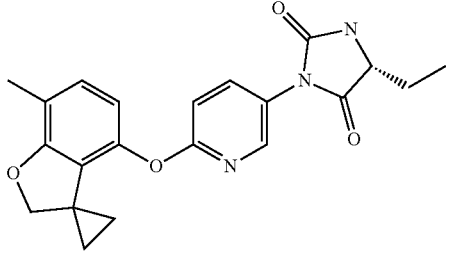 | 6.1 | 152 | Ex62 WO2012/076877 |
| RE12 | 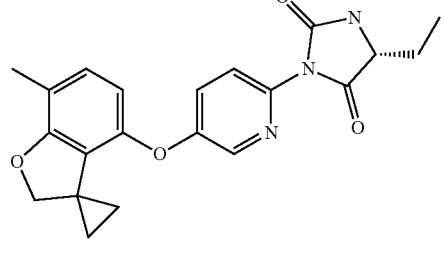 | 5.6 | 149 | Ex4 WO2017/102604 |
| 9 | 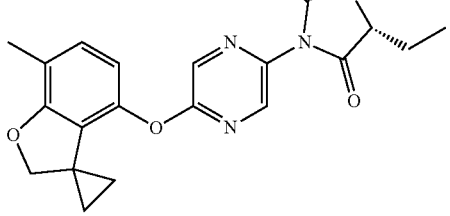 | 5.90 | 146 | Example 9 |
| RE13 | 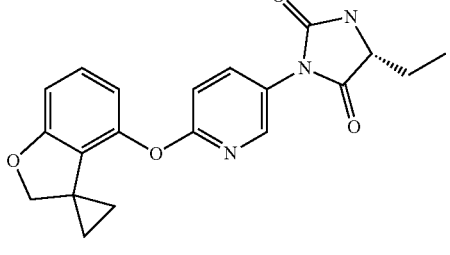 | 6.1 | 149 | Ex15 WO2012/076877 |

-continued

| Ex. | Compound | Kv3.1 PEC50 | Kv3.1 max R % | Reference/LCMS |
|---|---|---|---|---|
| RE14 | (structure) | 5.2 | 150 | Ex6 WO2017/102604 |
| 10 | (structure) | 5.63 | 147 | Example 10 |

All tested examples of the compounds of formula (I) are shown above and demonstrate good pEC50 and maxR properties in the Kv3.1 assay. Previous disclosures of Kv3.1 data for comparator compounds may differ slightly due to a lower number of measurements.

A secondary analysis of the data from the hKv3.1, hKv3.2 and hKv3.3 assays described in may be used to investigate the effect of the compounds on rate of rise of the current from the start of the depolarising voltage pulses. The magnitude of the effect of a compound can be determined from the time constant ($Tau_{act}$) obtained from a non-linear fit, using the equation given below, of the rise in Kv3.1, Kv3.2 and Kv3.3 currents following the start of the −15 mV depolarising voltage pulse.

$$Y=(Y0-Ymax)*\exp(-K*X)+Ymax$$

where:
- Y0 is the current value at the start of the depolarising voltage pulse;
- Ymax is the plateau current;
- K is the rate constant, and $Tau_{act}$ is the activation time constant, which is the reciprocal of K.

Similarly, the effect of the compounds on the time taken for Kv3.1, Kv3.2 or Kv3.3 currents to decay on closing of the channels at the end of the −15 mV depolarising voltage pulses can also be investigated. In this latter case, the magnitude of the effect of a compound on channel closing can be determined from the time constant ($Tau_{deact}$) of a non-linear fit of the decay of the current ("tail current") immediately following the end of the depolarising voltage pulse.

Kv3.1, Kv3.2 and Kv3.3 channels must activate and deactivate very rapidly in order to allow neurons to fire actions potentials at high frequency (Rudy et al., 2001). Slowing of activation is likely to delay the onset of action potential repolarisation; slowing of deactivation could lead to hyperpolarising currents that reduce the excitability of the neuron and delay the time before the neuron can fire a further action potential. Together these two slowing effects on channel activation and deactivation are likely to lead to a reduction rather than a facilitation of the neurons ability to fire at high frequencies. Thus compounds that have this slowing effect on the Kv3.1 and/or Kv3.2, and/or Kv3.3 channels will effectively behave as negative modulators of the channels, leading to a slowing of neuronal firing. This latter effect has been shown for certain of the compounds disclosed in International Patent Application Publication No. 2011/069951, where marked increases in $Tau_{act}$ can be observed from recordings made from "fast-firing" interneurons in the cortex of rat brain, using electrophysiological techniques, in vitro. The addition of the relevant compounds reduces the ability of the neurons to fire in response to trains of depolarising pulses at 300 Hz.

Therefore, although certain compounds may be identified act as positive modulators in the recombinant cell assay, those compounds which markedly increase the value of $Tau_{act}$ can reduce the ability of neurons in native tissues to fire at high frequency.

Biological Example 2: Determination of Blood and Brain Tissue Binding

Materials and Methods

Sprague Dawley rat whole blood, collected on the week of the experiment using K3-EDTA as an anti-coagulant, is diluted with isotonic phosphate buffer 1:1 (v/v). Sprague Dawley rat whole brain, stored frozen at −20° C., is thawed and homogenised in artificial cerebrospinal fluid (CSF) 1:2 (w/v).

An appropriate amount of test compound is dissolved in DMSO to give a 10 millimolar solution. Further dilutions, to obtain a 166.7 micromolar working solution are then prepared using 50% acetonitrile in MilliQ water. This working solution is used to spike the blood to obtain a final concentration of 0.5 micromolar in whole blood. Similarly, the working solution is used to spike brain samples to obtain a final concentration of 5 micromolar in whole brain. From these spiked blood and brain preparations, control samples (n=3), are immediately extracted and used to calculate the initial recovery of the test items.

150 microL of compound-free buffer (isotonic phosphate buffer for blood or artificial CSF buffer for brain) is dispensed in one half-well and 150 microL of spiked matrix (blood or brain) is loaded in the other half-well, with the two halves separated by a semi-permeable membrane. After an equilibration period of 5 h at 37° C., 50 microL of dialysed matrix (blood or brain) is added to 50 microL of corresponding compound-free buffer, and vice-versa for buffer, such that the volume of buffer to matrix (blood or brain) remains the same. Samples are then extracted by protein precipitation with 300 microL of acetonitrile containing rolipram (control for positive ionization mode) or diclofenac (control for negative ionization mode) as internal standards and centrifuged for 10 min at 3000 rpm. Supernatants are collected (100 microL), diluted with 27% AcN in MilliQ water (200 microL) and then injected into an HPLC-MS/MS or UPLC-MS/MS system to determine the concentration of test compound present.

Analysis

Blood and brain tissue binding are then determined using the following formulas:

Afu=Buffer/Blood or Afu=CSF/Brain

Where Afu=apparent fraction unbound; Buffer=analyte/internal standard ratio determined in the buffer compartment; Blood=analyte/internal standard ratio determined in the blood compartment; Brain=analyte/internal standard ratio determined in the brain compartment.

$$Fucr = \frac{1/D}{[(1/Afu - 1) + 1/D]}$$

where: fucr=Fraction unbound corrected; D=matrix dilution factor (D=2 for blood and D=3 for brain).
Then:

% Binding=(1−fucr)×100

% Unbound=100−% Bound

Brain/Blood Partition Ratio (Kbb) Determination

For compounds freely permeable across the blood/brain barrier (BBB), the unbound concentrations in blood and brain would be equivalent under steady-state distribution conditions. Therefore, the Kbb value could be calculated as:

Fu(blood)/Fu(brain)

which is expected to be equivalent to the brain-to-blood concentration ratio (Ct(brain)/Ct(blood)) if efflux pump transporters are not involved.

Results

Examples 1, 9 and 10, and certain comparator compounds, were tested in the above described methodology to determine the brain fraction unbound. The results were as follows:

| Ex. | Compound | Brain fraction unbound (%) |
|---|---|---|
| RE5 | | 5.1 |
| RE6 | | 2.8 |
| RE7 | | 2.3* |
| 1 | | 4.3 |
| RE11 | | 2.1 |

-continued

| Ex. | Compound | Brain fraction unbound (%) |
|---|---|---|
| RE12 | (structure) | 1.9 |
| 9 | (structure) | 3.0 |
| RE13 | (structure) | 6.2 |
| RE14 | (structure) | 5.8 |
| 10 | (structure) | 8.7 |

*Supernatant diluted with 18% AcN in water

Pyrazine compounds of the invention, demonstrated an increased brain fraction unbound as compared to their pyridine comparator compounds.

Biological Example 3: Determination of In Vivo Pharmacokinetic Parameters

Materials and Methods

Adult male rats (Charles River, Italy) are dosed with test compound orally at 1 mg/kg (5 ml/kg, in 5% v/v DMSO, 0.5% w/v HPMC in water) and intravenously at 0.5 mg/kg (2 ml/kg, in 5% v/v DMSO 40% w/v PEG400 in saline). After oral administration, blood samples are collected under deep Isofluorane anesthesia from the portal vein and heart of each rat (1 rat per time point). After intravenous administration, serial blood samples are collected from the lateral tail vein of each rat. A further group of rats (n=1 per test compound) receive a single intravenous administration of the PgP transport inhibitor, Elacridar (3 mg/kg) shortly before the oral administration of the test compound at 1 mg/kg, as above. Blood and brain samples are collected at a single timepoint of 0.5 h after dose administration for these animals. In all cases, blood samples are collected into potassium EDTA tubes.

Blood and brain samples can be assayed for test compound concentration using a method based on protein precipitation with acetonitrile followed by HPLC/MS-MS analysis with an optimized analytical method.

Analysis

The concentrations of test compound in blood (expressed as ng/ml) and brain (expressed as ng/g) at the different time points following either oral or intravenous dosing are analysed using a non-compartmental pharmacokinetic model using WinNonLin Professional version 4.1. The following parameters are derived:

Intravenous dosing: Maximum concentration over time (Cmax), integrated concentration over time (AUC), clearance (Clb), volume of distribution (Vss) and half-life (t1/2).

Oral dosing: Cmax, time of maximum concentration (Tmax), AUC, bioavailability (F %), fraction absorbed (Fa %), blood to brain ratio (AUC BB), and Fold-change in AUC BB in the presence of Elacridar.

Compounds of the invention may be expected to demonstrate good availability in brain tissue.

Biological Example 4: In Vitro Metabolic Stability Study in Human Hepatocytes

Methodology

The objective of this study was to determine metabolic stability in mixed gender human cryopreserved hepatocytes. Testosterone and 7-Hydroxycoumarin were used as positive controls for Phase I and Phase II metabolism, respectively.

Incubation medium was prepared by combining William's medium E, HEPES buffer 1 M and L-glutamine 200 mM in the following proportions: 88%, 10% and 2%, respectively (440 mL, 50 mL and 10 mL, respectively). The medium obtained was bubbled with carbogen (5% $CO_2$, 95% $O_2$) for 30 minutes prior to use. Cryopreserved hepatocytes were thawed and suspended in incubation medium pre-warmed at 37° C. Cells were centrifuged, re-suspended in medium and counted by means of a haemocytometer (Burker's chamber). Cell viability was measured using the Trypan Blue exclusion test.

Test compounds were separately dissolved in DMF to obtain 50 mM stock solutions that were further diluted in water/acetonitrile 50/50 (v/v) to obtain the corresponding 50 uM working solutions. Testosterone and 7-Hydroxy-Coumarin were dissolved in DMF in order to obtain a 50 mM Testosterone solution and 5 mM 7-Hydroxy-Coumarin solution. These solutions were then diluted in the incubation medium in order to obtain a 1 mM Testosterone working solution and a 500 uM 7-Hydroxy-Coumarin working solution.

10 µL of each working solution, i.e. 50 uM test compound, 1 mM Testosterone and 500 uM of 7-Hydroxy-Coumarin were added to 990 µL of 0.5×10$^6$ cell suspensions in order to obtain the final concentrations of 0.5 uM, 10 uM and 5 uM, respectively. The concentration of the organic solvent in each incubation was constant and <1% (v/v).

Test compounds were separately incubated at 0.5 uM for 0, 5, 10, 15, 20, 30, 45, 60, 90, 120, 150 and 180 min (12 time points) with mixed gender human cryopreserved hepatocytes at 37° C. in a 24 well plate. At each time point a robotic handling processor aspirated 50 µL of incubation mixture from each well and dispensed it into a refrigerated 96 well plate, containing 100 µL of acetonitrile with the corresponding internal standard 150 ng/mL to stop the reaction. Then an aliquot of water (120 uL) was added to equilibrate the organic solvent content at 37%. Samples were centrifuged (ca. 3500 g for 10 minutes) prior to LC MS/MS analysis.

Positive controls, Testosterone and 7-Hydroxy-Coumarin, were incubated in single (n=1) at 10 and 5 uM, respectively, for 0, 5, 10, 15, 20, 30, 45, 60, 90, 120, 150 and 180 min (12 time points) with mixed gender human cryopreserved hepatocytes at the same conditions reported above for the test items, to demonstrate Phase I and Phase II metabolism in the hepatocytes systems. At each time point a robotic handling processor aspirated 50 µL of incubation mixture from each well and dispensed it into a refrigerated 96 well plate, containing 100 µL of acetonitrile with Rolipram as internal standard to stop the reaction. Then an aliquot of water (120 uL) was added to equilibrate the organic solvent content at 37%. Samples were centrifuged (ca. 3500 g for 10 minutes) prior to LC MS/MS analysis.

Metabolic stability was calculated from the peak area ratio of the remaining test compound with internal standard versus time.

The intrinsic clearance (CLint) was determined from the first order elimination constant k (min$^{-1}$) (obtained from GraphPad by plotting the natural logarithm of the peak area ratio of the remaining test item with internal standard versus time), using the actual volume of the incubation V (mL), the amount of hepatocytes in the incubation M (million cells) and the hepatocellularity number per g liver Hn (120 for human).

$$CLint = k * \frac{V}{M} * \frac{Hn \times 10^6 \text{cells}}{\text{g liver}}$$

Values for CLint were expressed as mL/min/g liver.

| Ex. | Compound | Rate constant k (min$^{-1}$) | In vitro CI$_{int}$ (mL/min/g liver) |
|---|---|---|---|
| RE5 | | 0.002 | 0.31 |
| RE11 | | 0.02 | 3.58 |
| 9 | | 0.004 | 1.03 |

| Ex. | Compound | Rate constant k (min⁻¹) | In vitro CI$_{int}$ (mL/min/g liver) |
|---|---|---|---|
| RE13 | 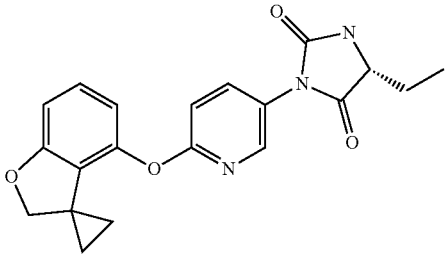 | 0.009 | 2.16 |
| 10 | 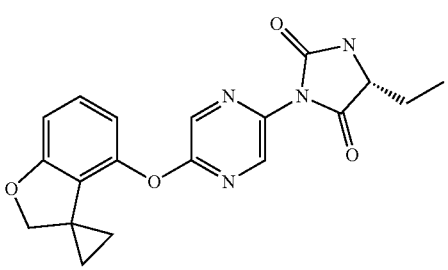 [SMILES: CC[C@H]1NC(=O)N(c2cnc(Oc3cccc4c3C3(CC3)CO4)cn2)C1=O] | 0.003 | 0.70 |

Examples 9 and 10 demonstrate low clearance compared to pyridine comparator compounds RE11 and RE13.

Biological Example 5: Ames Testing

Methodology

The objective of this in vitro study was to assess the potential of test articles to induce gene mutations in vitro in bacterial strains of *Salmonella typhimurium* (TA1535, TA1537, TA98 and TA100) and *Escherichia coli* WP2 uvrA (pKM101); test methodology was based on established procedures for bacterial mutagenicity testing, and assays were performed in the presence and absence of an exogenous mammalian oxidative metabolizing system (S9-mix).

The study was designed in accordance with national and international guidelines, to fulfil the requirements of regulatory authorities, for the toxicity testing of new drugs. The study design is in agreement with the following test guidelines:

ICH guideline M3(R2) on non-clinical safety studies for the conduct of human clinical trials and marketing authorisation for pharmaceuticals (CPMP/ICH/286/95, June 2009).

ICH Topic S2 (R1) Guidance on Genotoxicity Testing and Data Interpretation for Pharmaceuticals Intended for Human Use. June 2012.

Bacterial Strains

The following bacterial strains were used:

| Species | Strain | Genotype |
|---|---|---|
| *S. typhimurium* | TA1535 | hisG46 rfa Δ uvrB |
| *S. typhimurium* | TA1537 | hisC3076 rfa Δ uvrB |
| *S. typhimurium* | TA98 | hisD3052 rfa Δ uvrB (pKM101) |
| *S. typhimurium* | TA100 | hisG46 rfa Δ uvrB (pKM101) |

| Species | Strain | Genotype |
|---|---|---|
| *E. coli* | WP2 uvrA (pKM101) | TrpE Ochre uvrA (pKM101) |
| Source | Molecular Toxicology Incorporated, Boone, NC, USA (MolTox ™) | |
| Growth Phase | Late log phase | |

The strains TA1535, TA100, and WP2 uvrA pKM101 detect base change mutations. The strains TA1537 and TA98 detect frameshift mutations.

Bacteria inocula were used to prepare fresh cultures in 10 mL of nutrient broth (NB2, containing ampicillin for the pKM101 plasmid containing strains *S. typhimurium* strains TA98 and TA100 and *E. coli* WP2 uvrA (pKM101) to maintain the plasmid copy number). Bacteria were cultured for 10-12 hours in a shaking incubator at 37±2° C. to yield 1-2×10⁹ cells/mL.

The bacteria suspension was added to the Top Agar (containing trace amounts of the amino acids required for auxotrophy) at a volume of 100 uL.

Mammalian Oxidative Metabolizing System

Phenobarbital, 5 6 Benzoflavone induced rat liver post mitochondrial fraction (S9) from Molecular Toxicology Incorporated, USA (MolTox™) was used as an exogenous oxidative metabolizing system. Batches of S9 fraction stored as frozen aliquots at approximately −80° C. were thawed immediately prior to use. S9 mix was prepared by the addition of S9 (10% v/v) to a NADPH generating system, which included NADP (3.15 mg/mL), glucose 6 phosphate (1.5 mg/mL), and 2% v/v of a saline solution containing MgCl$_2$ (81.3 mg/mL) and KCl (123 mg/mL) in phosphate buffer pH 7.4. For treatment in the presence of S9 mix, S9 mix was used at a final volume of 500 uL/plate. For treatment in the absence of S9 mix, an equivalent volume of sterile phosphate buffer pH 7.4 was added in place of the S9 mix.

Positive Control Formulations

The following positive controls (supplied by MolTox™ through Trinova Biochem GmbH, Giessen, Germany and Sigma Aldrich, Milano, Italy) were used and formulated as follows:

| Bacterial Strain | Positive Control | Conc. (μg/plate) | Vehicle (Solvent) | S9-mix |
|---|---|---|---|---|
| TA98 | 2-Nitrofluorene (2NF) | 2 | Dimethyl Sulfoxide (DMSO) | No |
| TA1535, TA100 | Sodium Azide (NaAz) | 2 | $H_2O$ | No |
| TA1537 | ICR-191 | 1 | DMSO | No |
| WP2 uvrA (pKM101) | 4-Nitroquinoline-1-oxide (4NQO) | 1 | DMSO | No |
| TA98 | Benzo[a]pyrene (B[a]P) | 1.25 | DMSO | Yes |
| TA1535, TA1537, TA100, WP2 uvrA (pKM101) | 2-Aminoanthracene (2AAN) | 5 | DMSO | Yes |

Positive controls were prepared from frozen (approximately −20° C.) stock solutions and stored at ambient temperature during the use.

Test Articles

The test consisted of 4 replicate plates for vehicle (DMSO) controls and 2 replicate plates for the test article and positive controls, treated in the absence and in the presence of S9-mix. A range of test article concentrations starting from 5 ug/plate to 5000 ug/plate was tested, as follows:

| Species | Strain | Test Item Concentrations (ug/plate) | S9-mix |
|---|---|---|---|
| S. typhimurium | TA1535, TA1537, TA98 and TA100 | 5, 15, 50, 150, 500, 1500 and 5000 | No |
| E. coli | WP2 uvrA (pKM101) | | |
| S. typhimurium | TA1535, TA1537, TA98 and TA100 | | Yes |
| E. coli | WP2 uvrA (pKM101) | | |

The vehicle, test article and positive control formulations were added to plates at a volume of 100 uL/plate.

Plate Treatment and Incubation

Top agar was supplemented with trace amounts of histidine and biotin, or tryptophan, aliquoted (2 mL/plate), and maintained at 46±200. The appropriate bacterial suspension was added to 2 mL of top agar followed by the test article, or vehicle/positive control solutions, and sterile phosphate buffer pH 7.4 or S9-mix. This final treatment mixture was poured over minimal agar plates (Vögel Bonner plates) and incubated in the dark for approximately 64 hours at 37±2° C.

Plate Scoring and Analysis

At the end of the incubation period, plates were evaluated (by visual examination) for test article precipitation. Plates were scored electronically for bacterial colony formation using the colony counter ProtoCOL3 Synbiosis. Where test article precipitation occurred, the bacterial colony count for each strain was performed manually and halted at the lowest treatment concentration that did not interfere with the manual scoring.

The scoring was followed by the inspection of the plates for signs of toxicity (i.e. reduced growth/diminution of background lawn, the presence of pin dot/pseudorevertant colonies, and/or a reduction in colony numbers).

If the data for any treatment concentration show a response ≥2 times the concurrent vehicle control value for TA98, TA100, and WP2 uvrA (pKM101), or ≥3 times the concurrent vehicle control value for TA1535 and TA1537, in conjunction with a dose related response, the result should be considered positive. Results that only partially satisfy these criteria or where the data for any strain show a dose related response, but do not exceed the 2 or 3 fold threshold as detailed, are considered equivocal.

The following acceptance criteria were applied:

1. The highest concentration tested should be 5000 ug/plate, or limited by solubility of test item in the vehicle.
2. If the test item solubility is a limiting factor, the maximum concentration chosen for plate scoring would be the lowest concentration at which the test item precipitation is observed on treatment plates at the end of the incubation period and that does not interfere with the scoring.

If toxicity is a limiting factor, the maximum concentration evaluable for gene mutation would be the lowest concentration at which signs of significant bacterial toxicity are observed during plate scoring.

Results

| Ex. | Compound | Ames Result | Aniline | Ames Result |
|---|---|---|---|---|
| RE5 | | Non-mutagenic | Not tested | Not tested |
| RE6 | | Non-mutagenic | | Mutagenic for TA1535 in the presence of metabolic activation at 150 ug/plate |
| RE11 | | Non-mutagenic | | |
| 1 | | Non-mutagenic | | Non-mutagenic |
| 9 | | Non-mutagenic | | |

| Ex. | Compound | Ames Result | Aniline | Ames Result |
|---|---|---|---|---|
| 10 | (structure) | Non-mutagenic | 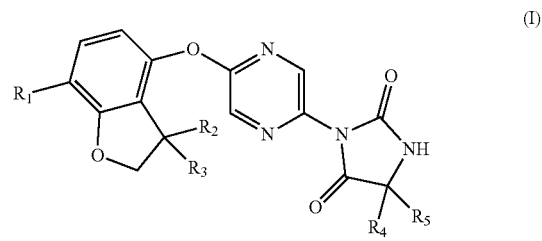 | Non-mutagenic |

The aniline associated with RE6/RE11, which has been shown to be a degradant under certain conditions, was found to be mutagenic. This finding presents a risk in the future development of RE6/RE11 and also for compounds which could produce related anilines (e.g. (5R)-5-ethyl-3-(6-spiro[2H-benzofuran-3,1'-cyclopropane]-4-yloxy-3-pyridyl)imidazolidine-2,4-dione, i.e. RE13). Compounds which may be distinguished on the basis of their associated anilines are advantageous.

Anilines for Examples 1, 9 and 10 are non-mutagenic, which may be expected to apply to other compounds of the invention which could produce related anilines.

Additional Animal Models

International Patent Application Publication No. 2011/069951, 2012/076877, 2012/168710, 2013/083994 2013/175215 and 2013/182851 (all incorporated by reference for the purpose of illustrating the potential utility of the compounds and providing animal models for the testing of compounds) demonstrate the activity of compounds which are modulators of Kv3.1 and Kv3.2 in animal models of seizure, hyperactivity, sleep disorders, psychosis, hearing disorders and bipolar disorders.

International Patent Application Publication No. 2013/175211 (incorporated by reference for the purpose of illustrating the potential utility of the compounds and providing animal models for the testing of compounds) demonstrates the efficacy of a compound which is a modulator of Kv3.1 and Kv3.2 in a model of acute noise-induced hearing loss in the chinchilla, and also evaluates the efficacy of the compound in a model of central auditory processing deficit and in a model of tinnitus.

Glait et al 2018, Anderson et al 2018 and Chamber et al 2018 demonstrate the efficacy of a modulator of Kv3.1 and Kv3.2 in hearing associated models.

International Patent Application Publication No. 2017/098254 (incorporated by reference for the purpose of illustrating the potential utility of the compounds and providing animal models for the testing of compounds) demonstrates the efficacy of a compound which is a modulator of Kv3.1 and Kv3.2 in models of neuropathic and inflammatory pain.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the claims which follow.

Clauses of the Invention:

Clause 1—A compound of formula (I):

(I) (structure)

wherein:
$R_1$ is H or methyl;
$R_2$ and $R_3$ are both methyl, or $R_2$ and $R_3$, together with the carbon atom to which they are attached, are a spirocyclopropyl ring;
$R_4$ is methyl or ethyl;
$R_5$ is H or methyl;
or $R_4$ and $R_5$, together with the carbon atom to which they are attached, form a $C_3$-$C_4$ spiro carbocyclyl;
or a salt and/or solvate and/or derivative thereof.

Clause 2—The compound according to clause 1 wherein $R_1$ is H.

Clause 3—The compound according to clause 1 wherein $R_1$ is methyl.

Clause 4—The compound according to any one of clauses 1 to 3, wherein $R_2$ and $R_3$ are a spiro cyclopropyl ring.

Clause 5—The compound according to any one of clauses 1 to 3, wherein $R_2$ is methyl and $R_3$ is methyl.

Clause 6—The compound according to any one of clauses 1 to 5, wherein $R_4$ is methyl.

Clause 7—The compound according to any one of clauses 1 to 5, wherein $R_4$ is ethyl.

Clause 8—The compound according to any one of clauses 1 to 7, wherein $R_5$ is H.

Clause 9—The compound according to any one of clauses 1 to 7, wherein $R_5$ is methyl.

Clause 10—The compound according to any one of clauses 1 to 9 wherein when $R_4$ and $R_5$ are different and they have the following stereochemical arrangement:

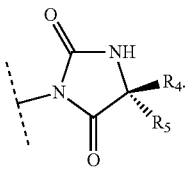

Clause 11—The compound according to any one of clauses 1 to 9 wherein when $R_4$ and $R_5$ are different and they have the following stereochemical arrangement:

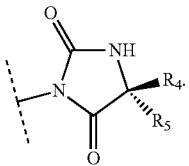

Clause 12—The compound according to any one of clauses 1 to 5, wherein $R_4$ and $R_5$, together with the carbon atom to which they are attached, form a spirocyclopropyl.

Clause 13—The compound according to any one of clauses 1 to 5, wherein $R_4$ and $R_5$, together with the carbon atom to which they are attached, form a spirocyclobutyl.

Clause 14—The compound according to clause 1 selected from the group consisting of:
5,5-dimethyl-3-[5-(7-methylspiro[2H-benzofuran-3,1'-cyclopropane]-4-yl)oxypyrazin-2-yl]imidazolidine-2,4-dione;
3-[5-[(3,3-dimethyl-2H-benzofuran-4-yl)oxy]pyrazin-2-yl]-5,5-dimethyl-imidazolidine-2,4-dione;
(5R)-5-ethyl-5-methyl-3-(5-spiro[2H-benzofuran-3,1'-cyclopropane]-4-yloxypyrazin-2-yl)imidazolidine-2,4-dione;
5,5-dimethyl-3-(5-spiro[2H-benzofuran-3,1'-cyclopropane]-4-yloxypyrazin-2-yl)imidazolidine-2,4-dione;
(5R)-5-ethyl-5-methyl-3-[5-(7-methylspiro[2H-benzofuran-3,1'-cyclopropane]-4-yl)oxypyrazin-2-yl]imidazolidine-2,4-dione;
(5R)-3-[5-[(3,3-dimethyl-2H-benzofuran-4-yl)oxy]pyrazin-2-yl]-5-ethyl-5-methyl-imidazolidine-2,4-dione;
5,5-dimethyl-3-[5-[(3,3,7-trimethyl-2H-benzofuran-4-yl)oxy]pyrazin-2-yl]imidazolidine-2,4-dione;
(5R)-5-ethyl-5-methyl-3-[5-[(3,3,7-trimethyl-2H-benzofuran-4-yl)oxy]pyrazin-2-yl]imidazolidine-2,4-dione;
(5R)-5-ethyl-3-[5-(7-methylspiro[2H-benzofuran-3,1'-cyclopropane]-4-yl)oxypyrazin-2-yl]imidazolidine-2,4-dione;
(5R)-5-ethyl-3-(5-spiro[2H-benzofuran-3,1'-cyclopropane]-4-yloxypyrazin-2-yl)imidazolidine-2,4-dione;
(5R)-3-[5-[(3,3-dimethyl-2H-benzofuran-4-yl)oxy]pyrazin-2-yl]-5-ethyl-imidazolidine-2,4-dione;
(5R)-5-ethyl-3-[5-[(3,3,7-trimethyl-2H-benzofuran-4-yl)oxy]pyrazin-2-yl]imidazolidine-2,4-dione;
7-[5-(7-methylspiro[2H-benzofuran-3,1'-cyclopropane]-4-yl)oxypyrazin-2-yl]-5,7-diazaspiro[3.4]octane-6,8-dione;
6-[5-(7-methylspiro[2H-benzofuran-3,1'-cyclopropane]-4-yl)oxypyrazin-2-yl]-4,6-diazaspiro[2.4]heptane-5,7-dione;
(5S)-5-ethyl-3-[5-(7-methylspiro[2H-benzofuran-3,1'-cyclopropane]-4-yl)oxypyrazin-2-yl]imidazolidine-2,4-dione;
or a salt and/or solvate thereof and/or derivative thereof.

Clause 15—The compound according to clause 1 which is: 5,5-dimethyl-3-[5-(7-methylspiro[2H-benzofuran-3,1'-cyclopropane]-4-yl)oxypyrazin-2-yl]imidazolidine-2,4-dione.

Clause 16—The compound according to clause 1 which is: 3-[5-[(3,3-dimethyl-2H-benzofuran-4-yl)oxy]pyrazin-2-yl]-5,5-dimethyl-imidazolidine-2,4-dione.

Clause 17—The compound according to clause 1 which is: (5R)-5-ethyl-5-methyl-3-(5-spiro[2H-benzofuran-3,1'-cyclopropane]-4-yloxypyrazin-2-yl)imidazolidine-2,4-dione.

Clause 18—The compound according to clause 1 which is: 5,5-dimethyl-3-(5-spiro[2H-benzofuran-3,1'-cyclopropane]-4-yloxypyrazin-2-yl)imidazolidine-2,4-dione.

Clause 19—The compound according to clause 1 which is: (5R)-5-ethyl-5-methyl-3-[5-(7-methylspiro[2H-benzofuran-3,1'-cyclopropane]-4-yl)oxypyrazin-2-yl]imidazolidine-2,4-dione.

Clause 20—The compound according to clause 1 which is: (5R)-3-[5-[(3,3-dimethyl-2H-benzofuran-4-yl)oxy]pyrazin-2-yl]-5-ethyl-5-methyl-imidazolidine-2,4-dione.

Clause 21—The compound according to clause 1 which is: 5,5-dimethyl-3-[5-[(3,3,7-trimethyl-2H-benzofuran-4-yl)oxy]pyrazin-2-yl]imidazolidine-2,4-dione.

Clause 22—The compound according to clause 1 which is: (5R)-5-ethyl-5-methyl-3-[5-[(3,3,7-trimethyl-2H-benzofuran-4-yl)oxy]pyrazin-2-yl]imidazolidine-2,4-dione.

Clause 23—The compound according to clause 1 which is: (5R)-5-ethyl-3-[5-(7-methylspiro[2H-benzofuran-3,1'-cyclopropane]-4-yl)oxypyrazin-2-yl]imidazolidine-2,4-dione.

Clause 24—The compound according to clause 1 which is: (5R)-5-ethyl-3-(5-spiro[2H-benzofuran-3,1'-cyclopropane]-4-yloxypyrazin-2-yl)imidazolidine-2,4-dione.

Clause 25—The compound according to clause 1 which is: (5R)-3-[5-[(3,3-dimethyl-2H-benzofuran-4-yl)oxy]pyrazin-2-yl]-5-ethyl-imidazolidine-2,4-dione.

Clause 26—The compound according to clause 1 which is: (5R)-5-ethyl-3-[5-[(3,3,7-trimethyl-2H-benzofuran-4-yl)oxy]pyrazin-2-yl]imidazolidine-2,4-dione.

Clause 27—The compound according to clause 1 which is: 7-[5-(7-methylspiro[2H-benzofuran-3,1'-cyclopropane]-4-yl)oxypyrazin-2-yl]-5,7-diazaspiro[3.4]octane-6,8-dione.

Clause 28—The compound according to clause 1 which is: 6-[5-(7-methylspiro[2H-benzofuran-3,1'-cyclopropane]-4-yl)oxypyrazin-2-yl]-4,6-diazaspiro[2.4]heptane-5,7-dione.

Clause 29—The compound according to clause 1 which is: (5S)-5-ethyl-3-[5-(7-methylspiro[2H-benzofuran-3,1'-cyclopropane]-4-yl)oxypyrazin-2-yl]imidazolidine-2,4-dione.

Clause 30—The compound of formula (I) according to any one of clauses 1 to 29, or a pharmaceutically acceptable salt and/or solvate thereof.

Clause 31—The compound according to any one of clauses 1 to 30 for use as a medicament.

Clause 32—The compound according to clause 31 for use in the prophylaxis or treatment of a disease or disorder selected from the group consisting of hearing disorders, schizophrenia, depression and mood disorders, bipolar disorder, substance abuse disorders, anxiety disorders, sleep disorders, hyperacusis and disturbances of loudness perception, Mèniére's disease, disorders of balance, and disorders of the inner ear, impulse control disorder, personality disorders, attention-deficit/hyperactivity disorder, autism spectrum disorders, eating disorders, cognition impairment, ataxia, pain such as neuropathic pain, inflammatory pain and miscellaneous pain, Lewy body dementia and Parkinson's disease.

Clause 33—The compound according to clause 31 for use in the prophylaxis or treatment of schizophrenia.

Clause 34—The compound according to clause 31 for use in the prophylaxis or treatment of hearing disorders.

Clause 35—The compound according to clause 31 for use in the prophylaxis or treatment of pain.

Clause 36—The compound according to clause 31 for use in the treatment of Fragile X.

Clause 37—A method for the prophylaxis or treatment of a disease or disorder selected from the group consisting of hearing disorders, schizophrenia, depression and mood disorders, bipolar disorder, substance abuse disorders, anxiety disorders, sleep disorders, hyperacusis and disturbances of loudness perception, Mèniére's disease, disorders of balance, and disorders of the inner ear, impulse control disorder, personality disorders, attention-deficit/hyperactivity disorder, autism spectrum disorders, eating disorders, cognition impairment, ataxia, pain such as neuropathic pain, inflammatory pain and miscellaneous pain, Lewy body dementia and Parkinson's disease which comprises administering to a subject in need thereof an effective amount of a compound according to any one of clauses 1 to 30.

Clause 38—A method for the prophylaxis or treatment of schizophrenia, comprising administering to a subject in need thereof a compound according to any one of clauses 1 to 30.

Clause 39—A method for the prophylaxis or treatment of hearing disorders, comprising administering to a subject in need thereof a compound according to any one of clauses 1 to 30.

Clause 40—A method for the prophylaxis or treatment of pain, comprising administering to a subject in need thereof a compound according to any one of clauses 1 to 30.

Clause 41—A method for the treatment of Fragile X, comprising administering to a subject in need thereof a compound according to any one of clauses 1 to 30.

Clause 42—Use of a compound according to any one of clauses 1 to 30 in the manufacture of a medicament for the prophylaxis or treatment of a disease or disorder selected from the group consisting of hearing disorders, schizophrenia, depression and mood disorders, bipolar disorder, substance abuse disorders, anxiety disorders, sleep disorders, hyperacusis and disturbances of loudness perception, Mèniére's disease, disorders of balance, and disorders of the inner ear, impulse control disorder, personality disorders, attention-deficit/hyperactivity disorder, autism spectrum disorders, eating disorders, cognition impairment, ataxia, pain such as neuropathic pain, inflammatory pain and miscellaneous pain, Lewy body dementia and Parkinson's disease.

Clause 43—Use of a compound according to any one of clauses 1 to 30 in the manufacture of a medicament for the prophylaxis or treatment of schizophrenia.

Clause 44—Use of a compound according to any one of clauses 1 to 30 in the manufacture of a medicament for the prophylaxis or treatment of hearing disorders.

Clause 45—Use of a compound according to any one of clauses 1 to 30 in the manufacture of a medicament for the prophylaxis or treatment of pain.

Clause 46—Use of a compound according to any one of clauses 1 to 30 in the manufacture of a medicament for the treatment of Fragile X.

Clause 47—A pharmaceutical composition comprising a compound of any one of clauses 1 to 30 and a pharmaceutically acceptable carrier or excipient.

Clause 48—The compound according to any one of clauses 1 to 30 for use in combination with a further pharmaceutically acceptable active ingredient.

Clause 49—A compound of formula (II) or (XVI):

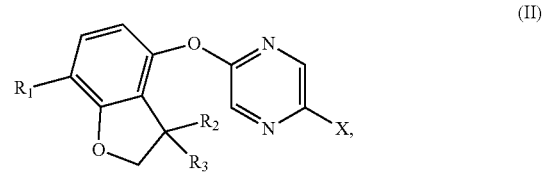

(II)

wherein $R_1$, $R_2$ and $R_3$ are as defined in clause 1, X is halo, such as Br.

Clause 50—A compound of formula (XVI):

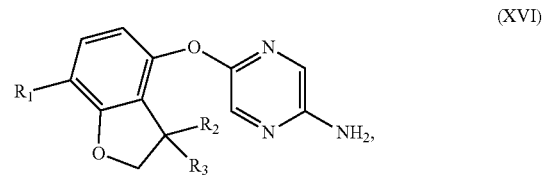

(XVI)

wherein $R_1$, $R_2$ and $R_3$ are as defined in clause 1.

Clause 51—A compound of formula (IV):

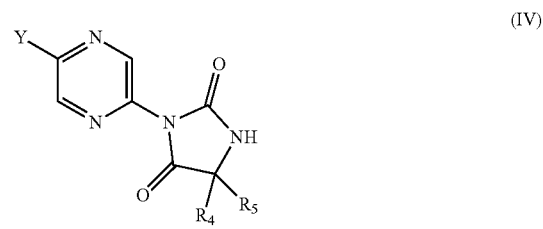

(IV)

wherein $R_4$ and $R_5$ are as defined in clause 1, Y is halo, such as Cl.

Clause 52—A derivative of a compound of formula (I), or salt and/or solvate thereof, according to any one of clauses 1 to 30 functionalised via the secondary nitrogen of the hydantoin or via the secondary nitrogen of the triazolone with a group L, wherein L is selected from the groups consisting of:

a) —PO(OH)O$^-$·M$^+$, wherein M$^+$ is a pharmaceutically acceptable monovalent counterion,
b) —PO(O$^-$)$_2$·2M$^+$,
c) —PO(O$^-$)$_2$·D$^{2+}$, wherein D$^{2+}$ is a pharmaceutically acceptable divalent counterion,
d) —CH(R$^X$)—PO(OH)O$^-$·M$^+$, wherein R$^X$ is hydrogen or C$_{1-3}$ alkyl,
e) —CH(R$^X$)—PO(O$^-$)$_2$·2M$^+$,
f) —CH(R$^X$)—PO(O$^-$)$_2$·D$^{2+}$,
g) —SO$_3$$^-$·M$^+$,
h) —CH(R$^X$)—SO$_3$$^-$·M$^+$, and
i) —CO—CH$_2$CH$_2$—CO$_2$·M$^+$.

Clause 53—The compound according to any one of clauses 1 to 36, which is in natural isotopic form.

Clause 54—The compound, method, use, composition or derivative according to any one of clauses 1 to 48, 52 or 53, for oral administration.

Clause 55—The compound, method, use, composition or derivative according to any one of clauses 1 to 48 or 52 to 54 for administration at 2 to 400 mg per day, such as 2 to 300 mg per day, especially 5 to 250 mg per day.

Clause 56—The compound, method, use, composition or derivative according to any one of clauses 1 to 48 or 52 to 55 for administration once or twice per day.

Clause 57—The compound according to clause 56 for administration once per day.

Clause 58—The compound according to clause 56 for administration twice per day.

Clause 59—The compound, method, use, composition or derivative according to any one of clauses 1 to 48 or 52 to 58 for administration for a period of at least three months.

Clause 60—The compound, method, use, composition or derivative according to any one of clauses 1 to 48 or 52 to 58 for administration to a human subject.

Clause 61—The compound, method, use, composition or derivative according to clause 60 for administration to a human adult, such as aged 18 to 65.

Clause 62—The compound, method, use, composition or derivative according to clause 60 for administration to a human aged 66 years old or older.

Clause 63—The compound, method, use, composition or derivative according to clause 60 to a human subject of less than 18 years of age, such as 4 to 17 years old.

Clause 64—The compound, method, use, composition or derivative according to according to any one of clauses 1 to 48, 52, 53 or 59 to 63 wherein a compound of formula (I) or a pharmaceutically acceptable, salt, solvate and/or derivative thereof is delivered by a patch or implant.

REFERENCES

All publications, including but not limited to patents and patent applications, cited in this specification are herein incorporated by reference as if each individual publication were specifically and individually indicated to be incorporated by reference herein as though fully set forth.

Anderson L A et al. Increased spontaneous firing rates in auditory midbrain following noise exposure are specifically abolished by a Kv3 channel modulator. *Hear Res.* 2018 August; 365:77-89

Aroniadou-Anderjaska V et al. Mechanisms regulating GABAergic inhibitory transmission in the basolateral amygdala: implications for epilepsy and anxiety disorders. *Amino Acids* 2007 August; 32:305-315.

Baranauskas G, Nistri A. Sensitization of pain pathways in the spinal cord: cellular mechanisms. *Prog. Neurobiol.* 1998 February; 54(3):349-65.

Baron R et al. Peripheral input and its importance for central sensitization. *Ann. Neurol.* 2013 November; 74(5):630-6.

Ben-Ari Y. Seizure Beget Seizure: The Quest for GABA as a Key Player. *Crit. Rev. Neurobiol.* 2006; 18(1-2):135-144.

Benes F M et al. Circuitry-based gene expression profiles in GABA cells of the trisynaptic pathway in schizophrenics versus bipolars. *PNAS* 2008 December; 105(52):20935-20940.

Bennett D L, Woods C G. Painful and painless channelopathies. Lancet Neurol. 2014 June; 13(6):587-99.

Berge S et al. Pharmaceutical Salts. *J. Pharm. Sci.* 1977; 66; 1-19.

Brambilla P et al. GABAergic dysfunction in mood disorders. *Mol. Psych.* 2003 April; 8:721-737.

Brooke R E et al. Spinal cord interneurones labelled transneuronally from the adrenal gland by a GFP-herpes virus construct contain the potassium channel subunit Kv3.1b. *Auton. Neurosci.* 2002 June; 98(1-2):45-50.

Brooke R E et al. Association of potassium channel Kv3.4 subunits with pre- and post-synaptic structures in brainstem and spinal cord. *Neuroscience* 2004; 126(4):1001-10.

Brooke R E et al. Immunohistochemical localisation of the voltage gated potassium ion channel subunit Kv3.3 in the rat medulla oblongata and thoracic spinal cord. *Brain Res.* 2006 January; 1070(1):101-15.

Cervero F. Spinal cord hyperexcitability and its role in pain and hyperalgesia. *Exp. Brain Res.* 2009 June; 196(1):129-37.

Chambers A R et al. Pharmacological modulation of Kv3.1 mitigates auditory midbrain temporal processing deficits following auditory nerve damage. *Sci Rep.* 2017 Dec. 13; 7(1):17496

Chang S Y et al. Distribution of Kv3.3 Potassium Channel Subunits in Distinct Neuronal Populations of Mouse Brain. *J. Comp. Neuro.* 2007 February; 502:953-972.

Chien L Y et al. Reduced expression of A-type potassium channels in primary sensory neurons induces mechanical hypersensitivity. *J. Neurosci.* 2007 September; 27(37): 9855-65.

Chow A et al. $K^+$ Channel Expression Distinguishes Subpopulations of Parvalbumin- and Somatostatin-Containing Neocortical Interneurons. *J. Neurosci.* 1999 November; 19(21):9332-9345.

Desai R et al. Protein Kinase C Modulates Inactivation of Kv3.3 Channels. *J. Biol. Chem.* 2008; 283; 22283-22294.

Deuchars S A et al. Properties of interneurones in the intermediolateral cell column of the rat spinal cord: role of the potassium channel subunit Kv3.1. *Neuroscience* 2001; 106(2):433-46.

Devulder J. Flupirtine in pain management: pharmacological properties and clinical use. *CNS Drugs* 2010 October; 24(10):867-81.

Dib-Hajj S D et al. The Na(V)1.7 sodium channel: from molecule to man. *Nat. Rev. Neurosci.* 2013 January; 14(1):49-62.

Diochot S et al. Sea Anemone Peptides with a Specific Blocking Activity against the Fast Inactivating Potassium Channel Kv3.4. *J. Biol. Chem.* 1998 March; 273(12); 6744-6749.

Engel A K et al. Dynamic Predictions: Oscillations and Synchrony in Top-Down Processing. *Nat. Rev. Neurosci.* 2001 October; 2(10):704-716.

Espinosa F et al. Alcohol Hypersensitivity, Increased Locomotion, and Spontaneous Myoclonus in Mice Lacking the Potassium Channels Kv3.1 and Kv3.3. *J. Neurosci.* 2001 September; 21(17):6657-6665.

Espinosa F et al. Ablation of Kv3.1 and Kv3.3 Potassium Channels Disrupts Thalamocortical Oscillations In Vitro and In Vivo. *J. Neurosci.* 2008 May; 28(21):5570-5581.

Figueroa K et al. KCNC3: phenotype, mutations, channel biophysics—a study of 260 familial ataxia patients. *Human Mutation.* 2010; 31; 191-196.

Finnerup N B et al. Pharmacotherapy for neuropathic pain in adults: a systematic review and meta-analysis. *Lancet Neurol.* 2015 February; 14(2):162-73.

Fisahn A. Kainate receptors and rhythmic activity in neuronal networks: hippocampal gamma oscillations as a tool. *J. Physiol.* 2005 October; 561(1):65-72.

Glait L et al. Effects of AUT00063, a Kv3.1 channel modulator, on noise-induced hyperactivity in the dorsal cochlear nucleus. *Hear Res.* 2018 April; 361:36-44

Greene T W, Wuts, P G. Greene's *Protective Groups in Organic Synthesis*, 2006, 4th Edition, John Wiley & Sons, Inc., Hoboken, N J, USA.

Joho R H et al. Increased y- and Decreased 6-Oscillations in a Mouse Deficient for a Potassium Channel Expressed in Fast-Spiking Interneurons. *J. Neurophysiol.* 1999 June; 82:1855-1864.

Joho R H, Hurlock E C. The Role of Kv3-type Potassium Channels in Cerebellar Physiology and Behavior. *Cerebellum* 2009 February; 8:323-333.

Jung D et al. Age-related changes in the distribution of Kv1.1 and Kv3.1 in rat cochlear nuclei. *Neurol. Res.* 2005; 27; 436-440.

Kasten M R et al. Differential regulation of action potential firing in adult murine thalamocortical neurons by Kv3.2, Kv1, and S K potassium and N-type calcium channels. *J. Physiol.* 2007; 584(2):565-582.

Kaczmarek L et al. Regulation of the timing of MNTB neurons by short-term and long-term modulation of potassium channels. *Hearing Res.* 2005; 206; 133-145.

Lau D et al. Impaired Fast-Spiking, Suppressed Cortical Inhibition, and Increased Susceptibility to Seizures in Mice Lacking Kv3.2 $K^+$ Channel Proteins. *J. Neurosci.* 2000 December; 20(24):9071-9085.

Li W et al. Localization of Two High-Threshol Potassium Channel Subunits in the Rat Central Auditory System. *J. Comp. Neuro.* 2001 May; 437:196-218.

Lu R et al. Slack channels expressed in sensory neurons control neuropathic pain in mice. *J. Neurosci.* 2015 January; 35(3):1125-35.

Markram H et al. Interneurons of the neocortical inhibitory system. *Nat. Rev. Neurosci.* 2004 October; 5:793-807.

Martina M et al. Functional and Molecular Differences between Voltage-Gated $K^+$ Channels of Fast-Spiking Interneurons and Pyramidal Neurons of Rat Hippocampus. *J. Neurosci.* 1998 October; 18(20):8111-8125.

McCarberg B H et al. The impact of pain on quality of life and the unmet needs of pain management: results from pain sufferers and physicians participating in an Internet survey. *Am. J. Ther.* 2008 July-August; 15(4):312-20.

McDonald A J, Mascagni F. Differential expression of Kv3.1b and Kv3.2 potassium channel subunits in interneurons of the basolateral amygdala. *Neuroscience* 2006; 138:537-547.

McMahon A et al. Allele-dependent changes of olivocerebellar circuit properties in the absence of the voltage-gated potassium channels Kv3.1 and Kv3.3. *Eur. J. Neurosci.* 2004 March; 19:3317-3327.

Mitchell I et al. Aryl Pyrazoles as Potent Inhibitors of Arginine Methyltransferases: Identification of the First PRMT6 Tool Compound. *ACS Med. Chem. Lett.* 2015; 6(6); 655-659.

Muona M, et al. A recurrent de novo mutation in KCNC1 causes progressive myoclonus epilepsy. *Nat Genet.* 2015 January; 47(1):39-46.

Muqeem T et al. Regulation of Nociceptive Glutamatergic Signaling by Presynaptic Kv3.4 Channels in the Rat Spinal Dorsal Horn *J Neurosci.* 2018 Apr. 11; 38(15): 3729-3740

Olsen T et al. Kv3 K+ currents contribute to spike-timing in dorsal cochlear nucleus principal cells. *Neuropharmacology* 2018 May 1; 133:319-333

Pilati N et al., Acoustic over-exposure triggers burst firing in dorsal cochlear nucleus fusiform cells. *Hearing Research* 2012; 283; 98-106.

Puente N et al. Precise localization of the voltage-gated potassium channel subunits Kv3.1b and Kv3.3 revealed in the molecular layer of the rat cerebellar cortex by a pre-embedding immunogold method. *Histochem. Cell. Biol.* 2010 September; 134:403-409.

Reynolds G P et al. Calcium Binding Protein Markers of GABA Deficits in Schizophrenia—Post Mortem Studies and Animal Models. *Neurotox. Res.* 2004 February; 6(1): 57-62.

Ritter D M et al. Modulation of Kv3.4 channel N-type inactivation by protein kinase C shapes the action potential in dorsal root ganglion neurons. *J. Physiol.* 2012 January; 590 (Pt 1):145-61.

Ritter D M et al. Dysregulation of Kv3.4 channels in dorsal root ganglia following spinal cord injury. *J. Neurosci.* 2015 January; 35(3):1260-73.

Roberts L et al. Ringing Ears: The Neuroscience of Tinnitus. *J. Neurosci.* 2010:30 (45); 14972-14979.

Rudy B, McBain C J. Kv3 channels: voltage-gated K+ channels designed for high-frequency repetitive firing. *TRENDS in Neurosci.* 2001 September; 24(9):517-526.

Sacco T et al. Properties and expression of Kv3 channels in cerebellar Purkinje cells. *Mol. Cell. Neurosci.* 2006 July; 33:170-179.

Schulz P, Steimer T. Neurobiology of Circadian Systems. *CNS Drugs* 2009; 23 (Suppl. 2):3-13.

Song P et al. Acoustic environment determines phosphorylation state of the Kv3.1 potassium channel in auditory neurons *Nat. Neurosci.* 2005 October; 8(10): 1335-1342.

Spencer K M et al. Neural synchrony indexes disordered perception and cognition in schizophrenia. *PNAS* 2004 December; 101(49):17288-17293.

Sun S et al. Inhibitors of voltage-gated sodium channel Nav1.7: patent applications since 2010. *Pharm. Pat. Anal.* 2014 September; 3(5):509-21.

U.S. Department of Health and Human Services, Food and Drug Administration. Draft Guidance for Industry Analgesic Indications: Developing Drug and Biological Products: fdanews.com/ext/resources/files/02/02-05-14-Analgesic.pdf 2014 February von Hehn C et al. Loss of Kv3.1 Tonotopicity and Alterations in cAMP Response Element-Binding Protein Signaling in Central Auditory Neurons of Hearing Impaired Mice. *J. Neurosci.* 2004; 24: 1936-1940.

Weiser M et al. Differential Expression of Shaw-related $K^+$ Channels in the Rat Central Nervous System. *J. Neurosci.* 1994 March; 14(3):949-972.

Wickenden A D, McNaughton-Smith G. Kv7 channels as targets for the treatment of pain. *Curr. Pharm. Des.* 2009; 15(15):1773-98.

Woolf C J. What is this thing called pain?*J. Clin. Invest.* 2010 November; 120(11):3742-4.

Woolf C J. Central sensitization: implications for the diagnosis and treatment of pain. *Pain* 2011 March; 152 (3 Suppl):S2-15.

Yanagi M et al. Kv3.1-containing K(+) channels are reduced in untreated schizophrenia and normalized with antipsychotic drugs. Mol Psychiatry. 2014. 19(5):573-9.

Yeung S Y M et al. Modulation of Kv3 Subfamily Potassium Currents by the Sea Anemone Toxin BDS: Significance for CNS and Biophysical Studies. *J. Neurosci.* 2005 March; 25(38):8735-8745.

Zamponi G W et al. The Physiology, Pathology, and Pharmacology of Voltage-Gated Calcium Channels and Their Future Therapeutic Potential *Pharmacol Rev.* 2015 October; 67(4):821-70.

The invention claimed is:

1. A compound which is:

(5R)-5-ethyl-3-[5-(7-methylspiro[2H-benzofuran-3,1'-cyclopropane]-4-yl)oxypyrazin-2-yl]imidazolidine-2,4-dione

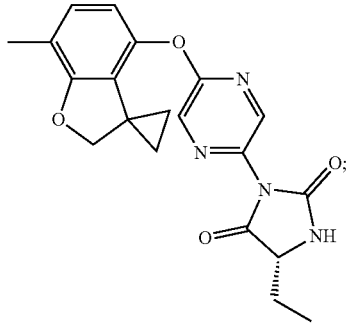 [SMILES: CC[C@H]1NC(=O)N(c2cnc(Oc3ccc(C)c4c3C3(CC3)CO4)cn2)C1=O]

or a pharmaceutically acceptable salt and/or solvate thereof.

2. A compound which is:

(5R)-5-ethyl-3-[5-(7-methylspiro[2H-benzofuran-3,1'-cyclopropane]-4-yl)oxypyrazin-2-yl]imidazolidine-2,4-dione:

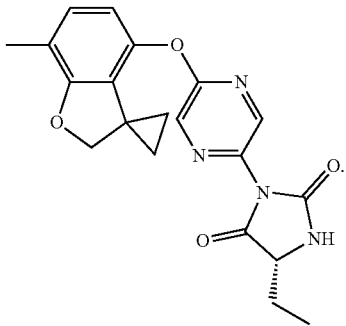 [SMILES: CC[C@H]1NC(=O)N(c2cnc(Oc3ccc(C)c4c3C3(CC3)CO4)cn2)C1=O]

3. A pharmaceutically acceptable salt of (5R)-5-ethyl-3-[5-(7-methylspiro[2H-benzofuran-3,1'-cyclopropane]-4-yl)oxypyrazin-2-yl]imidazolidine-2,4-dione:

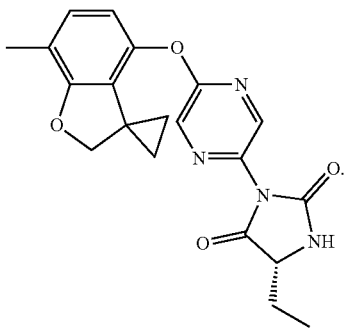 [SMILES: CC[C@H]1NC(=O)N(c2cnc(Oc3ccc(C)c4c3C3(CC3)CO4)cn2)C1=O]

* * * * *